United States Patent [19]

Sauter et al.

[11] Patent Number: 5,573,999
[45] Date of Patent: Nov. 12, 1996

[54] β-SUBSTITUTED CINNAMIC ACID DERIVATIVE

[75] Inventors: Hubert Sauter, Mannheim; Herbert Bayer, Ludwigshafen; Klaus Oberdorf, Heidelberg; Horst Wingert, Mannheim; Wolfgang von Deyn, Neustadt; Wassilios Grammenos, Ludwigshafen; Hartmann Koenig, Limburgerhof; Harald Rang; Franz Roehl, both of Ludwigshafen; Gisela Lorenz, Neustadt; Eberhard Ammermann, Ludwigshafen, all of Germany

[73] Assignee: BASF Aktiengesellschaft, Ludwigshafen, Germany

[21] Appl. No.: 441,639

[22] Filed: May 15, 1995

Related U.S. Application Data

[63] Continuation of Ser. No. 173,936, Dec. 28, 1993, abandoned, which is a continuation of Ser. No. 919,270, Jul. 27, 1992, abandoned.

[30] Foreign Application Priority Data

Jul. 27, 1991 [DE] Germany ............... 41 24 989.5

[51] Int. Cl.⁶ .................................. A01N 37/10
[52] U.S. Cl. ................. 504/266; 504/336; 504/314; 504/315; 504/316; 504/265; 504/263; 504/280; 504/271; 504/292; 504/294; 504/289; 504/267; 504/254; 504/247; 504/276; 504/261; 504/252; 558/198; 564/182; 564/167; 546/280.4; 546/312; 546/300; 546/114; 546/302; 546/157; 546/301; 546/153; 546/335; 546/342; 546/272.1; 546/271.4; 560/55; 560/60; 560/35; 560/21; 560/53; 560/9; 548/131; 548/136; 548/142; 548/144; 548/204; 548/377.1; 548/247; 548/560; 548/563; 548/235; 548/221; 548/307.1; 548/251; 548/264.2; 549/415; 549/79; 549/420; 549/484

[58] Field of Search ................... 560/55, 60, 35, 560/21, 53, 9; 558/198; 564/182, 167; 548/131, 136, 142, 144, 204, 377.1, 247, 560, 563, 235, 221, 307.1, 251, 264.2; 546/302, 284, 157; 549/415, 79, 420, 484; 504/266, 336, 314, 315, 316, 265, 263, 280, 271, 292, 294, 289, 267, 254, 247, 276, 261, 252

[56] References Cited

U.S. PATENT DOCUMENTS

| | | |
|---|---|---|
| 4,212,644 | 7/1980 | Degen et al. . |
| 4,296,120 | 10/1981 | Kadin . |
| 4,709,078 | 11/1987 | Schirmer et al. ............... 560/60 |
| 4,753,934 | 6/1988 | Nicki et al. . |
| 4,912,006 | 3/1990 | Breitschaft et al. . |
| 5,003,101 | 3/1991 | Brand et al. ............... 560/104 |

FOREIGN PATENT DOCUMENTS 2106742  3/1994  Canada .

| | | |
|---|---|---|
| 0009386 | 9/1979 | European Pat. Off. . |
| 0178826 | 4/1986 | European Pat. Off. . |
| 0224823 | 6/1987 | European Pat. Off. . |
| 0235722 | 9/1987 | European Pat. Off. . |

(List continued on next page.)

OTHER PUBLICATIONS

Chemical Abstracts 70:67821; 1968 Rigaudy et al.
Chemical Abstracts 64: 9625a; 1966 RN 4843-31-6.
Tetrahedron Letts. 23(12), 1301-4; Frimer et al; 1982.
J. Org. Chem. 1986, 51, 1402-1406 Steric Effects in the Synthesis of 1,7-Dialkylindan Ronald Budhram, Ventakapuran Palaniswamy . . . .

(List continued on next page.)

Primary Examiner—Samuel Barts
Attorney, Agent, or Firm—Oblon, Spivak, McClelland, Maier & Neustadt, P.C.

[57] ABSTRACT

β-Substituted cinnamic acid derivatives of the formula 1,

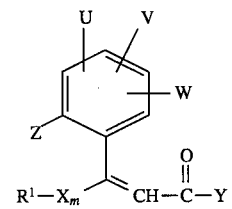

where
$R^1$ is alkyl, chlorine or bromine, —X— is —O—, —S—,

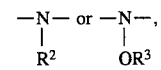

m is 0 or 1,
—Y is —OR⁴, —O—N=CR⁵R⁶, —NR⁷R⁸, —N(OR⁹)R¹⁰ or —SR¹¹, where the above-mentioned substituents $R^2$ to $R^{11}$ are alkyl, and $R^2$, and $R^3$ and $R^5$ to $R^{11}$ can also be hydrogen, Z is halogen, nitro, cyano, alkyl, cycloalkyl, aralkyl, aryloxyalkyl, arylthioalkyl, hetarylalkyl, hetaryloxyalkyl, hetarylthioalkyl, alkenyl, aralkenyl, aryloxyalkenyl, arylthioalkenyl, hetarylalkenyl, hetaryloxyalkenyl, hetarylthioalkenyl, alkynyl, arylalkynyl, hetarylalkynyl, aryl, hetaryl, arylazo, acylamino, —OR¹², —SR¹³, —SOR¹⁴, —SO₂R¹⁵, —COOR¹⁶, —CONR¹⁷R¹⁸, —COR¹⁹, —CR²⁰=NR²¹, —N=CR²², R²³, —CR²⁴=N—OR²⁵, —CR²⁵R²⁶—O—, N=CR²⁷R²⁸, —CH₂—OCOR³⁹ or —NR³⁷R³⁸, where $R^2$ and $R^{38}$ and $R^{39}$ are hydrogen, alkyl, alkenyl, alkynyl, cycloalkyl, cycloalkylalkyl, aryl, hetaryl, aralkyl, hetarylalkyl, aryloxyalkyl, arylthioalkyl, hetaryloxyalkyl or hetarylthioalkyl, and $r^{37}$ is hydrogen or $C_1$–$C_4$-alkyl, are useful as fungicides and insecticides.

12 Claims, No Drawings

FOREIGN PATENT DOCUMENTS

| | | |
|---|---|---|
| 0251082 | 1/1988 | European Pat. Off. . |
| 0260832 | 3/1988 | European Pat. Off. . |
| 0342459 | 11/1989 | European Pat. Off. . |
| 0407891 | 1/1991 | European Pat. Off. . |
| 0575805 | 12/1993 | European Pat. Off. . |
| 0590446 | 4/1994 | European Pat. Off. . |
| 1542872 | 7/1970 | Germany . |
| 2108234 | 3/1971 | Germany . |
| 2733468 | 2/1979 | Germany . |
| 4-264454 | 9/1992 | Japan . |

OTHER PUBLICATIONS

Acta Chemica Scandinavica, vol. B40, No. 4, 1986, pp. 303–309, H. Storflor, et al., "Potentially Aromatic Thiophenium Ylides 4. Formation and Cyclization of Methyl and Methoxycarbonyl Substituted 2-(2-Thienyl)Benzoylcarbenes".

Journal of Medicinal Chemistry, vol. 20, No. 6, 1977, pp. 781–791, R. Parker, et al., "5–9Tetradecyloxy)–2–Furancarboxylic Acid and Related Hypolipidemic Fatty Acid–Like Alkyloxyaryl Carboxylic Acids".

Chemical Abstracts, vol. 115, No. 3, Jul. 22, 1991, AN–28568, p. 701.

Tetrahedron Letters, vol. 44, 1973, V. Viswanatha, et al., "Unusual Products of Oxidation with CR(VI) of Methyl 5–Methyl–7–Methoxy–8–Isopropyl–3,4–Dihydro–2–Naphthoate".

Chemische Berichte, vol. 103, No. 7, 1970, pp. 2320–2325, A. Rahman, et al., "Notiz Uber Die Totalsynthese Von 1–Methyl–2.3–Dihydro–1H–Cyclopenta(l)Phenanthren Durch Succinoylierung Und Acetylierung Von Naphthalin".

Journal of the American Chemical Society, vol. 106, No. 10, 1984, pp. 2870–2874, D. Cabaret, et al., "Atropisomeric Alkenyl Cobaloximes. Stereochemical Study of the Vinyl Halide Substitution by Transition–Metal Complexes".

Chemical Abstracts, vol. 107, No. 23, Dec. 7, 1987, AN–217432, p. 571, A. Frimer, et al., "Reaction of Coumarins with Superoxide Anion Radical".

Journal of the Chemical Society, Perkins Transactions I, No. 5, 1984, pp. 1053–1059, F. J. Leeper, et al., "Biomimetic Synthesis of Polyketide Aromatics from Reaction of an Orsellinate Anion with Pyrones and a Pyrylium Salt".

Journal of Organic Chemistry, vol. 56, No. 4, Feb. 15, 1991, pp. 1364–1373, P. Deshong, et al., "A Nitrone–Based Cycloaddition Approach to the Synthesis of Glycosyl System of Nogalomycin, Menogaril, and their Congeners".

Chemical Abstracts, vol. 117, No. 15, Oct. 12, 1992, AN–150724n, JP–A–4 091 065, Mar. 24, 1992.

β-SUBSTITUTED CINNAMIC ACID DERIVATIVE

This application is a continuation of application Ser. No. 08/173,936, filed on Dec. 28, 1993, now abandoned, which is a continuation of application Ser. No. 07/919,270, filed Jul. 27, 1992, abandoned.

The present invention relates to novel β-substituted cinnamic acid derivatives which inhibit the mitochondrial respiration of fungi, insects and spider mites, and which have antimycotic, insecticidal and acaricidal effects and, in particular, fungicidal effects on phytopathogenic fungi.

The present invention also relates to processes for the preparation of compounds of this type and to intermediates for the preparation thereof, and to processes and agents for use as fungicides, antimycotics, insecticides and acaricides, which respectively make use of and contain these β-substituted cinnamic acid derivatives.

The use of amides of cinnamic acid, e.g. of the morpholide of β-phenylcinnamic acid, as fungicide has been disclosed (DE 3 306 996). However, its fungicidal effect is unsatisfactory.

The present invention relates to β-substituted cinnamic acid derivatives of the formula 1

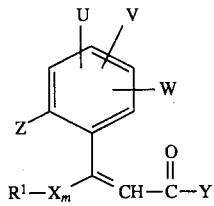

where $R^1$ is unsubstituted or halogen-(F, Cl, Br, I), $C_1$–$C_6$-alkoxy-, $C_1$–$C_6$-alkylthio- or $C_3$–$C_6$-cycloalkyl-substituted, $C_1$–$C_8$-alkyl, $C_2$–$C_8$-alkenyl, $C_2$–$C_8$-alkynyl, $C_3$–$C_8$-cycloalkyl or $C_3$–$C_8$-cycloalkenyl, and $R^1$ can also be chlorine or bromine when m is 0, —X— is —O—, —S—,

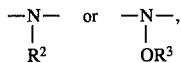

m is 0 or 1,

—Y is —$OR^4$, —O—N=$CR^5R^6$, —$NR^7R^8$, —N($OR^9$)$R^{10}$ or —$SR^{11}$, where the abovementioned substituents $R^2$ to $R^{11}$ are, independently of one another, identical or different and each is unsubstituted or halogen-(F, Cl, Br, I), $C_1$–$C_6$-alkoxy-, $C_1$–$C_6$-alkylthio- or $C_3$–$C_6$-cycloalkyl- substituted $C_1$–$C_8$-alkyl, $C_2$–$C_8$-alkenyl, $C_2$–$C_8$-alkynyl, $C_3$–$C_8$-cycloalkyl or $C_3$–$C_8$-cycloalkenyl, and $R^2$, $R^3$ and $R^5$ to $R^{11}$ can also be hydrogen with the restriction that $R^4$ is not ethyl or t-butyl when m is 0, Z is halogen (F, Cl, Br, I), nitro, cyano, unsubstituted or substituted alkyl, unsubstituted or substituted cycloalkyl, unsubstituted or substituted aralkyl, unsubstituted or substituted aryloxyalkyl, unsubstituted or substituted arylthioalkyl, unsubstituted or substituted hetarylalkyl, unsubstituted or substituted hetaryloxyalkyl, unsubstituted or substituted hetarylthioalkyl, unsubstituted or substituted alkenyl, unsubstituted or substituted aralkenyl, unsubstituted or substituted aryloxyalkenyl, unsubstituted or substituted arylthioalkenyl, unsubstituted or substituted hetarylalkenyl, unsubstituted or substituted hetaryloxyalkenyl, unsubstituted or substituted hetarylthioalkenyl, unsubstituted or substituted alkynyl, unsubstituted or substituted arylalkynyl, unsubstituted or substituted hetarylalkynyl, unsubstituted or substituted aryl, unsubstituted or substituted hetaryl, unsubstituted or substituted arylazo, unsubstituted or substituted acylamino, —$OR^{12}$, —$SR^{13}$, —$SOR^{14}$, —$SO_2R^{15}$, —$COOR^{16}$, —$CONR^{17}R^{18}$, —$COR^{19}$, —$CR^{20}$=$NR^{21}$, —N=$CR^{22}R^{23}$, —$CR^{24}$=N—$OR^{25}$, —$CR^{25}R^{26}$—O—N=$CR^{27}R^{28}$, —$CH_2$—$OCOR^{39}$ or —$NR^{37}R^{38}$, where $R^{12}$ to $R^{28}$, and $R^{38}$ and $R^{39}$ are identical or different and are hydrogen, unsubstituted or substituted alkyl, unsubstituted or substituted alkenyl, unsubstituted or substituted alkynyl, unsubstituted or substituted cycloalkyl, unsubstituted or substituted cycloalkylalkyl, unsubstituted or substituted aryl, unsubstituted or substituted hetaryl, unsubstituted or substituted aralkyl, unsubstituted or substituted hetarylalkyl, unsubstituted or substituted aryloxyalkyl, unsubstituted or substituted arylthioalkyl, unsubstituted or substituted hetaryloxyalkyl or unsubstituted or substituted hetarylthioalkyl, and $R^{37}$ is hydrogen or $C_1$–$C_4$-alkyl with the restriction that Z is not formyl or $R^{12}$ is not unsubstituted or substituted alkyl when m is 0, and where U, V and W are identical or different and are hydrogen or have one of the meanings specified for Z, or where two of the groups Z, U, V or W in adjacent positions on the phenyl ring may together form an unsubstituted or substituted five- or six-membered aromatic or aliphatic ring which is fused onto the phenyl ring and may contain one to three hetero atoms (N, S, O).

Examples of $R^1$ to $R^{11}$ in the compounds of the formula 1 are the following: methyl, ethyl, n-propyl, isopropyl, tert-butyl, n-octyl, 2-ethylhexyl, 2-chloroethyl, 3-bromopropyl, 2-methoxyethyl, 2-isopropoxyethyl, 1-methoxy-2-propyl, 2-ethylthioethyl, cyclopropylmethyl, cyclohexylmethyl, allyl, 2-chloroallyl, propargyl, 4-ethoxy-2-pentynyl, 1-methycyclopropyl and 2-cyclohexenyl.

$R^1$ to $R^{11}$ preferably have up to 4 carbon atoms and are particularly preferably ethyl and especially methyl. In addition, hydrogen is preferred for $R^5$ to $R^{10}$.

Alkyl for Z and $R^{12}$ to $R^{28}$, $R^{38}$ and $R^{39}$ in the compounds of the formula 1 is, as independent group or as part of a group (eg. in alkoxy, alkylthio, hetarylalkyl, aryloxyalkyl), straight-chain or branched with 1 to 10 carbon atoms, preferably with 1 to 6 and particularly preferably with 1 to 4 carbon atoms, eg. methyl, ethyl, n-propyl, isopropyl, n-butyl, sec-butyl, isobutyl, tert-butyl and n-decyl. Cycloalkyl has, for example, 3 to 8 C atoms, eg. cyclopropyl, cyclohexyl or cyclooctyl.

Aryl as part of the groups Z and $R^{12}$ to $R^{28}$, $R^{38}$ and $R^{39}$, ie. for example as part of arylalkyl or aryloxyalkyl, is, for example, α-naphthyl, β-naphthyl, phenanthrenyl and, preferably, phenyl.

Hetaryl as part of the groups Z and $R^{12}$ to $R^{28}$, $R^{38}$ and $R^{39}$, ie. for example as part of hetarylalkyl, hetaryloxyalkyl, hetarylalkenyl, is, for example, furyl, thienyl, pyrrolyl, isoxazolyl, isothiazolyl, oxazolyl, thiazolyl, 1,2,4-oxadiazolyl, 1,2,4-thiadiazolyl, 1,3,4-oxadiazolyl, 1,3,4-thiadiazolyl, imidazolyl, pyrazolyl, 1,2,4-triazolyl, pyridinyl, pyrimidinyl, pyridazinyl, pyrazinyl, 1,3,5-triazinyl, 1,2,4-triazinyl, benzoxazolyl, benzothiazolyl, quinolyl or isoquinolyl.

Accordingly, Z and $R^{12}$ to $R^{28}$, $R^{38}$ and $R^{39}$ is aralkyl, for example α-naphthylmethyl, 2-(β-naphthyl)ethyl and preferably phenylalkyl (especially benzyl, 1-phenylethyl, 2-phenylethyl, 3-phenylpropyl, 4-phenylbutyl and 6-phenylhexyl). Accordingly aryloxyalkyl is, for example, 4-phenoxybutyl, 3-phenoxypropyl, 2-(β-naphthoxy)ethyl and, in particular, 1-phenoxyethyl, 2-phenoxyethyl and phenoxymethyl.

Arylthioalkyl is, for example, phenylthiomethyl. Hetarylalkyl is, for example, hetarylmethyl or 2-hetarylethyl (especially 2- or 3- or 4-pyridinylethyl, 2- or 3- or 5- or 6-pyrazinylethyl, 2- or 4- or 5-thiazolylethyl, 2- or 4- or 5-oxazolylethyl, or 3-, 4- or 5-isoxazolylethyl).

Hetaryloxyalkyl is, for example, preferably hetaryloxymethyl and 2-(hetaryloxy)ethyl, for example 2-pyridinyloxymethyl or 2-(2-pyridinyloxy)ethyl.

Hetarylthioalkyl is, for example, preferably hetarylthiomethyl or 2-(hetarylthio)ethyl, eg. 2-thiazolylthiomethyl.

Alkenyl or alkynyl for Z and $R^{12}$ to $R^{28}$, $R^{38}$ and $R^{39}$ in compounds of the formula 1 is, as independent group or part of a group (eg. in alkenyloxy, hetarylalkenyl or arylalkynyl), straight-chain or branched with 2 to 10 carbon atoms, preferably with 2 to 6 carbon atoms and particularly preferably with 2 to 4 carbon atoms, eg. ethenyl, ethynyl, allyl, propargyl, 3-methyl-2-pentenyl or as alkenyl with more than one double bond, eg. 1,3-butadienyl and 4-methyl-1,3-pentadienyl. (Since alkenyl can in turn be substituted by alkenyl, Z or $R^{12}$ to $R^{28}$ or $R^{38}$ and $R^{39}$ can also be, for example, larger radicals, eg. 4,8-dimethyl-1,3,7-nonatrienyl.)

Aralkenyl is, for example, 2-(α-naphthyl)ethenyl or, particularly preferably, 2-phenylethenyl. Aryloxyalkenyl is, for example, 2-phenoxyethenyl. Arylthioalkenyl is, for example, 2-phenylthioethenyl. Hetarylalkenyl is, for example, 2-(3-isoxazolyl)ethenyl, 2-(2-thiazolyl)ethenyl or 2-(2-pyridyl)ethenyl. Aryloxyalkenyl is, for example, 2-(2-pyridyloxy)ethenyl.

Arylthioalkenyl is, for example, 2-(2-thiazolylthio)ethenyl. Arylalkynyl is, for example, preferably phenylethynyl. Hetarylalkynyl is, for example, (2-pyrimidinyl)ethynyl.

When acylamino is substituted, particularly suitable substituents are unsubstituted or substituted alkyl and aryl.

Particularly suitable substituents of which one or more (identical or different) may be present in Z and $R^{12}$ to $R^{28}$, $R^{38}$ and $R^{39}$, and they are preferably in the aryl and hetaryl radicals, are the following:

Halogen, hydroxyl, $C_1$–$C_6$-alkyl (especially methyl, ethyl, isopropyl and t-butyl), $C_2$–$C_6$-alkenyl (especially allyl and methallyl), $C_2$–$C_6$-alkynyl (especially propargyl), $C_1$–$C_6$-alkoxy (especially methoxy, ethoxy, isopropoxy, t-butoxy), $C_3$–$C_6$-alkenyloxy (especially allyloxy, methallyloxy, but preferably not substituents with an enol ether structure), $C_3$–$C_6$-alkynyloxy (especially propargyloxy, but preferably not substituents with an ynol ether structure), halo-$C_1$–$C_6$-alkyl (especially trifluoromethyl, trichloromethyl, chloromethyl and bromomethyl), halo-$C_1$–$C_6$-alkoxy (especially trifluoromethoxy), $C_1$–$C_6$-alkylthio (especially methylthio), hydroxy-$C_1$–$C_6$-alkyl (especially hydroxymethyl), $C_1$–$C_4$-alkoxy-$C_1$–$C_6$-alkyl (especially 2-methoxyethyl, 2-methoxypropyl, 3-methoxypropyl, 2-ethoxyethyl), $C_3$–$C_6$-cycloalkyl, $C_3$–$C_6$-cycloalkyl-$C_1$–$C_6$-alkyl (especially cyclopropylmethyl, cyclohexylmethyl), unsubstituted or substituted hydroxyiminoalkyl of the formula $R^{40}$—O—N=C($R^{41}$)— where $R^{40}$ is hydrogen, unsubstituted or substituted $C_1$–$C_{10}$-alkyl, unsubstituted or substituted $C_2$–$C_{10}$-alkenyl, unsubstituted or substituted $C_2$–$C_{10}$-alkynyl, unsubstituted or substituted aralkyl (especially unsubstituted or halogen-, $C_1$–$C_4$-alkyl-, trifluoromethyl- and/or $C_1$–$C_4$-alkoxy-substituted benzyl) and $R^{41}$ is hydrogen or $C_1$–$C_{10}$-alkyl; formyl, $C_2$–$C_{11}$-alkanoyl (especially acetyl, propionyl, isobutyryl and pivaloyl), iminoalkyl of the formula $R^{42}$—N=C($R^{43}$)— where $R^{42}$ is $C_1$–$C_{10}$-alkyl (especially isopropyl, tert-butyl) or unsubstituted or substituted phenyl or unsubstituted or substituted benzyl and $R^{43}$ is hydrogen or $C_1$–$C_{10}$-alkyl; cyano, thiocyanato, $C_1$–$C_8$-acyloxy (especially acetyloxy and unsubstituted or substituted benzoyloxy), nitro, unsubstituted or substituted aryl (especially unsubstituted or substituted phenyl); unsubstituted or substituted hetaryl (especially unsubstituted or substituted pyridinyl, pyrimidinyl, thiazolyl, oxazolyl and isoxazolyl), unsubstituted or substituted aryloxy (especially unsubstituted or substituted phenoxy), unsubstituted or substituted hetaryloxy (especially unsubstituted or substituted pyridinyloxy or pyrimidinyloxy), unsubstituted or substituted arylthio (especially unsubstituted or substituted phenylthio), unsubstituted or substituted hetarylthio (especially unsubstituted or substituted pyridinylthio, pyrimidinylthio or thiazolylthio), unsubstituted or substituted aryl-$C_1$–$C_4$-alkyl (especially unsubstituted or substituted benzyl), unsubstituted or substituted hetaryl-$C_1$–$C_4$-alkyl (especially unsubstituted or substituted pyridinyl-, pyrimidinyl-, thiazolyl-, oxazolyl- or isoxazolyl-substituted $C_1$–$C_4$-alkyl), unsubstituted or substituted aryl-$C_1$–$C_4$-alkoxy (especially unsubstituted or substituted benzyloxy), unsubstituted or substituted hetaryl-$C_1$–$C_4$-alkoxy (especially unsubstituted or substituted pyridinylmethyloxy, pyrimidinylmethyloxy, thiazolylmethyloxy, oxazolylmethyloxy or isoxazolylmethoxy), unsubstituted or substituted aryloxy-$C_1$–$C_4$-alkyl (especially unsubstituted or substituted phenoxymethyl, 1-phenoxyethyl or 2-phenoxyethyl), unsubstituted or substituted arylthio-$C_1$–$C_4$-alkyl (especially unsubstituted or substituted phenylthiomethyl), unsubstituted or substituted hetaryloxy-$C_1$–$C_4$-alkyl (especially pyridinyloxymethyl or pyrimidinyloxymethyl), unsubstituted or substituted hetarylthio-$C_1$–$C_4$-alkyl (especially pyridinylthiomethyl, pyrimidinylthiomethyl or thiazolylthiomethyl), —$NR^{44}R^{45}$, —$NR^{44}COR^{45}$, —$NHCONR^{44}R^{45}$, —$CONR^{44}R^{45}$, —$CH_2ON=CR^{44}R^{45}$, —$COOR^{44}$, —$OSO_2R^{44}$, —$SO_2R^{44}$, —$SO_2NR^{44}R^{45}$, —$NR^{44}SO_2R^{45}$, —$N=CR^{44}R^{45}$, where $R^{44}$ and $R^{45}$ are, independently of one another, hydrogen, $C_1$–$C_6$-alkyl, $C_3$–$C_6$-cycloalkyl, $C_3$–$C_6$-cycloalkyl-$C_1$–$C_4$-alkyl, unsubstituted or substituted aryl (especially unsubstituted or substituted phenyl) or unsubstituted or substituted aryl-$C_1$–$C_4$-alkyl (especially unsubstituted or substituted benzyl) and where unsubstituted or substituted aryl or hetaryl may carry the substituents mentioned above for aryl and hetaryl in Z, $R^{12}$ to $R^{28}$, $R^{38}$ and $R^{39}$.

Preferred groups Z, $R^{12}$ to $R^{28}$, $R^{38}$ and $R^{39}$ within this range are those whose number of carbon atoms does not exceed 28, irrespective of the type and number of any hetero atoms. Although compounds of the formula 1 in which Z, $R^{12}$ to $R^{28}$, $R^{38}$ and $R^{39}$ have larger numbers of carbons may still have biological, eg. fungicidal, activity, on occasion their effect or their practical application is prevented by excessive lipophilicity and/or insufficient solubility and/or particular difficulty in preparation.

Furthermore, compounds of the formula 1 which are particularly active and therefore preferred are those in which the total number of carbon atoms in Z, $R^{12}$ to $R^{28}$, $R^{38}$ and $R^{39}$ is more than 4, irrespective of the type and number of any hetero atoms. Compounds of the formula 1 where Z, $R^{12}$ to $R^{28}$, $R^{38}$ and $R^{39}$ have a smaller number of carbon atoms may, however, also have biological, eg. fungicidal, activity. On the other hand, such compounds of the formula 1 according to the invention are of particular interest not just because of their biological effect but much more because they can often be used particularly well as intermediates for synthesising other compounds of the formula 1 with even greater activity.

Examples of compounds of the formula 1 which are particularly preferred as intermediates are those in which Z is Cl Br, cyano, —SH, —NH$_2$, —CH$_3$, —C$_2$H$_5$, —CH$_2$Cl, —CH$_2$Br, CH$_2$OCH$_3$, —CH$_2$OH, -acetyl, —CH=CH$_2$, —C≡CH, —O—CH$_2$—CH=CH$_2$ and in which Z can also be CHO, OH or COOH if m is 1.

Such compounds of the formula 1 can be used to prepare, by building up the side chain Z, other compounds of the formula 1 which have even greater activity and in which, for example, the number of carbon atoms in Z is in the above-mentioned preferred range of from more than 4 to 28 C atoms.

The β-substituted cinnamic acid derivatives according to the invention can exist as E and Z isomers. The invention embraces both isomers, and isomers in which $R^1$—$X_m$— is trans relative to COY are preferred in principle. By the Cahn-Ingold-Prelog nomenclature (see, for example, J. March, "Advanced Organic Chemistry", 3rd edition, Wiley-Interscience, pp. 109 et seq.) these are the E isomers when m is 1 and the Z isomers when m is 0.

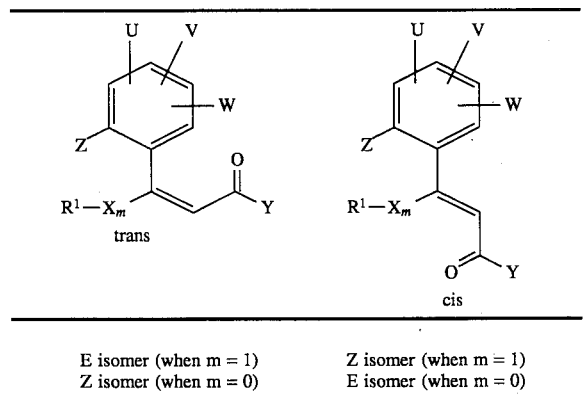

| E isomer (when m = 1) | Z isomer (when m = 1) |
| Z isomer (when m = 0) | E isomer (when m = 0) |

In the examples of the individual compounds (see Tables 1, 1a and 1b) for simplicity the isomers are called cis and trans with the above meanings.

The isomers can be separated by conventional processes such as crystallization or chromatography. The trans isomers are preferred for the uses according to the invention as fungicides, acaricides, insecticides or antimycotics. When the synthesis produces mixtures of isomers, separation is not absolutely necessary because in some cases the individual isomers are interconvertible when used according to the invention (for example as fungicides on land in the open), eg. due to the action of light, acids or bases, specifically also in vivo.

The present invention embraces both the individual isomers and mixtures thereof, and they are all biologically active.

The present invention comprises inter alia in particular compounds of the formula 1 where X is oxygen or sulfur and m is 0 or 1.

The present invention also comprises inter alia in particular those compounds of the formula 1 where $R^1$ is straight-chain or branched C$_1$–C$_4$-alkyl.

Particularly preferred compounds of the formula 1 are those where $R^1$—$X_m$— is methoxy, methyl or ethyl.

The present invention also comprises inter alia those compounds of the formula 1 where Y is OR$^4$ or NR$^7$R$^8$, and R$^4$, R$^7$ and R$^8$ have the meanings stated in the introduction, and preferred compounds are those where R$^4$, R$^7$ and R$^8$ are identical or different straight-chain or branched C$_1$–C$_4$-alkyl. Particularly preferred compounds of the formula 1 are those where Y is methoxy. These surprisingly have a particularly low toxicity for mammals.

The present invention also comprises inter alia those compounds of the formula 1 where U, V and W are identical or different fluorine, chlorine, bromine, iodine, cyano, nitro, trifluoromethyl, methyl, methoxy or, preferably, hydrogen.

The present invention also comprises inter alia those compounds of the formula 1 where Z is OR$^{12}$ or SR$^{13}$ and R$^{12}$ and R$^{13}$ can have the meanings stated above but are preferably unsubstituted or substituted aryl or unsubstituted or substituted five- or six-membered hetaryl with 1 to 3 hetero atoms (N, O, S).

The present invention also comprises inter alia in particular compounds of the formula 1a

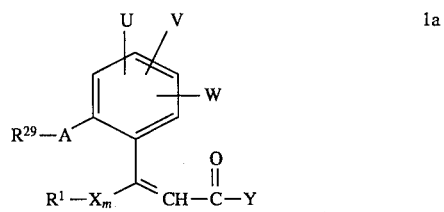

where U, V, W, $R^1$, $X_m$ and Y can have the meanings stated above, and —A— is —C=C—, —CR$^{30}$=CR$^{31}$—, —CHR$^{30}$—CHR$^{31}$—, —O—CHR$^{31}$—, —O—CO—, —NR$^{30}$CO—, —S—CHR$^{31}$—, —N=CR$^{31}$—, —COO—CHR$^{31}$, —O—N=CR$^{31}$—, —R$^{30}$C=N—O—CHR$^{31}$—, —CR$^{30}$=N—, —N=N— or —CHR$^{31}$—, where R$^{29}$ is unsubstituted or substituted alkyl, unsubstituted or substituted alkenyl, unsubstituted or substituted alkynyl, unsubstituted or substituted aralkyl, unsubstituted or substituted hetarylalkyl, unsubstituted or substituted aryloxyalkyl, unsubstituted or substituted hetaryloxyalkyl or hetarylthioalkyl and, preferably, unsubstituted or substituted aryl or unsubstituted or substituted hetaryl and R$^{30}$ and R$^{31}$ are identical or different straight-chain or branched C$_1$–C$_4$-alkyl or, preferably, hydrogen.

Where —A— contains a —C=C—, —C=N—, —N=C— or —N=N— double bond, the preferred isomers are those where R$^{29}$ is trans relative to the phenyl of the cinnamic acid.

The present invention also comprises in particular those compounds of the formula 1a where R$^{29}$ is five- or six-membered aryl or hetaryl which is unsubstituted or substituted one or more times by halogen, C$_1$–C$_{12}$-alkyl, C$_1$–C$_{12}$-haloalkyl, C$_2$–C$_{12}$-alkenyl, C$_2$–C$_{12}$-alkynyl, unsubstituted or substituted aryl, unsubstituted or substituted hetaryl, unsubstituted or substituted aralkyl, C$_1$–C$_{12}$-alkoxy, C$_1$–C$_{12}$-haloalkoxy, C$_2$–C$_{12}$-alkenyloxy, C$_2$–C$_{12}$-alkynyloxy, unsubstituted or substituted aryloxy, formyl, C$_1$–C$_{12}$-acyl, cyano, trifluoromethyl, nitro or —CR$^{32}$=N—OR$^{33}$ and/or may be fused to a benzene ring, where R$^{32}$ is hydrogen or C$_1$–C$_4$-alkyl and R$^{33}$ is hydrogen, C$_1$–C$_8$-alkyl, C$_2$–C$_8$-alkenyl or C$_2$–C$_8$-alkynyl.

Particularly preferred compounds of the formula 1a are those where R$^{29}$ is unsubstituted or singly or multiply halogen-, C$_1$–C$_{12}$-alkyl-, C$_2$–C$_{12}$-alkenyl-, unsubstituted or substituted aryl-, unsubstituted or substituted hetaryl-, unsubstituted or substituted aralkyl-, C$_1$–C$_{12}$-alkoxy-, C$_1$–C$_{12}$-haloalkoxy-, C$_2$–C$_{12}$-alkenyloxy-, C$_2$–C$_{12}$-alkynyloxy-, unsubstituted or substituted aryloxy-, formyl-, C$_1$–C$_{12}$-acyl-, cyano-, trifluoromethyl-, nitro- or —CR$^{32}$=NOR$^{33}$-substituted and/or possibly benzene-fused phenyl, furyl, thienyl, pyrrolyl, isoxazolyl, isothiazolyl, oxazolyl, thiazolyl, 1,2,4-oxadiazolyl, 1,2,4-thiadiazolyl, 1,3,4-oxadiazolyl, 1,3,4-thiadiazolyl, imidazolyl, pyrazolyl, 1,2,4-triazolyl, 1,3,4-triazolyl, pyridinyl, pyrimidinyl, pyridazinyl, pyrazinyl, 1,3,5-triazinyl or 1,2,4-triazinyl.

The present invention also comprises compounds of the formula 1a where U, V and W are identical or different fluorine, chlorine, bromine, iodine, cyano, nitro, trifluoromethyl, methyl or methoxy or, preferably, hydrogen.

The present invention also comprises preferably compounds of the formula 1a where $R^1$—$X_m$— is methoxy, methyl or ethyl.

The present invention also comprises compounds of the formula 1a where Y is $OR^4$ or $NR^7R^8$ and $R^4$, $R^7$ and $R^8$ are identical or different straight-chain or branched $C_1$–$C_4$-alkyl.

Particularly preferred compounds are those where Y is methoxy.

The present invention also comprises compounds of the formula 1b where Z and U are in adjacent positions on the phenyl ring

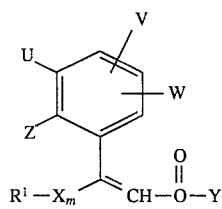

1b and form, together with the carbon atoms to which they are attached, an unsubstituted or substituted five- or six-membered aromatic ring which may contain one to three hetero atoms (N, O or S) and in which $R^1$, $X_m$, Y, V and W have the meanings stated above.

Preferred compounds of the formula 1b are those in which

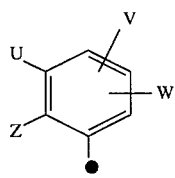

is one of the following:

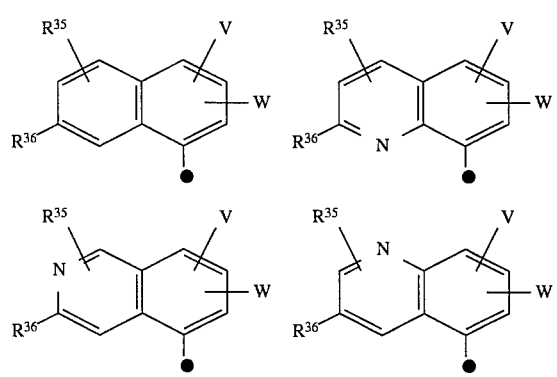

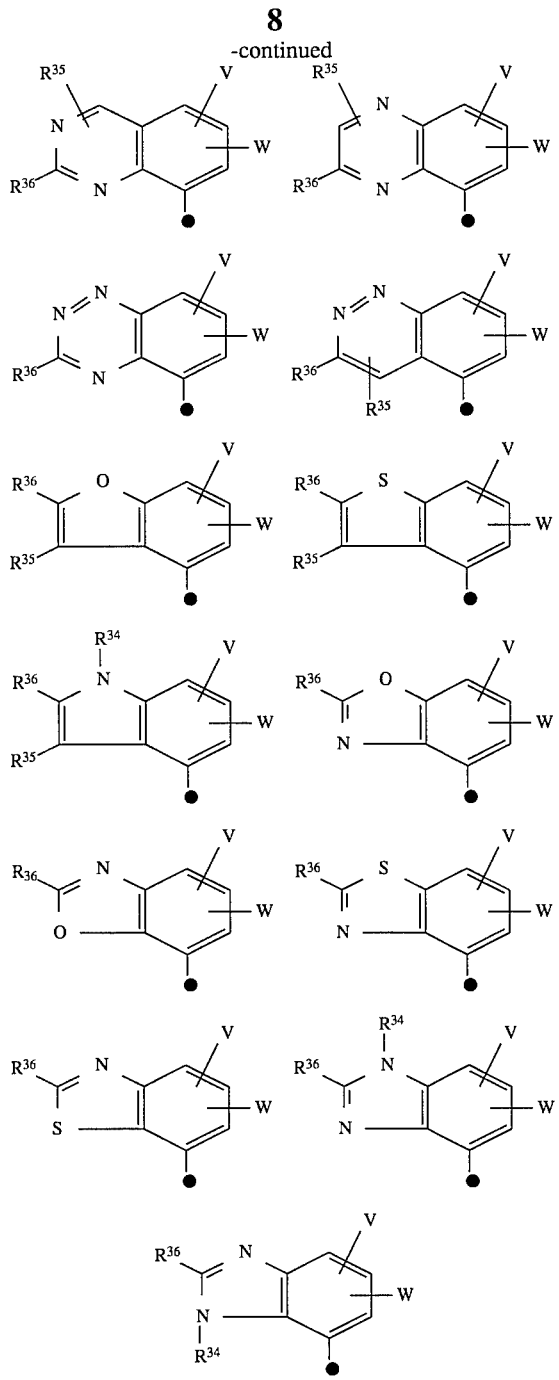

where $R^{36}$ has the meanings specified above for $R^{29}$ or is halogen (especially F, Cl Br) or is $OR^{12}$, $SR^{13}$ or $NR^{37}R^{38}$ where $R^{12}$, $R^{13}$, $R^{37}$ and $R^{38}$ have the meanings stated above, $R^{34}$ is hydrogen or $C_1$–$C_4$-alkyl, and $R^{35}$ is hydrogen, methyl, methoxy, trifluoromethyl, fluorine, chlorine, bromine, cyano or nitro.

Particularly preferred compounds of the formula 1b in turn are those where $R^{36}$ has the meanings specified above as particularly preferred for $R^{29}$.

The following Table 1 contains examples of compounds of the formula 1 according to the invention.

The following Table 1a contains examples of compounds of the formula 1a according to the invention.

Table 1b lists examples of compounds of the formula 1b according to the invention.

See above (page 9) for information on the identification of the isomers as trans or cis in the tables. The structural assignment was confirmed by X-ray structural analysis of the free acid (with Y=OH in place of methoxy) obtained from compound No. 1.1 in Table 1 by hydrolysis, and of compound No. 1a.310 in Table 1a. The assignment is easily made from the $^1$H NMR spectrum. The olefinic proton in position e to the group COY appears at a lower field in the trans isomers than in the cis isomers.

$^1$H NMR spectral data in the following tables relate to the olefinic proton in position α to the group COY; unless otherwise indicated, CDCl$_3$ was used as solvent.

TABLE 1

Compounds of the formula 1

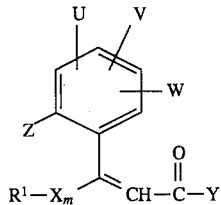

| Comp. no. | Z— | U,V,W | $R^1-X_m-$ | —Y | Isomer | m.p.; $^1$H—NMR (°C.) (ppm) |
|---|---|---|---|---|---|---|
| 1.1 | Methyl | H,H,H | Methoxy | Methoxy | trans | oil; 5.34 |
| 1.2 | Methyl | H,H,H | Methoxy | n-Butoxy | trans | |
| 1.3 | Chloromethyl | H,H,H | Methoxy | Methoxy | trans | |
| 1.4 | Bromomethyl | H,H,H | Methoxy | Methoxy | trans | 55–57; 5.41 |
| 1.5 | Formyl | H,H,H | Methoxy | Methoxy | trans | 56–58; 5.49 |
| 1.6 | HO—N=CH— | H,H,H | Methoxy | Methoxy | trans | |
| 1.7 | Methyl | H,H,H | Methoxy | Ethoxy | trans | |
| 1.8 | Methyl | H,H,H | Methoxy | N-Propoxy | trans | |
| 1.9 | Methyl | H,H,H | Methoxy | Iso-Propoxy | trans | |
| 1.10 | Hydroxy | H,H,H | Methoxy | Methoxy | trans | |
| 1.11 | Hydroxymethyl | H,H,H | Methoxy | Methoxy | trans | |
| 1.12 | HS— | H,H,H | Methoxy | Methoxy | trans | |
| 1.13 | Cl | H,H,H | Methoxy | Methoxy | trans | oil; 5.40 |
| 1.14 | Br | H,H,H | Methoxy | Methoxy | trans | oil; 5.37 |
| 1.15 | N≡C— | H,H,H | Methoxy | Methoxy | trans | |
| 1.16 | Ethyl | H,H,H | Methoxy | Methoxy | trans | |
| 1.17 | Ethenyl | H,H,H | Methoxy | Methoxy | trans | |
| 1.18 | Ethynyl | H,H,H | Methoxy | Methoxy | trans | |
| 1.19 | Allyl | H,H,H | Methoxy | Methoxy | trans | |
| 1.20 | Propargyl | H,H,H | Methoxy | Methoxy | trans | |
| 1.21 | Allyloxy | H,H,H | Methoxy | Methoxy | trans | |
| 1.22 | Acetyl | H,H,H | Methoxy | Methoxy | trans | |
| 1.23 | Amino | H,H,H | Methoxy | Methoxy | trans | |
| 1.24 | HO—CO— | H,H,H | Methoxy | Methoxy | trans | |
| 1.25 | Undec-1-en-1-yl | H,H,H | Methoxy | Methoxy | trans | |
| 1.26 | 4,8-Dimethyl-nona-1,3,7-trien-1-yl | H,H,H | Methoxy | Methoxy | trans | |
| 1.27 | 3-Phenyl-isoxazol-5-yl | H,H,H | Methoxy | Methoxy | trans | |
| 1.28 | 3-Heptyl-isoxazol-5-yl | H,H,H | Methoxy | Methoxy | trans | |
| 1.29 | 3-(1-Ethylpentyl)-isoxazol-5-yl | H,H,H | Methoxy | Methoxy | trans | |
| 1.30 | Phenyl | H,H,H | Methoxy | Methoxy | trans | |
| 1.31 | 2-Phenoxy-ethoxy | H,H,H | Methoxy | Methoxy | trans | |
| 1.32 | 3-(2,6-Difluorophenoxy)-prop-1-oxy | H,H,H | Methoxy | Methoxy | trans | |
| 1.33 | 4-(2-Cyanophenoxy)-but-1-oxy | H,H,H | Methoxy | Methoxy | trans | |
| 1.34 | 4-(3-Nitrophenoxy)-but-2-en-2-oxy | H,H,H | Methoxy | Methoxy | trans | |
| 1.35 | 5-(2-Methylphenoxy)-pent-1-en-1-yl | H,H,H | Methoxy | Methoxy | trans | |
| 1.36 | 4-Methylphenyl-sulfonyloxy-methyl | H,H,H | Methoxy | Methoxy | trans | |
| 1.37 | Methyl-sulfonyloxy-methyl | H,H,H | Methoxy | Methoxy | trans | |
| 1.38 | Methyl | H,H,H | Methyl | Methoxy | trans | oil; 6.01 |
| 1.39 | Methoxymethyl | H,H,H | Methyl | Methoxy | trans | oil; 6.01 |
| 1.40 | Bromomethyl | H,H,H | Methyl | Methoxy | trans | oil; 6.08 |
| 1.41 | Methyl | H,H,H | Ethyl | Methoxy | trans | |
| 1.42 | HO—N=CH— | H,H,H | Methyl | Methoxy | trans | |
| 1.43 | Br | H,H,H | Methyl | Methoxy | trans | |
| 1.44 | Methoxymethyl | H,H,H | iso-Propyl | Methoxy | trans | |
| 1.45 | Bromomethyl | H,H,H | iso-Propyl | Methoxy | trans | |
| 1.46 | Methoxymethyl | H,H,H | n-Hexyl | Methoxy | trans | |
| 1.47 | Methyl | H,H,H | Ethoxy | Methoxy | trans | oil; 5.32 |
| 1.48 | Methyl | H,H,H | Ethoxy | Methoxy | cis | oil; 5.07 |
| 1.49 | Bromomethyl | H,H,H | Ethoxy | Methoxy | trans | |
| 1.50 | Methoxymethyl | H,H,H | Ethoxy | Methoxy | trans | |
| 1.51 | Methyl | H,H,H | Ethoxy | Ethoxy | trans | oil; 5.32 |

TABLE 1-continued

Compounds of the formula 1

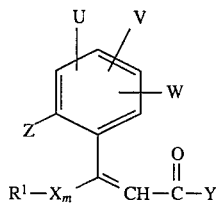

| Comp. no. | Z— | U,V,W | $R^1-X_m-$ | —Y | Isomer | m.p.; (°C.) | $^1H$—NMR (ppm) |
|---|---|---|---|---|---|---|---|
| 1.52 | Methyl | H,H,H | Ethoxy | n-Propoxy | trans | | |
| 1.53 | Methyl | H,H,H | n-Propoxy | Methoxy | trans | | |
| 1.54 | Formyl | H,H,H | Ethoxy | Methoxy | trans | | |
| 1.55 | 2,5-Dimethylbenzyloxy | H,H,H | Methoxy | Methoxy | trans | | |
| 1.56 | 2-Chlorobenzyloxy | H,H,H | Methoxy | Methoxy | trans | | |
| 1.57 | 3-Trifluoromethylbenzyloxy | H,H,H | Methoxy | Methoxy | trans | | |
| 1.58 | 4-Bromobenzyloxy | H,H,H | Methoxy | Methoxy | trans | | |
| 1.59 | 4-tert.-Butylbenzyloxy | H,H,H | Methoxy | Methoxy | trans | | |
| 1.60 | 4-Phenylbenzyloxy | H,H,H | Methoxy | Methoxy | trans | | |
| 1.61 | 3-Phenoxybenzyloxy | H,H,H | Methoxy | Methoxy | trans | | |
| 1.62 | 2,4-Dichlorobenzyloxy | H,H,H | Methoxy | Methoxy | trans | | |
| 1.63 | 4-Nitrobenzyloxy | H,H,H | Methoxy | Methoxy | trans | | |
| 1.64 | 3-Cyanobenzyloxy | H,H,H | Methoxy | Methoxy | trans | | |
| 1.65 | 2-Methyl-3-(4-tert.-butyl-phenyl)-propyl-benzoyloxy | H,H,H | Methoxy | Methoxy | trans | | |
| 1.66 | 4-Phenyl-benzoyloxy | H,H,H | Methoxy | Methoxy | trans | | |
| 1.67 | 4-tert.-Butylbenzoyloxy | H,H,H | Methoxy | Methoxy | trans | | |
| 1.68 | Benzoylamino | H,H,H | Methoxy | Methoxy | trans | | |
| 1.69 | 4-Phenylbenzoylamino | H,H,H | Methoxy | Methoxy | trans | | |
| 1.70 | 4-tert.-Butylbenzoylamino | H,H,H | Methoxy | Methoxy | trans | | |
| 1.71 | 2-(4-Fluorophenyl)-thiazol-4-ylmethyloxy | H,H,H | Methoxy | Methoxy | trans | 105–108; | 5.44 |
| 1.72 | 4-Phenylbenzyloxy | 4-Methyl | Methoxy | Methoxy | trans | | |
| 1.73 | 4-Phenylbenzyloxy | 4,6-Di-iso-Propyl | Methoxy | Methoxy | trans | | |
| 1.74 | 4-Phenylbenzyloxy | 4,6-Dimethyl | Methoxy | Methoxy | trans | | |
| 1.75 | 4-Phenylbenzyloxy | 4-Bromo | Methoxy | Methoxy | trans | | |
| 1.76 | 4-Phenylbenzyloxy | 4-Iodo | Methoxy | Methoxy | trans | | |
| 1.77 | 4-Phenylbenzyloxy | 4-Trifluoromethyl | Methoxy | Methoxy | trans | | |
| 1.78 | 4-Phenylbenzyloxy | 4-iso-Propyl | Methoxy | Methoxy | trans | | |
| 1.79 | 4-Phenylbenzyloxy | 4,6-Dichloro | Methbxy | Methoxy | trans | | |
| 1.80 | 4-Phenylbenzyloxy | 5-Methoxy | Methoxy | Methoxy | trans | | |
| 1.81 | 4-Phenylbenzyloxy | 3,5-Dimethyl | Methoxy | Methoxy | trans | | |
| 1.82 | 4-Phenylbenzyloxy | 3-Methoxy | Methoxy | Methoxy | trans | | |
| 1.83 | 4-Phenylbenzyloxy | 4,5-Dimethyl | Methoxy | Methoxy | trans | | |
| 1.84 | 4-Phenylbenzyloxy | 4-Methoxy | Methoxy | Methoxy | trans | | |
| 1.85 | 4-Phenylbenzyloxy | 6-Methyl-5-benzyloxy | Methoxy | Methoxy | trans | | |
| 1.86 | 4-Phenylbenzyloxy | 4-Fluor | Methoxy | Methoxy | trans | | |
| 1.87 | 4-Phenylbenzyloxy | 4-Ethyl | Methoxy | Methoxy | trans | | |
| 1.88 | 4-Phenylbenzyloxy | 5-Benzyloxy | Methoxy | Methoxy | trans | | |
| 1.89 | Phenoxy | H,H,H | Methoxy | Methoxy | trans | | |
| 1.90 | 3-Methylphenoxy | H,H,H | Methoxy | Methoxy | trans | oil; | 5.28 |
| 1.91 | 3-Methylphenoxy | H,H,H | Methoxy | Methoxy | cis | oil; | 5.21 |
| 1.92 | 2-Chlorophenoxy | H,H,H | Methoxy | Methoxy | trans | | |
| 1.93 | 4-Acetylphenoxy | H,H,H | Methoxy | Methoxy | trans | | |
| 1.94 | 3-Phenoxy-phenoxy | H,H,H | Methoxy | Methoxy | trans | | |
| 1.95 | 3-Methoxy-phenoxy | H,H,H | Methoxy | Methoxy | trans | oil; | 5.28 |
| 1.96 | 4-(4-Nitrobenzyloxy)phenoxy | H,H,H | Methoxy | Methoxy | trans | | |
| 1.97 | 2-Naphthyloxy | H,H,H | Methoxy | Methoxy | trans | | |
| 1.98 | 3-(Pyridin-2-yl)phenoxy | H,H,H | Methoxy | Methoxy | trans | | |
| 1.99 | 4-Phenoxymethyl-phenoxy | H,H,H | Methoxy | Methoxy | trans | | |
| 1.100 | 3-(Oxazol-2-yl)-phenoxy | H,H,H | Methoxy | Methoxy | trans | | |
| 1.101 | 4-(1,2,4-Triazol-1-yl)-phenoxy | H,H,H | Methoxy | Methoxy | trans | | |
| 1.102 | 2-Chloropyridin-4-yloxy | H,H,H | Methoxy | Methoxy | trans | | |
| 1.103 | Pyridin-2-yloxy | H,H,H | Methoxy | Methoxy | trans | | |
| 1.104 | 4-Methylpyridin-2-yloxy | H,H,H | Methoxy | Methoxy | trans | | |
| 1.105 | 4-Phenoxypyrimidin-2-yloxy | H,H,H | Methoxy | Methoxy | trans | | |
| 1.106 | 6-Phenoxy-pyrimidin-4-yloxy | H,H,H | Methoxy | Methoxy | trans | | |
| 1.107 | Quinolin-4-yloxy | H,H,H | Methoxy | Methoxy | trans | | |
| 1.108 | 5-Phenyl-1,3,4-oxadiazol-2-yloxy | H,H,H | Methoxy | Methoxy | trans | | |
| 1.109 | 2-Bromopyridin-3-yloxy | H,H,H | Methoxy | Methoxy | trans | | |
| 1.110 | Pyridin-3-yloxy | H,H,H | Methoxy | Methoxy | trans | | |
| 1.111 | 2-Chloropyridin-3-yloxy | H,H,H | Methoxy | Methoxy | trans | | |
| 1.112 | 4-Methyl-quinolin-2-yloxy | H,H,H | Methoxy | Methoxy | trans | | |

TABLE 1-continued

Compounds of the formula 1

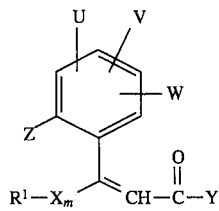

| Comp. no. | Z— | U,V,W | $R^1-X_m-$ | —Y | Isomer | m.p.; (°C.) | $^1H$—NMR (ppm) |
|---|---|---|---|---|---|---|---|
| 1.113 | 2-Methyl-quinolin-4-yloxy | H,H,H | Methoxy | Methoxy | trans | | |
| 1.114 | 5-Chloropyridin-3-yloxy | H,H,H | Methoxy | Methoxy | trans | | |
| 1.115 | 6-Methyl-2-nitro-pyridin-3-yloxy | H,H,H | Methoxy | Methoxy | trans | | |
| 1.116 | 4-Chloro-6-(2,6-difluorophenoxy)-1,3,5-triazin-2-yloxy | H,H,H | Methoxy | Methoxy | trans | | |
| 1.117 | 6-Phenylthio-pyridin-2-yloxy | H,H,H | Methoxy | Methoxy | trans | | |
| 1.118 | Phenylthio | H,H,H | Methoxy | Methoxy | trans | | |
| 1.119 | 2-Methyl-phenylthio | H,H,H | Methoxy | Methoxy | trans | | |
| 1.120 | 3-Phenoxy-phenylthio | H,H,H | Methoxy | Methoxy | trans | | |
| 1.121 | 1-Naphthylthio | H,H,H | Methoxy | Methoxy | trans | | |
| 1.122 | Pyridin-2-ylthio | H,H,H | Methoxy | Methoxy | trans | | |
| 1.123 | Pyridin-4-ylthio | H,H,H | Methoxy | Methoxy | trans | | |
| 1.124 | Benzthiazol-2-yl-thio | H,H,H | Methoxy | Methoxy | trans | | |
| 1.125 | Benzoxazol-2-ylthio | H,H,H | Methoxy | Methoxy | trans | | |
| 1.126 | Benzimidazol-2-ylthio | H,H,H | Methoxy | Methoxy | trans | | |
| 1.127 | Quinolin-2-ylthio | H,H,H | Methoxy | Methoxy | trans | | |
| 1.128 | 5-$CF_3$—Benzthiazol-2-ylthio | H,H,H | Methoxy | Methoxy | trans | | |
| 1.129 | 6-Methyl-benzthiazol-2-ylthio | H,H,H | Methoxy | Methoxy | trans | | |
| 1.130 | 6-Cl-Benzthiazol-2-yl-thio | H,H,H | Methoxy | Methoxy | trans | | |
| 1.131 | 5-Cl-Benzthiazol-2-yl-thio | H,H,H | Methoxy | Methoxy | trans | | |
| 1.132 | 6-Ethoxy-Benzthiazol-2-ylthio | H,H,H | Methoxy | Methoxy | trans | | |
| 1.133 | 7-$CF_3$—Quinolin-4-ylthio | H,H,H | Methoxy | Methoxy | trans | | |
| 1.134 | Pyrimidin-2-ylthio | H,H,H | Methoxy | Methoxy | trans | | |
| 1.135 | 1-Phenyl-1,2,3,4-tetrazol-5-ylthio | H,H,H | Methoxy | Methoxy | trans | | |
| 1.136 | N-Phenylamino | H,H,H | Methoxy | Methoxy | trans | | |
| 1.137 | N-Methyl, N-phenylamino | H,H,H | Methoxy | Methoxy | trans | | |
| 1.138 | N-Methyl, N-(3-chlorophenyl)-amino | H,H,H | Methoxy | Methoxy | trans | | |
| 1.139 | N-(3-Phenoxyphenyl)-amino | H,H,H | Methoxy | Methoxy | trans | | |
| 1.140 | N-(2,5-Dimethylbenzyl)-amino | H,H,H | Methoxy | Methoxy | trans | | |
| 1.141 | N-Methyl, N-(2-chlorobenzyl)-amino | H,H,H | Methoxy | Methoxy | trans | | |
| 1.142 | N-Acetyl-N-phenylamino | H,H,H | Methoxy | Methoxy | trans | | |
| 1.143 | Phenylsulfinyl | H,H,H | Methoxy | Methoxy | trans | | |
| 1.144 | 2-Methyl-phenylsulfinyl | H,H,H | Methoxy | Methoxy | trans | | |
| 1.145 | Naphthylsulfinyl | H,H,H | Methoxy | Methoxy | trans | | |
| 1.146 | Phenylsulfonyl | H,H,H | Methoxy | Methoxy | trans | | |
| 1.147 | Naphthylsulfonyl | H,H,H | Methoxy | Methoxy | trans | | |
| 1.148 | Quinolin-2-ylsulfonyl | H,H,H | Methoxy | Methoxy | trans | | |
| 1.149 | Benzoyloxymethyl | H,H,H | Methoxy | Methoxy | trans | | |
| 1.150 | 4-Acetylamino-benzoyloxymethyl | H,H,H | Methoxy | Methoxy | trans | | |
| 1.151 | 2-Chlorobenzoyloxymethyl | H,H,H | Methoxy | Methoxy | trans | | |
| 1.152 | 3-Cyanobenzoyloxymethyl | H,H,H | Methoxy | Methoxy | trans | | |
| 1.153 | 3-Phenoxybenzoyloxymethyl | H,H,H | Methoxy | Methoxy | trans | | |
| 1.154 | 4-Phenoxybenzoyloxymethyl | H,H,H | Methoxy | Methoxy | trans | | |
| 1.155 | n-Hexanoyloxymethyl | H,H,H | Methoxy | Methoxy | trans | | |
| 1.156 | 2-Pyridin-carbonyloxymethyl | H,H,H | Methoxy | Methoxy | trans | | |
| 1.157 | 2-Pyrazinyl-carbonyloxymethyl | H,H,H | Methoxy | Methoxy | trans | | |
| 1.158 | 2-Pyrazinyl-carbonyloxymethyl | H,H,H | Methoxy | Methoxy | trans | | |
| 1.159 | 4-Pyridazinyl-carbonyloxymethyl | H,H,H | Methoxy | Methoxy | trans | | |
| 1.160 | Phenylacetyloxymethyl | H,H,H | Methoxy | Methoxy | trans | | |
| 1.161 | Phenoxyacetyloxymethyl | H,H,H | Methoxy | Methoxy | trans | | |
| 1.162 | 2-Phenoxypropionyloxymethyl | H,H,H | Methoxy | Methoxy | trans | | |
| 1.163 | Cyclohexylcarbonyloxymethyl | H,H,H | Methoxy | Methoxy | trans | | |
| 1.164 | 4-(4-Carboxyphenoxy)-phenyl-carbonyloxymethyl | H,H,H | Methoxy | Methoxy | trans | | |
| 1.165 | Methoxymethyl | H,H,H | Methyl | Methoxy | cis | | oil; 5.82 |
| 1.166 | Methyl | H,H,H | Methyl | Methoxy | cis | | oil; 5.78 |
| 1.167 | Bromomethyl | H,H,H | Methyl | Methoxy | cis | | oil; 5.90 |
| 1.168 | Methyl | H,H,H | Methyl | —$NHCH_3$ | trans | | resin; 5.95 |
| 1.169 | Methyl | H,H,H | Methyl | —$NHCH_3$ | cis | | resin; 5.80 |
| 1.170 | Methoxymethyl | H,H,H | Methyl | Methoxy | trans | | oil; 6.01 |
| 1.171 | Bromomethyl | H,H,H | Methyl | Methoxy | trans | | oil; 6.08 |
| 1.172 | 4-Phenylbenzyloxy | 4,6-Difluoro | Methoxy | Methoxy | trans | | |
| 1.173 | 4-Phenylbenzyloxy | 4-Chloro | Methoxy | Methoxy | trans | | |

TABLE 1-continued

Compounds of the formula 1

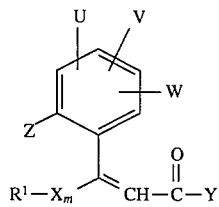

| Comp. no. | Z— | U,V,W | $R^1-X_m-$ | —Y | Isomer | m.p.; $^1$H—NMR (°C.) (ppm) |
|---|---|---|---|---|---|---|
| 1.174 | 3-Phenylphenoxy | H,H,H | Methoxy | Methoxy | trans | oil; 5.28 |
| 1.175 | 3-Phenylphenoxy | H,H,H | Methoxy | Methoxy | cis | oil; 5.23 |
| 1.176 | 4-Benzylphenoxy | H,H,H | Methoxy | Methoxy | trans | oil; 5.28 |
| 1.177 | 4-Benzylphenoxy | H,H,H | Methoxy | Methoxy | cis | oil; 5.18 |
| 1.178 | 2-Methylphenoxy | H,H,H | Methoxy | Methoxy | trans | oil; 5.32 |
| 1.179 | 2-Methylphenoxy | H,H,H | Methoxy | Methoxy | cis | oil; 5.25 |
| 1.180 | 4-Phenyl-butadien-1-yl | H,H,H | Methoxy | Methoxy | trans | 133–135; 5.43 |
| 1.181 | trans-3-(Biphenyl-4-yl)-2,2-dibromocycloprop-1-yl | H,H,H | Methoxy | Methoxy | trans | 33–36; 5.39 |
| 1.182 | trans-3-(Biphenyl-4-yl)-2,2-dichlorocycloprop-1-yl | H,H,H | Methoxy | Methoxy | trans | 44–48; 5.38 |
| 1.183 | 3,6,10-Trimethyl-undeca-1,3,5,9-tetraen-1-yl | H,H,H | Methoxy | Methoxy | trans | oil; 5.41 |

TABLE 1a

Compounds of the formula 1a

| Comp. no. | R²⁹— | —A— | U,V,W | R¹—Xₘ— | —Y | Isomer | m.p.; ¹H—NMR (°C.) (ppm) |
|---|---|---|---|---|---|---|---|
| 1a.1 | Phenyl | —OCH₂— | H,H,H | Methoxy | Methoxy | trans | oil; 5.37 |
| 1a.2 | 2-Methylphenyl | —OCH₂— | H,H,H | Methoxy | Methoxy | trans | |
| 1a.3 | 3-Trifluoromethylphenyl | —OCH₂— | H,H,H | Methoxy | Methoxy | trans | |
| 1a.4 | 4-Chlorophenyl | —OCH₂— | H,H,H | Methoxy | Methoxy | trans | |
| 1a.5 | 2,4-Dichlorophenyl | —OCH₂— | H,H,H | Methoxy | Methoxy | trans | |
| 1a.6 | 2,4,6-Trimethylphenyl | —OCH₂— | H,H,H | Methoxy | Methoxy | trans | |
| 1a.7 | 3-Cyanophenyl | —OCH₂— | H,H,H | Methoxy | Methoxy | trans | |
| 1a.8 | 2-Methyl-4-acetylphenyl | —OCH₂— | H,H,H | Methoxy | Methoxy | trans | |
| 1a.9 | 3-Formylphenyl | —OCH₂— | H,H,H | Methoxy | Methoxy | trans | |
| 1a.10 | 3-Acetylphenyl | —OCH₂— | H,H,H | Methoxy | Methoxy | trans | |
| 1a.11 | 2-Methyl-4-propionylphenyl | —OCH₂— | H,H,H | Methoxy | Methoxy | trans | |
| 1a.12 | 2-Methyl-4-isobutyroyl-phenyl | —OCH₂— | H,H,H | Methoxy | Methoxy | trans | |
| 1a.13 | 2-Methyl-4-butyroylphenyl | —OCH₂— | H,H,H | Methoxy | Methoxy | trans | |
| 1a.14 | 2,5-Dimethyl-4-acetylphenyl | —OCH₂— | H,H,H | Methoxy | Methoxy | trans | |
| 1a.15 | 2-Methyl-4-hexanoylphenyl | —OCH₂— | H,H,H | Methoxy | Methoxy | trans | |
| 1a.16 | 2-Methyl-4-benzoylphenyl | —OCH₂— | H,H,H | Methoxy | Methoxy | trans | |
| 1a.17 | 3-(Phenylamino)phenyl | —OCH₂— | H,H,H | Methoxy | Methoxy | trans | |
| 1a.18 | 4-Fluorophenyl | —OCH₂— | H,H,H | Methoxy | Methoxy | trans | |
| 1a.19 | 2-Bromophenyl | —OCH₂— | H,H,H | Methoxy | Methoxy | trans | |
| 1a.20 | 4-Nitrophenyl | —OCH₂— | H,H,H | Methoxy | Methoxy | trans | |
| 1a.21 | 2-Methyl-4-Chlorophenyl | —OCH₂— | H,H,H | Methoxy | Methoxy | trans | |
| 1a.22 | 4-Cyanophenyl | —OCH₂— | H,H,H | Methoxy | Methoxy | trans | |
| 1a.23 | 4-(Acetylamino)phenyl | —OCH₂— | H,H,H | Methoxy | Methoxy | trans | |
| 1a.24 | 3-(Benzoylamino)phenyl | —OCH₂— | H,H,H | Methoxy | Methoxy | trans | |
| 1a.25 | 3-Benzyloxyphenyl | —OCH₂— | H,H,H | Methoxy | Methoxy | trans | |
| 1a.26 | 4-Benzyloxyphenyl | —OCH₂— | H,H,H | Methoxy | Methoxy | trans | |
| 1a.27 | 4-tert.-Butylphenyl | —OCH₂— | H,H,H | Methoxy | Methoxy | trans | |
| 1a.28 | 4-Cyclohexylpenyl | —OCH₂— | H,H,H | Methoxy | Methoxy | trans | |
| 1a.29 | 4-Phenylphenyl | —OCH₂— | H,H,H | Methoxy | Methoxy | trans | |
| 1a.30 | 2-Chloro-4-phenoxyphenyl | —OCH₂— | H,H,H | Methoxy | Methoxy | trans | |
| 1a.31 | 4-Phenoxyphenyl | —OCH₂— | H,H,H | Methoxy | Methoxy | trans | oil; 5.39 |
| 1a.32 | 4-(4-Trifluoromethyl-phenoxy)-phenyl | —OCH₂— | H,H,H | Methoxy | Methoxy | trans | |
| 1a.33 | 3-Phenoxyphenyl | —OCH₂— | H,H,H | Methoxy | Methoxy | trans | |
| 1a.34 | 3-tert.-Butoxyphenyl | —OCH₂— | H,H,H | Methoxy | Methoxy | trans | |

TABLE 1a-continued

Compounds of the formula 1a

| Comp. no. | R29— | —A— | U,V,W | R1—Xm— | —Y | Isomer | m.p.; 1H—NMR (°C.) (ppm) |
|---|---|---|---|---|---|---|---|
| 1a.35 | 4-tert.-Butoxyphenyl | —OCH2— | H,H,H | Methoxy | Methoxy | trans | |
| 1a.36 | 4-Ethoxyphenyl | —OCH2— | H,H,H | Methoxy | Methoxy | trans | |
| 1a.37 | 4-n-Butoxyphenyl | —OCH2— | H,H,H | Methoxy | Methoxy | trans | oil; 5.37 |
| 1a.38 | 4-n-Hexyloxyphenyl | —OCH2— | H,H,H | Methoxy | Methoxy | trans | |
| 1a.39 | 4-(2-Ethylhexyloxy)-phenyl | —OCH2— | H,H,H | Methoxy | Methoxy | trans | |
| 1a.40 | 3-n-Decyloxyphenyl | —OCH2— | H,H,H | Methoxy | Methoxy | trans | |
| 1a.41 | 3-(Phenylsulfonylamino)-phenyl | —OCH2— | H,H,H | Methoxy | Methoxy | trans | |
| 1a.42 | 3-(Methylsulfinylamino)-phenyl | —OCH2— | H,H,H | Methoxy | Methoxy | trans | |
| 1a.43 | 4-Trifluoromethylsulfonylamino)-phenyl | —OCH2— | H,H,H | Methoxy | Methoxy | trans | |
| 1a.44 | 4-(Phenylsulfinylamino)-phenyl | —OCH2— | H,H,H | Methoxy | Methoxy | trans | |
| 1a.45 | 3-(Phenylaminosulfonyl)-phenyl | —OCH2— | H,H,H | Methoxy | Methoxy | trans | |
| 1a.46 | 4-(Methylaminosulfonyl)-phenyl | —OCH2— | H,H,H | Methoxy | Methoxy | trans | |
| 1a.47 | 3-(Phenoxycarbonyl)-phenyl | —OCH2— | H,H,H | Methoxy | Methoxy | trans | |
| 1a.48 | 3-(Benzyloxycarbonyl)-phenyl | —OCH2— | H,H,H | Methoxy | Methoxy | trans | |
| 1a.49 | 4-(Methoxycarbonyl)-phenyl | —OCH2— | H,H,H | Methoxy | Methoxy | trans | |
| 1a.50 | 4-(2-Chlorobenzyloxycarbonyl)-phenyl | —OCH2— | H,H,H | Methoxy | Methoxy | trans | |
| 1a.51 | 2-(Aminocarbonyl)-phenyl | —OCH2— | H,H,H | Methoxy | Methoxy | trans | |
| 1a.52 | 2-(Aminothiocarbonyl)-phenyl | —OCH2— | H,H,H | Methoxy | Methoxy | trans | |
| 1a.53 | 2-(Methylsulfinyloxy)-phenyl | —OCH2— | H,H,H | Methoxy | Methoxy | trans | |
| 1a.54 | 3-[(4-Methylphenyl)-sulfonyloxy]-phenyl | —OCH2— | H,H,H | Methoxy | Methoxy | trans | |
| 1a.55 | 4-(1,2,4-Triazol-1-yl)-phenyl | —OCH2— | H,H,H | Methoxy | Methoxy | trans | |
| 1a.56 | 4'-Hydroxybiphenyl-4-yl | —OCH2— | H,H,H | Methoxy | Methoxy | trans | |
| 1a.57 | 4-(4-Aminophenoxy)-phenyl | —OCH2— | H,H,H | Methoxy | Methoxy | trans | |
| 1a.58 | 4-(5-Chloro-2-pyridyl)-phenyl | —OCH2— | H,H,H | Methoxy | Methoxy | trans | |
| 1a.59 | 4-(5-Nitro-2-pyridyl)-phenyl | —OCH2— | H,H,H | Methoxy | Methoxy | trans | |
| 1a.60 | 2-CH3, 4-[(CH3)2CH—CH2—O—N=C(CH3)]—C6H3— | —OCH2— | H,H,H | Methoxy | Methoxy | trans | oil; 5.40 |
| 1a.61 | 2,5-(CH3)2-4-[CH3—O—N=C(CH3)]—C6H3— | —OCH2— | H,H,H | Methoxy | Methoxy | trans | oil; 5.42 |
| 1a.62 | 3-(CH3—O—N=CH)—C6H4— | —OCH2— | H,H,H | Methoxy | Methoxy | trans | oil; 5.39 |
| 1a.63 | 3-(CH2=CH—CH2—O—N=CH)—C6H4 | —OCH2— | H,H,H | Methoxy | Methoxy | trans | oil; 5.39 |
| 1a.64 | 3-(2-Chlorobenzyloximinomethyl)-phenyl | —OCH2— | H,H,H | Methoxy | Methoxy | trans | resin; 5.36 |
| 1a.65 | 4-(Benzyloximinomethyl)-phenyl | —OCH2— | H,H,H | Methoxy | Methoxy | trans | |
| 1a.66 | 2-CH3, 4-[Benzyl-O—N=C(CH3)]—C6H3— | —OCH2— | H,H,H | Methoxy | Methoxy | trans | |
| 1a.67 | 2-CH3, 4-[Isopentyl-O—N=C(CH3)]—C6H3— | —OCH2— | H,H,H | Methoxy | Methoxy | trans | |
| 1a.68 | 2-CH3, 4-[Geranyl-O—N=C(CH3)]C6H3— | —OCH2— | H,H,H | Methoxy | Methoxy | trans | |
| 1a.69 | 2-CH3, 4-[CH3O—N=C(C6H5)]—C6H3— | —OCH2— | H,H,H | Methoxy | Methoxy | trans | |
| 1a.70 | 2-CH3, 4-[CH2=C(CH3)—CH2—O—N=C(C2H5)]—C6H3— | —OCH2— | H,H,H | Methoxy | Methoxy | trans | |
| 1a.71 | 2-CH3, 4-[Cl—CH=CH—CH2—O—N=C(CH3)]—C6H3— | —OCH2— | H,H,H | Methoxy | Methoxy | trans | |

TABLE 1a-continued

Compounds of the formula 1a $$R^{29}-A\underset{R^1-X_m}{\overset{U\quad V}{\underset{}{\bigcirc}}}\overset{W}{\underset{CH-C-Y}{\overset{O}{\|}}}\quad 1a$$

| Comp. no. | R²⁹— | —A— | U,V,W | R¹—Xₘ— | —Y | Isomer | m.p.; ¹H—NMR (°C.) (ppm) |
|---|---|---|---|---|---|---|---|
| 1a.72 | 2-CH₃—4-[CH₃—O—N=C(CH₃)]—C₆H₃ | —OCH₂— | H,H,H | Methoxy | Methoxy | trans | 58–60; 5.38 |
| 1a.73 | 2-CH₃—4-[CH₃—O—N=C(CH₃)]—C₆H₃ | —OCH₂— | H,H,H | Methoxy | n-Pentyloxy | trans | 154; 5.32 |
| 1a.74 | 2-CH₃—4-[CH₃—O—N=C(CH₃)]—C₆H₃ | —OCH₂— | H,H,H | Methoxy | Ethoxy | trans | oil; 5.37 |
| 1a.75 | 2-CH₃—4-[CH₃—O—N=C(CH₃)]—C₆H₃ | —OCH₂— | H,H,H | Methoxy | n-Propoxy | trans | oil; 5.38 |
| 1a.76 | 2-CH₃—4-[CH₃—O—N=C(CH₃)]—C₆H₃ | —OCH₂— | H,H,H | Methoxy | Isopropoxy | trans | |
| 1a.77 | 2-CH₃—4-[CH₃—O—N=C(CH₃)]—C₆H₃ | —OCH₂— | H,H,H | Methoxy | n-Butoxy | trans | oil; 5.37 |
| 1a.78 | 2-CH₃—4-[CH₃—O—N=C(CH₃)]—C₆H₃ | —OCH₂— | H,H,H | Methoxy | tert.-Butoxy | trans | |
| 1a.79 | 2-CH₃—4-[CH₃—O—N=C(CH₃)]—C₆H₃ | —OCH₂— | H,H,H | Methoxy | n-Hexyloxy | trans | |
| 1a.80 | 2-CH₃—4-[CH₃—O—N=C(CH₃)]—C₆H₃ | —OCH₂— | H,H,H | Methoxy | Cyclohexyloxy | trans | |
| 1a.81 | 2-CH₃—4-[CH₃—O—N=C(CH₃)]—C₆H₃ | —OCH₂— | H,H,H | Methoxy | Cyclopropyl-methyloxy | trans | |
| 1a.82 | 2-CH₃—4-[CH₃—O—N=C(CH₃)]—C₆H₃ | —OCH₂— | H,H,H | Methoxy | —ON=CH(CH₃)₂ | trans | oil; 5.47 |
| 1a.83 | 2-CH₃—4-[CH₃—O—N=C(CH₃)]—C₆H₃ | —OCH₂— | H,H,H | Methoxy | Allyloxy | trans | oil; 5.41 |
| 1a.84 | 2-CH₃—4-[CH₃—O—N=C(CH₃)]—C₆H₃ | —OCH₂— | H,H,H | Methoxy | Propargyloxy | trans | oil; 5.42 |
| 1a.85 | 2-CH₃—4-[CH₃—O—N=C(CH₃)]—C₆H₃ | —OCH₂— | H,H,H | Methoxy | 2-Methoxy-ethoxy | trans | |
| 1a.86 | 2-CH₃—4-[CH₃—O—N=C(CH₃)]—C₆H₃ | —OCH₂— | H,H,H | Methoxy | Methylthio | trans | oil; 5.72 |
| 1a.87 | 2-CH₃—4-[CH₃—O—N=C(CH₃)]—C₆H₃ | —OCH₂— | H,H,H | Methoxy | Ethylthio | trans | |
| 1a.88 | 2-CH₃—4-[CH₃—O—N=C(CH₃)]—C₆H₃ | —OCH₂— | H,H,H | Methoxy | Amino | trans | 97–99; 5.35 |
| 1a.89 | 2-CH₃—4-[CH₃—O—N=C(CH₃)]—C₆H₃ | —OCH₂— | H,H,H | Methoxy | Methylamino | trans | oil; 5.35 |
| 1a.90 | 2-CH₃—4-[CH₃—O—N=C(CH₃)]—C₆H₃ | —OCH₂— | H,H,H | Methoxy | Allylamino | trans | |
| 1a.91 | 2-CH₃—4-[CH₃—O—N=C(CH₃)]—C₆H₃ | —OCH₂— | H,H,H | Methoxy | Ethylamino | trans | 57–60; 5.37 |
| 1a.92 | 2-CH₃—4-[CH₃—O—N=C(CH₃)]—C₆H₃ | —OCH₂— | H,H,H | Methoxy | n-Propylamino | trans | |
| 1a.93 | 2-CH₃—4-[CH₃—O—N=C(CH₃)]—C₆H₃ | —OCH₂— | H,H,H | Methoxy | Isopropyl-amino | trans | |
| 1a.94 | 2-CH₃—4-[CH₃—O—N=C(CH₃)]—C₆H₃ | —OCH₂— | H,H,H | Methoxy | n-Butlyamino | trans | |
| 1a.95 | 2-CH₃—4-[CH₃—O—N=C(CH₃)]—C₆H₃ | —OCH₂— | H,H,H | Methoxy | iso-Butyl-amino | trans | |
| 1a.96 | 2-CH₃—4-[CH₃—O—N=C(CH₃)]—C₆H₃ | —OCH₂— | H,H,H | Methoxy | tert.-Butyl-amino | trans | |
| 1a.97 | 2-CH₃—4-[CH₃—O—N=C(CH₃)]—C₆H₃ | —OCH₂— | H,H,H | Methoxy | n-Hexylamino | trans | |
| 1a.98 | 2-CH₃—4-[CH₃—O—N=C(CH₃)]—C₆H₃ | —OCH₂— | H,H,H | Methoxy | Dimethylamino | trans | oil; 5.51 |
| 1a.99 | 2-CH₃—4-[CH₃—O—N=C(CH₃)]—C₆H₃ | —OCH₂— | H,H,H | Methoxy | Diethylamino | trans | |
| 1a.100 | 2-CH₃—4-[CH₃—O—N=C(CH₃)]—C₆H₃ | —OCH₂— | H,H,H | Methoxy | N-Methyl-N-ethylamino | trans | |
| 1a.101 | 2-CH₃—4-[CH₃—O—N=C(CH₃)]—C₆H₃ | —OCH₂— | H,H,H | Methoxy | N-Methyl-N-butylamino | trans | oil; 5.50; 5.58 (C—N rotamers) |

TABLE 1a-continued

Compounds of the formula 1a

| Comp. no. | R²⁹— | —A— | U,V,W | R¹—Xₘ— | —Y | Isomer | m.p.; ¹H—NMR (°C.) (ppm) |
|---|---|---|---|---|---|---|---|
| 1a.102 | 2-CH₃—4-[CH₃—O—N=C(CH₃)]—C₆H₃— | —OCH₂— | H,H,H | Methoxy | N-Methyl-N-cyclohexyalmino | trans | |
| 1a.103 | 2-CH₃—4-[CH₃—O—N=C(CH₃)]—C₆H₃— | —OCH₂— | H,H,H | Methoxy | Cyclopropyl-methylamino | trans | |
| 1a.104 | 2-CH₃—4-[CH₃—O—N=C(CH₃)]—C₆H₃— | —OCH₂— | H,H,H | Methoxy | —NHOH | trans | |
| 1a.105 | 2-CH₃—4-[CH₃—O—N=C(CH₃)]—C₆H₃— | —OCH₂— | H,H,H | Methoxy | —N(CH₃)OH | trans | |
| 1a.106 | 2-CH₃—4-[CH₃—O—N=C(CH₃)]—C₆H₃— | —OCH₂— | H,H,H | Methoxy | —NHOCH₃ | trans | |
| 1a.107 | 2-CH₃—4-[CH₃—O—N=C(CH₃)]—C₆H₃— | —OCH₂— | H,H,H | Methoxy | —N(CH₃)OCH₃ | trans | |
| 1a.108 | 2-Methylphenyl | —OCH₂— | H,H,H | Methyl | Methoxy | trans | oil; 5.98 |
| 1a.109 | 2-Methylphenyl | —OCH₂— | H,H,H | Methyl | Methoxy | cis | oil; 5.85 |
| 1a.110 | 2-Methylphenyl | —OCH₂— | H,H,H | Ethyl | Methoxy | trans | oil; 5.98 |
| 1a.111 | 2-Methylphenyl | —OCH₂— | H,H,H | Ethyl | Methoxy | cis | oil; 5.80 |
| 1a.112 | 2-CH₃—4-[CH₃—O—N=C(CH₃)]—C₆H₃— | —OCH₂— | H,H,H | Methyl | Methoxy | trans | oil; 6.00 |
| 1a.113 | 2-CH₃—4-[CH₃—O—N=C(CH₃)]—C₆H₃— | —OCH₂— | H,H,H | Methyl | Methoxy | cis | oil; 5.85 |
| 1a.114 | 2-CH₃—4-[CH₃—O—N=C(CH₃)]—C₆H₃— | —OCH₂— | H,H,H | Ethyl | Methoxy | trans | |
| 1a.115 | 2-CH₃—4-[CH₃—O—N=C(CH₃)]—C₆H₃— | —OCH₂— | H,H,H | Ethyl | Methoxy | cis | |
| 1a.116 | 2-CH₃—4-[CH₃—O—N=C(CH₃)]—C₆H₃— | —OCH₂— | H,H,H | n-Propyl | Methoxy | trans | |
| 1a.117 | 2-CH₃—4-[CH₃—O—N=C(CH₃)]—C₆H₃— | —OCH₂— | H,H,H | iso-Propyl | Methoxy | cis | |
| 1a.118 | 2-CH₃—4-[CH₃—O—N=C(CH₃)]—C₆H₃— | —OCH₂— | H,H,H | Ethoxy | Methoxy | trans | |
| 1a.119 | 2-CH₃—4-[CH₃—O—N=C(CH₃)]—C₆H₃— | —OCH₂— | H,H,H | n-Propoxy | Methoxy | trans | |
| 1a.120 | 2-CH₃—4-[CH₃—O—N=C(CH₃)]—C₆H₃— | —OCH₂— | H,H,H | i-Propoxy | Methoxy | trans | |
| 1a.121 | 2-CH₃—4-[CH₃—O—N=C(CH₃)]—C₆H₃— | —OCH₂— | H,H,H | n-Butoxy | Methoxy | trans | |
| 1a.122 | 2-CH₃—4-[CH₃—O—N=C(CH₃)]—C₆H₃— | —OCH₂— | H,H,H | n-Hexyloxy | Methoxy | trans | |
| 1a.123 | 2-CH₃—4-[CH₃—O—N=C(CH₃)]—C₆H₃— | —OCH₂— | H,H,H | Methylthio | Methoxy | trans | |
| 1a.124 | 2-CH₃—4-[CH₃—O—N=C(CH₃)]—C₆H₃— | —OCH₂— | H,H,H | Ethylthio | Methoxy | trans | |
| 1a.125 | 2-CH₃—4-[CH₃—O—N=C(CH₃)]—C₆H₃— | —OCH₂— | H,H,H | n-Propylthio | Methoxy | trans | |
| 1a.126 | 2-CH₃—4-[CH₃—O—N=C(CH₃)]—C₆H₃— | —OCH₂— | H,H,H | Methylamino | Methoxy | trans | |
| 1a.127 | 2-CH₃—4-[CH₃—O—N=C(CH₃)]—C₆H₃— | —OCH₂— | H,H,H | Diethylamino | Methoxy | trans | |
| 1a.128 | 2-CH₃—4-[CH₃—O—N=C(CH₃)]—C₆H₃— | —OCH₂— | H,H,H | Methoxyamino | Methoxy | trans | |
| 1a.129 | 2-CH₃—4-[CH₃—O—N=C(CH₃)]—C₆H₃— | —OCH₂— | H,H,H | Methyl | Cl | trans | |
| 1a.130 | 2-CH₃—4-[CH₃—O—N=C(CH₃)]—C₆H₃— | —OCH₂— | H,H,H | Methyl | iso-Butoxy | trans | |
| 1a.131 | 2-CH₃—4-[CH₃—O—N=C(CH₃)]—C₆H₃— | —OCH₂— | H,H,H | Methyl | Methylthio | trans | |
| 1a.132 | 2-CH₃—4-[CH₃—O—N=C(CH₃)]—C₆H₃— | —OCH₂— | H,H,H | Methyl | Amino | trans | |
| 1a.133 | 2-CH₃—4-[CH₃—O—N=C(CH₃)]—C₆H₃— | —OCH₂— | H,H,H | Methyl | Methylamino | trans | |
| 1a.134 | 2-CH₃—4-[CH₃—O—N=C(CH₃)]—C₆H₃— | —OCH₂— | H,H,H | Methyl | Dimethylamino | trans | |
| 1a.135 | 2-CH₃—4-[CH₃—O—N=C(CH₃)]—C₆H₃— | —OCH₂— | H,H,H | Methyl | —N(CH₃)OCH₃ | trans | |
| 1a.136 | 2-CH₃—4-[CH₃—O—N=C(CH₃)]—C₆H₃— | —OCH₂— | H,H,H | Methyl | —NHOCH₃ | trans | |

TABLE 1a-continued

Compounds of the formula 1a

| Comp. no. | R²⁹— | —A— | U,V,W | R¹—Xₘ— | —Y | Isomer | m.p.; ¹H—NMR (°C.) (ppm) |
|---|---|---|---|---|---|---|---|
| 1a.137 | 2-CH₃—, 4-[CH₃—O—N=C(CH₃)]—C₆H₃— | —OCH₂— | H,H,H | Methyl | n-Propoxy | trans | |
| 1a.138 | 2-CH₃—, 4-[CH₃—O—N=C(CH₃)]—C₆H₃— | —OCH₂— | H,H,H | Methyl | i-Propoxy | trans | |
| 1a.139 | 2-CH₃—, 4-[CH₃—O—N=C(CH₃)]—C₆H₃— | —OCH₂— | H,H,H | Methyl | n-Butoxy | trans | |
| 1a.140 | 2-CH₃—, 4-[CH₃—O—N=C(CH₃)]—C₆H₃— | —OCH₂— | H,H,H | Methyl | sec.-Butoxy | trans | |
| 1a.141 | 2-CH₃—, 4-[CH₃—O—N=C(CH₃)]—C₆H₃— | —OCH₂— | H,H,H | Methyl | n-Hexyloxy | trans | |
| 1a.142 | 2-CH₃—, 4-[CH₃—O—N=C(CH₃)]—C₆H₃— | —OCH₂— | H,H,H | Methyl | Diethylamino | trans | |
| 1a.143 | 2-CH₃—, 4-[CH₃—O—N=C(CH₃)]—C₆H₃— | —OCH₂— | H,H,H | Methyl | i-Propylamino | trans | |
| 1a.144 | 2-CH₃—, 4-[CH₃—O—N=C(CH₃)]—C₆H₃— | —OCH₂— | 4-Ethoxy | Methoxy | Methoxy | trans | |
| 1a.145 | 2-CH₃—, 4-[CH₃—O—N=C(CH₃)]—C₆H₃— | —OCH₂— | 4-Methoxy | Methoxy | Methoxy | trans | |
| 1a.146 | 2-CH₃—, 4-[CH₃—O—N=C(CH₃)]—C₆H₃— | —OCH₂— | 4-t-Butyl | Methoxy | Methoxy | trans | |
| 1a.147 | 2-CH₃—, 4-[CH₃—O—N=C(CH₃)]—C₆H₃— | —OCH₂— | 4-Fluoro | Methoxy | Methoxy | trans | |
| 1a.148 | 2-CH₃—, 4-[CH₃—O—N=C(CH₃)]—C₆H₃— | —OCH₂— | 6-Methyl | Methoxy | Methoxy | trans | |
| 1a.149 | 2-CH₃—, 4-[CH₃—O—N=C(CH₃)]—C₆H₃— | —OCH₂— | 5-CN | Methoxy | Methoxy | trans | |
| 1a.150 | 2-CH₃—, 4-[CH₃—O—N=C(CH₃)]—C₆H₃— | —OCH₂— | 5-NO₂ | Methoxy | Methoxy | trans | |
| 1a.151 | 2-CH₃—, 4-[CH₃—O—N=C(CH₃)]—C₆H₃— | —OCH₂— | 5-F | Methoxy | Methoxy | trans | |
| 1a.152 | 2-CH₃—, 4-[CH₃—O—N=C(CH₃)]—C₆H₃— | —OCH₂— | 5-Br | Methoxy | Methoxy | trans | |
| 1a.153 | 2-CH₃—, 4-[CH₃—O—N=C(CH₃)]—O—C₆H₃— | —OCH₂— | 5-I | Methoxy | Methoxy | trans | |
| 1a.154 | Phenyl | —SCH₂— | H,H,H | Methoxy | Methoxy | trans | |
| 1a.155 | 2-Methyl-, 4-tert.-butylphenyl | —SCH₂— | H,H,H | Methoxy | Methoxy | trans | |
| 1a.156 | Benzyl | —SCH₂— | H,H,H | Methoxy | Methoxy | trans | |
| 1a.157 | 4-Phenylbenzyl | —SCH₂— | H,H,H | Methoxy | Methoxy | trans | |
| 1a.158 | 2-Phenylethyl | —SCH₂— | H,H,H | Methoxy | Methoxy | trans | |
| 1a.159 | 4-Phenoxybutyl | —SCH₂— | H,H,H | Methoxy | Methoxy | trans | |
| 1a.160 | n-Octyl | —SCH₂— | H,H,H | Methoxy | Methoxy | trans | |
| 1a.161 | Geranyl | —SCH₂— | H,H,H | Methoxy | Methoxy | trans | resin; 5.36 |
| 1a.162 | 4-Phenyl-thiazol-2-yl | —SCH₂— | H,H,H | Methoxy | Methoxy | trans | |
| 1a.163 | Pyridin-2-yl | —SCH₂— | H,H,H | Methoxy | Methoxy | trans | |
| 1a.164 | Pyridin-4-yl | —SCH₂— | H,H,H | Methoxy | Methoxy | trans | |
| 1a.165 | 2,3,5,6-Tetrachlorpyridin-4-yl | —SCH₂— | H,H,H | Methoxy | Methoxy | trans | oil; 5.38 |
| 1a.166 | Benzoxazol-2-yl | —SCH₂— | H,H,H | Methoxy | Methoxy | trans | oil; 5.38 |
| 1a.167 | Benzothiazol-2-yl | —SCH₂— | H,H,H | Methoxy | Methoxy | trans | oil; 5.40 |
| 1a.168 | 5-Chloro-benzothiazol-2-yl | —SCH₂— | H,H,H | Methoxy | Methoxy | trans | oil; 5.40 |
| 1a.169 | 6-Chloro-benzothiazol-2-yl | —SCH₂— | H,H,H | Methoxy | Methoxy | trans | 85–88; 5.41 |
| 1a.170 | 5-CF₃—Benzothiazol-2-yl | —SCH₂— | H,H,H | Methoxy | Methoxy | trans | oil; 5.39 |
| 1a.171 | 6-OEt-benzothiazol-2-yl | —SCH₂— | H,H,H | Methoxy | Methoxy | trans | oil; 5.40 |
| 1a.172 | 5-CF₃—Pyridin-2-yl | —SCH₂— | H,H,H | Methoxy | Methoxy | trans | 178; 5.42 |
| 1a.173 | 3-Cyano-, 4-CF₃—, 6-(2-thienyl)- | —SCH₂— | H,H,H | Methoxy | Methoxy | trans | |

TABLE 1a-continued

Compounds of the formula 1a

| Comp. no. | R29— | —A— | U,V,W | R1—Xm— | —Y | Isomer | m.p.; 1H—NMR (°C.) (ppm) |
|---|---|---|---|---|---|---|---|
| | pyridin-2-yl | | | | | | |
| 1a.174 | Benzimidazol-2-yl | —SCH2— | H,H,H | Methoxy | Methoxy | trans | oil; 5.46 |
| 1a.175 | 4-Methylpyrimidin-2-yl | —SCH2— | H,H,H | Methoxy | Methoxy | trans | |
| 1a.176 | Quinolin-2-yl | —SCH2— | H,H,H | Methoxy | Methoxy | trans | oil; 5.37 |
| 1a.177 | Quinolin-8-yl | —SCH2— | H,H,H | Methoxy | Methoxy | trans | |
| 1a.178 | 7-Trifluoromethyl-quinolin-4-yl | —SCH2— | H,H,H | Methoxy | Methoxy | trans | |
| 1a.179 | 3-Phenyl-1,2,4-triazol-5-yl | —SCH2— | H,H,H | Methoxy | Methoxy | trans | |
| 1a.180 | 5-Phenyl-1,3,4-oxadizol-2-yl | —SCH2— | H,H,H | Methoxy | Methoxy | trans | oil; 5.40 |
| 1a.181 | 4-Phenylthiazol-2-yl | —OCH2— | H,H,H | Methoxy | Methoxy | trans | oil; 5.38 |
| 1a.182 | 5-Methyl-2-phenylthiazol-4-yl | —OCH2— | H,H,H | Methoxy | Methoxy | trans | oil; 5.36 |
| 1a.183 | 4-Chloropyrazole | —OCH2— | H,H,H | Methoxy | Methoxy | trans | |
| 1a.184 | Benzotriazol-1-yl | —OCH2— | H,H,H | Methoxy | Methoxy | trans | |
| 1a.185 | 2-Methyl-quinolin-8-yl | —OCH2— | H,H,H | Methoxy | Methoxy | trans | |
| 1a.186 | Quinoxalin-2-yl | —OCH2— | H,H,H | Methoxy | Methoxy | trans | |
| 1a.187 | Dibenzofuran-2-yl | —OCH2— | H,H,H | Methoxy | Methoxy | trans | |
| 1a.188 | 5,6-Diphenyl-1,2,4-triazin-3-yl | —OCH2— | H,H,H | Methoxy | Methoxy | trans | |
| 1a.189 | Pyridin-2-yl | —OCH2— | H,H,H | Methoxy | Methoxy | trans | |
| 1a.190 | Pyridin-3-yl | —OCH2— | H,H,H | Methoxy | Methoxy | trans | |
| 1a.191 | Pyridin-4-yl | —OCH2— | H,H,H | Methoxy | Methoxy | trans | |
| 1a.192 | Pyrimidin-2-yl | —OCH2— | H,H,H | Methoxy | Methoxy | trans | |
| 1a.193 | Pyrimidin-4-yl | —OCH2— | H,H,H | Methoxy | Methoxy | trans | |
| 1a.194 | Pyrimidin-5-yl | —OCH2— | H,H,H | Methoxy | Methoxy | trans | |
| 1a.195 | Thiazolol[5,4-b]pyridin-2-yl | —SCH2— | H,H,H | Methoxy | Methoxy | trans | 86–89, 5.40 |
| 1a.196 | 5-Chloro-thiazolo[5,4-b]-pyridin-2-yl | —SCH2— | H,H,H | Methoxy | Methoxy | trans | 116–117, 5.39 |
| 1a.197 | 6-Chloro-thiazolo[5,4-b]-pyridin-2-yl | —SCH2— | H,H,H | Methoxy | Methoxy | trans | oil; 5.40 |
| 1a.198 | 1-Phenyl-1,2,3,4-tetrazol-5-yl | —SCH2— | H,H,H | Methoxy | Methoxy | trans | oil; 5.37 |
| 1a.199 | 4-Phenyl-1,3,4-oxadiazol-2-yl | —OCH2— | H,H,H | Methoxy | Methoxy | trans | |
| 1a.200 | 1-Phenylpyrazol-4-yl | —OCH2— | H,H,H | Methoxy | Methoxy | trans | |
| 1a.201 | 1-(4-Cyanophenyl)-pyrazol-4-yl | —OCH2— | H,H,H | Methoxy | Methoxy | trans | |
| 1a.202 | 5-Phenyl-isoxazol-3-yl | —OCH2— | H,H,H | Methoxy | Methoxy | trans | |
| 1a.203 | 1-Methyl-3-trifluormethyl-pyrazol-5-yl | —OCH2— | H,H,H | Methoxy | Methoxy | trans | |
| 1a.204 | 2-Propyl-6-trifluoromethyl-pyrimidin-4-yl | —OCH2— | H,H,H | Methoxy | Methoxy | trans | |
| 1a.205 | 5-Chloro-6-methoxy-2-methylthio-pyrimidin-4-yl | —OCH2— | H,H,H | Methoxy | Methoxy | trans | |
| 1a.206 | 5-Chloro-4-cyclohexyl-6-methyl-pyrimidin-2-yl | —OCH2— | H,H,H | Methoxy | Methoxy | trans | |
| 1a.207 | 3-Cyano-4,6-dimethyl-pyridin-2-yl | —OCH2— | H,H,H | Methoxy | Methoxy | trans | |

TABLE 1a-continued

Compounds of the formula 1a

| Comp. no. | R²⁹— | —A— | U,V,W | R¹—Xₘ— | —Y | Isomer | m.p.; ¹H—NMR (°C.) (ppm) |
|---|---|---|---|---|---|---|---|
| 1a.208 | Phenyl | —C≡C— | H,H,H | Methoxy | Methoxy | trans | |
| 1a.209 | 2-Methyl-phenyl | —C≡C— | H,H,H | Methoxy | Methoxy | trans | |
| 1a.210 | 3-Methyl-phenyl | —C≡C— | H,H,H | Methoxy | Methoxy | trans | |
| 1a.211 | 4-Methyl-phenyl | —C≡C— | H,H,H | Methoxy | Methoxy | trans | |
| 1a.212 | n-Butyl | —C≡C— | H,H,H | Methoxy | Methoxy | trans | |
| 1a.213 | Benzyl | —C≡C— | H,H,H | Methoxy | Methoxy | trans | |
| 1a.214 | 2-Chlorobenzyl | —C≡C— | H,H,H | Methoxy | Methoxy | trans | |
| 1a.215 | 2-Phenylethyl | —C≡C— | H,H,H | Methoxy | Methoxy | trans | |
| 1a.216 | Pyridin-2-yl | —C≡C— | H,H,H | Methoxy | Methoxy | trans | |
| 1a.217 | Pyridin-4-yl | —C≡C— | H,H,H | Methoxy | Methoxy | trans | |
| 1a.218 | Quinolin-2-yl | —C≡C— | H,H,H | Methoxy | Methoxy | trans | |
| 1a.219 | Isochinolin-4-yl | —C≡C— | H,H,H | Methoxy | Methoxy | trans | |
| 1a.220 | Benzoxazol-2-yl | —C≡C— | H,H,H | Methoxy | Methoxy | trans | |
| 1a.221 | Benzthiazol-2-yl | —C≡C— | H,H,H | Methoxy | Methoxy | trans | |
| 1a.223 | Benzimidazol-2-yl | —C≡C— | H,H,H | Methoxy | Methoxy | trans | |
| 1a.224 | Thien-2-yl | —C≡C— | H,H,H | Methoxy | Methoxy | trans | |
| 1a.225 | Furan-2-yl | —C≡C— | H,H,H | Methoxy | Methoxy | trans | |
| 1a.226 | 4-(4-Acetylphenyl)-phenyl | —C≡C— | H,H,H | Methoxy | Methoxy | trans | |
| 1a.229 | 3-Phenoxy-phenyl | —C≡C— | H,H,H | Methoxy | Methoxy | trans | |
| 1a.230 | Biphenyl-4-yl | —C≡C— | H,H,H | Methoxy | Methoxy | trans | |

TABLE 1a-continued

Compounds of the formula 1a

| Comp. no. | R$^{29}$— | —A— | U,V,W | R$^1$—X$_m$— | —Y | Isomer | m.p.; $^1$H—NMR (°C.) (ppm) |
|---|---|---|---|---|---|---|---|
| 1a.231 | Biphenyl-3-yl | —C≡C— | H,H,H | Methoxy | Methoxy | trans | |
| 1a.232 | tert.-Butyl | —C≡C— | H,H,H | Methoxy | Methoxy | trans | |
| 1a.233 | Phenyl | (E)—HC=CH— | H,H,H | Methoxy | Methoxy | trans | oil; 5.44 |
| 1a.234 | Phenyl | (Z)—HC=CH— | H,H,H | Methoxy | Methoxy | trans | oil; 5.32 |
| 1a.235 | 2-Chlorophenyl | —HC=CH— | H,H,H | Methoxy | Methoxy | trans | |
| 1a.236 | 3-Chlorophenyl | —HC=CH— | H,H,H | Methoxy | Methoxy | trans | |
| 1a.237 | 4-Chlorophenyl | —HC=CH— | H,H,H | Methoxy | Methoxy | trans | 65–69; 5.45 |
| 1a.238 | 2-Nitrophenyl | (E)—HC=CH— | H,H,H | Methoxy | Methoxy | trans | oil; 5.36 |
| 1a.239 | 2-Nitrophenyl | (Z)—HC=CH— | H,H,H | Methoxy | Methoxy | trans | 128–132; 5.48 |
| 1a.240 | 3-Nitrophenyl | (E)—HC=CH— | H,H,H | Methoxy | Methoxy | trans | 62–65; 5.34 |
| 1a.241 | 3-Nitrophenyl | (Z)—HC=CH— | H,H,H | Methoxy | Methoxy | trans | |
| 1a.242 | 4-Nitrophenyl | —HC=CH— | H,H,H | Methoxy | Methoxy | trans | |
| 1a.243 | 2-Trifluormethylphenyl | (E)—HC=CH— | H,H,H | Methoxy | Methoxy | trans | oil; 5.44 |
| 1a.244 | 2-Trifluormethylphenyl | (Z)—HC=CH— | H,H,H | Methoxy | Methoxy | trans | oil; 5.37 |
| 1a.245 | 3-Trifluoromethylphenyl | (E)—HC=CH— | H,H,H | Methoxy | Methoxy | trans | oil; 5.46 |
| 1a.246 | 3-Trifluoromethylphenyl | (Z)—HC=CH— | H,H,H | Methoxy | Methoxy | trans | oil; 5.33 |
| 1a.247 | 2-Methylphenyl | (E)—HC=CH— | H,H,H | Methoxy | Methoxy | trans | oil; 5.42 |
| 1a.248 | 2-Methylphenyl | (Z)—HC=CH— | H,H,H | Methoxy | Methoxy | trans | oil; 5.36 |
| 1a.249 | 3-Methylphenyl | —HC=CH— | H,H,H | Methoxy | Methoxy | trans | |
| 1a.250 | 4-Methylphenyl | (E)—HC=CH— | H,H,H | Methoxy | Methoxy | trans | oil; 5.43 |
| 1a.251 | 4-Methylphenyl | (Z)—HC=CH— | H,H,H | Methoxy | Methoxy | trans | oil; 5.31 |
| 1a.252 | 2,4-Difluorophenyl | —HC=CH— | H,H,H | Methoxy | Methoxy | trans | |
| 1a.253 | 2,4,6-Trichlorophenyl | —HC=CH— | H,H,H | Methoxy | Methoxy | trans | |
| 1a.254 | 4-tert.-Butylphenyl | —HC=CH— | H,H,H | Methoxy | Methoxy | trans | |
| 1a.255 | 3-Cyano-4-dimethylamino-2-fluorophenyl | —HC=CH— | H,H,H | Methoxy | Methoxy | trans | |
| 1a.256 | 4-Cyanophenyl | —HC=CH— | H,H,H | Methoxy | Methoxy | trans | |
| 1a.257 | 3-Benzoylphenyl | —HC=CH— | H,H,H | Methoxy | Methoxy | trans | |
| 1a.258 | 4-Benzoylphenyl | —HC=CH— | H,H,H | Methoxy | Methoxy | trans | |
| 1a.259 | 2-Cyclohexylphenyl | —HC=CH— | H,H,H | Methoxy | Methoxy | trans | |
| 1a.260 | 3-Cyclohexylphenyl | —HC=CH— | H,H,H | Methoxy | Methoxy | trans | |
| 1a.261 | 4-Cyclohexylphenyl | —HC=CH— | H,H,H | Methoxy | Methoxy | trans | |
| 1a.262 | 2-Benzyloxyphenyl | —HC=CH— | H,H,H | Methoxy | Methoxy | trans | |
| 1a.263 | 3-Benzyloxyphenyl | —HC=CH— | H,H,H | Methoxy | Methoxy | trans | oil; 5.43 |
| 1a.264 | 4-Benzyloxyphenyl | (E)—HC=CH— | H,H,H | Methoxy | Methoxy | trans | 118–120; 5.43 |
| 1a.265 | 4-Benzyloxyphenyl | (Z)—HC=CH— | H,H,H | Methoxy | Methoxy | trans | |

TABLE 1a-continued

Compounds of the formula 1a

| Comp. no. | $R^{29}-$ | $-A-$ | U,V,W | $R^1-X_m-$ | $-Y$ | Isomer | m.p.; $^1$H—NMR (°C.) (ppm) |
|---|---|---|---|---|---|---|---|
| 1a.266 | 2-Phenylphenyl | $-HC=CH-$ | H,H,H | Methoxy | Methoxy | trans | |
| 1a.267 | 3-Phenylphenyl | $-HC=CH-$ | H,H,H | Methoxy | Methoxy | trans | 110–112; 5.44 |
| 1a.268 | 4-Phenylphenyl | (E)$-HC=CH-$ | H,H,H | Methoxy | Methoxy | trans | oil; 5.33 |
| 1a.269 | 4-Phenylphenyl | (Z)$-HC=CH-$ | H,H,H | Methoxy | Methoxy | trans | |
| 1a.270 | 2-Phenoxyphenyl | $-HC=CH-$ | H,H,H | Methoxy | Methoxy | trans | oil; 5.41 |
| 1a.271 | 3-Phenoxyphenyl | (E)$-HC=CH-$ | H,H,H | Methoxy | Methoxy | trans | oil; 5.31 |
| 1a.272 | 3-Phenoxyphenyl | (Z)$-HC=CH-$ | H,H,H | Methoxy | Methoxy | trans | oil; 5.44 |
| 1a.273 | 4-Phenoxyphenyl | (E)$-HC=CH-$ | H,H,H | Methoxy | Methoxy | trans | |
| 1a.274 | 4-Phenoxyphenyl | (Z)$-HC=CH-$ | H,H,H | Methoxy | Methoxy | trans | |
| 1a.275 | 4-Pyrrolidin-1-yl-phenyl | $-HC=CH-$ | H,H,H | Methoxy | Methoxy | trans | |
| 1a.276 | 4-Methoxycarbonylphenyl | $-HC=CH-$ | H,H,H | Methoxy | Methoxy | trans | |
| 1a.277 | 3-Bromo-5-methylphenyl | $-HC=CH-$ | H,H,H | Methoxy | Methoxy | trans | |
| 1a.278 | 4-[(CH$_3$)$_2$—CH—CH$_3$—O—N=C(CH$_3$)—C$_6$H$_4$ | $-HC=CH-$ | H,H,H | Methoxy | Methoxy | trans | |
| 1a.279 | 3-(2-Pyrimidinyl)-phenyl | $-HC=CH-$ | H,H,H | Methoxy | Methoxy | trans | |
| 1a.280 | 4-(4-Thiazolyl)-phenyl | $-HC=CH-$ | H,H,H | Methoxy | Methoxy | trans | |
| 1a.281 | 5-[1-Methyl-3-trifluormethyl-pyrazol-5-yl)-thiophen-2-yl | $-HC=CH-$ | H,H,H | Methoxy | Methoxy | trans | |
| 1a.282 | 3-(5-n-Propyl-isoxazol-3-yl)-phenyl | $-HC=CH-$ | H,H,H | Methoxy | Methoxy | trans | |
| 1a.283 | Naphth-1-yl | $-HC=CH-$ | H,H,H | Methoxy | Methoxy | trans | |
| 1a.284 | Naphth-2-yl | $-HC=CH-$ | H,H,H | Methoxy | Methoxy | trans | |
| 1a.285 | Phenanthren-3-yl | $-HC=CH-$ | H,H,H | Methoxy | Methoxy | trans | |
| 1a.286 | Anthracen-2-yl | $-HC=CH-$ | H,H,H | Methoxy | Methoxy | trans | |
| 1a.287 | Pyrrol-2-yl | $-HC=CH-$ | H,H,H | Methoxy | Methoxy | trans | oil; 5.42 |
| 1a.288 | Pyrrol-3-yl | (E)$-HC=CH-$ | H,H,H | Methoxy | Methoxy | trans | |
| 1a.289 | Pyrrol-3-yl | (Z)$-HC=CH-$ | H,H,H | Methoxy | Methoxy | trans | |
| 1a.290 | Furan-2-yl | (E)$-HC=CH-$ | H,H,H | Methoxy | Methoxy | trans | oil; 5.44 |
| 1a.291 | Furan-2-yl | (Z)$-HC=CH-$ | H,H,H | Methoxy | Methoxy | trans | oil; 5.43 |
| 1a.292 | Furan-3-yl | (E)$-HC=CH-$ | H,H,H | Methoxy | Methoxy | trans | oil; 5.30 |
| 1a.293 | Furan-3-yl | (Z)$-HC=CH-$ | H,H,H | Methoxy | Methoxy | trans | oil; 5.44 |
| 1a.294 | Thiophen-2-yl | (E)$-HC=CH-$ | H,H,H | Methoxy | Methoxy | trans | |
| 1a.295 | Thiophen-2-yl | (Z)$-HC=CH-$ | H,H,H | Methoxy | Methoxy | trans | oil; 5.43 |
| 1a.296 | Thiophen-3-yl | (E)$-HC=CH-$ | H,H,H | Methoxy | Methoxy | trans | oil; 5.31 |
| 1a.297 | Thiophen-3-yl | (Z)$-HC=CH-$ | H,H,H | Methoxy | Methoxy | trans | oil; 5.44 |
| 1a.298 | 2-Methyl-thiazol-4-yl | (E)$-HC=CH-$ | H,H,H | Methoxy | Methoxy | trans | oil; 5.30 |
| 1a.299 | 2-Methyl-thiazol-4-yl | (Z)$-HC=CH-$ | H,H,H | Methoxy | Methoxy | trans | 128–130; 5.48 |
| 1a.300 | 3-(4-Chlorophenyl)-isoxazol-5-yl | (E)$-HC=CH-$ | H,H,H | Methoxy | Methoxy | trans | |
| 1a.301 | 3-(4-Chlorophenyl)-isoxazol-5-yl | (Z)$-HC=CH-$ | H,H,H | Methoxy | Methoxy | trans | |

TABLE 1a-continued

Compounds of the formula 1a

| Comp. no. | R29— | —A— | U,V,W | R1—Xm— | —Y | Isomer | m.p.; 1H—NMR (°C.) (ppm) |
|---|---|---|---|---|---|---|---|
| 1a.302 | 2-(4-Chlorophenyl)-oxazol-4-yl | (E)—HC=CH— | H,H,H | Methoxy | Methoxy | trans | 132–136; 5.48 |
| 1a.303 | 2-(4-Chlorophenyl)-oxazol-4-yl | (Z)—HC=CH— | H,H,H | Methoxy | Methoxy | trans | oil; 5.28 |
| 1a.304 | 1-(4-Chlorophenyl)-pyrrol-3-yl | (E)—HC=CH— | H,H,H | Methoxy | Methoxy | trans | 132–135; 5.46 |
| 1a.305 | 1-(4-Chlorophenyl)-pyrrol-3-yl | (Z)—HC=CH— | H,H,H | Methoxy | Methoxy | trans | 133–136; 5.28 |
| 1a.306 | 2-Phenyl-thiazol-4-yl | (E)—HC=CH— | H,H,H | Methoxy | Methoxy | trans | oil; 5.46 |
| 1a.307 | 2-Phenyl-thiazol-4-yl | (Z)—HC=CH— | H,H,H | Methoxy | Methoxy | trans | 102–105; 5.29 |
| 1a.308 | 2-Phenyl-1,3,4-thiadiazol-5-yl | (E)—HC=CH— | H,H,H | Methoxy | Methoxy | trans | 129–131; 5.49 |
| 1a.309 | 2-Phenyl-1,3,4-thiadiazol-5-yl | (Z)—HC=CH— | H,H,H | Methoxy | Methoxy | trans | |
| 1a.310 | 3-(4-Fluorphenyl)-1,2,4-oxadiazol-5-yl | (E)—HC=CH— | H,H,H | Methoxy | Methoxy | trans | 154–156; 5.51 |
| 1a.311 | 3-(4-Fluorphenyl)-1,2,4-oxadiazol-5-yl | (Z)—HC=CH— | H,H,H | Methoxy | Methoxy | trans | |
| 1a.312 | 2-(4-Methylphenyl)-thiazol-4-yl | (E)—HC=CH— | H,H,H | Methoxy | Methoxy | trans | 147–150; 5.46 |
| 1a.313 | 2-(4-Methylphenyl)-thiazol-4-yl | (Z)—HC=CH— | H,H,H | Methoxy | Methoxy | trans | |
| 1a.314 | 2-(4-Chlorophenyl)-thiazol-4-yl | (E)—HC=CH— | H,H,H | Methoxy | Methoxy | trans | 145–147; 5.47 |
| 1a.315 | 2-(4-Chlorophenyl)-thiazol-4-yl | (Z)—HC=CH— | H,H,H | Methoxy | Methoxy | trans | |
| 1a.316 | 1-(3-Chlorophenyl)-pyrazol-4-yl | (E)—HC=CH— | H,H,H | Methoxy | Methoxy | trans | 124–128; 5.47 |
| 1a.317 | 1-(3-Chlorophenyl)-pyrazol-4-yl | (Z)—HC=CH— | H,H,H | Methoxy | Methoxy | trans | oil; 5.29 |
| 1a.318 | 1-(4-Methoxypchnyl)-pyrazol-4-yl | (E)—HC=CH— | H,H,H | Methoxy | Methoxy | trans | 121–123; 5.46 |
| 1a.319 | 1-(4-Methoxyphenyl)-pyrazol-4-yl | (Z)—HC=CH— | H,H,H | Methoxy | Methoxy | trans | 108–110; 5.28 |
| 1a.320 | 1-(4-Chlorophenyl)-pyrazol-4-yl | (E)—HC=CH— | H,H,H | Methoxy | Methoxy | trans | 140–142; 5.45 |
| 1a.321 | 1-(4-Chlorophenyl)-pyrazol-4-yl | (Z)—HC=CH— | H,H,H | Methoxy | Methoxy | trans | 142–145; 5.28 |
| 1a.322 | 5-(4-Chlorophenyl)-4-methyl-isoxazol-3-yl | (E)—HC=CH— | H,H,H | Methoxy | Methoxy | trans | 116–118; 5.46 |
| 1a.323 | 5-(4-Chlorophenyl)-4-methyl-isoxazol-3-yl | (Z)—HC=CH— | H,H,H | Methoxy | Methoxy | trans | oil; 5.36 |
| 1a.324 | 3-Isobutylisoxazol-5-yl | (E)—HC=CH— | H,H,H | Methoxy | Methoxy | trans | oil; 5.43 |
| 1a.325 | 3-Isobutylisoxazol-5-yl | (Z)—HC=CH— | H,H,H | Methoxy | Methoxy | trans | |
| 1a.326 | Isoquinolin-6-yl | —HC=CH— | H,H,H | Methoxy | Methoxy | trans | |
| 1a.327 | Benzimidazol-2-yl | —HC=CH— | H,H,H | Methoxy | Methoxy | trans | |
| 1a.328 | 2-(4-Thiazolyl)-thiazol-4-yl | —HC=CH— | H,H,H | Methoxy | Methoxy | trans | |
| 1a.329 | Tetrahydropyran-3-yl | (E)—HC=CH— | H,H,H | Methoxy | Methoxy | trans | oil; 5.37 |
| 1a.330 | Tetrahydropyran-3-yl | (Z)—HC=CH— | H,H,H | Methoxy | Methoxy | trans | |
| 1a.331 | 2-Phenyl-tetrahydropyran-4-yl | (E)—HC=CH— | H,H,H | Methoxy | Methoxy | trans | oil; 5.33 |
| 1a.332 | 2-Phenyl-tetrahydropyran- | (Z)—HC=CH— | H,H,H | Methoxy | Methoxy | trans | |
| 1a.333 | 2-(3-Tetrahydropyranyl)-tetrahydropyran-4-yl | (E)—HC=CH— | H,H,H | Methoxy | Methoxy | trans | oil; 5.38 |
| 1a.334 | 2(3-Tetrahydropyranyl)-tetrahydropyran-4-yl | (Z)—HC=CH— | H,H,H | Methoxy | Methoxy | trans | |
| 1a.335 | Benzyl | —HC=CH— | H,H,H | Methoxy | Methoxy | trans | |
| 1a.336 | 4-Phenoxy-but-1-yl | —HC=CH— | H,H,H | Methoxy | Methoxy | trans | |

TABLE 1a-continued

Compounds of the formula 1a

| Comp. no. | R29 — | —A— | U,V,W | R1—Xm— | —Y | Isomer | m.p.; 1H—NMR (°C.) (ppm) |
|---|---|---|---|---|---|---|---|
| 1a.337 | n-Nonyl | —HC=CH— | H,H,H | Methoxy | Methoxy | trans | oil; 5.38 |
| 1a.338 | Phenylethynyl | —HC=CH— | H,H,H | Methoxy | Methoxy | trans | oil; 5.42 |
| 1a.339 | Phenyl | —CH2—CH2— | H,H,H | Methoxy | Methoxy | trans | |
| 1a.340 | 2-Trifluorophenyl | —CH2—CH2— | H,H,H | Methoxy | Methoxy | trans | |
| 1a.341 | 3-Methylphenyl | —CH2—CH2— | H,H,H | Methoxy | Methoxy | trans | |
| 1a.342 | 4-Benzoylphenyl | —CH2—CH2— | H,H,H | Methoxy | Methoxy | trans | |
| 1a.343 | 2,4,6-Trichlorophenyl | —CH2—CH2— | H,H,H | Methoxy | Methoxy | trans | oil; 5.40 |
| 1a.344 | 4-Phenylphenyl | —CH2—CH2— | H,H,H | Methoxy | Methoxy | trans | |
| 1a.345 | 4-[(CH3)2—CH—CH2—O—N=C(CH3)]—C6H4 | —CH2—CH2— | H,H,H | Methoxy | Methoxy | trans | |
| 1a.346 | 3-(2-Pyrimidinyl)-phenyl | —CH2—CH2— | H,H,H | Methoxy | Methoxy | trans | 157–159; 5.38 |
| 1a.347 | 2-(4-Fluorophenyl)-thiazol-4-yl | —CH2—CH2— | H,H,H | Methoxy | Methoxy | trans | |
| 1a.348 | 3-(4-Fluorophenyl)-1,2,4-oxadiazol-5-yl | —CH2—CH2— | H,H,H | Methoxy | Methoxy | trans | |
| 1a.349 | Isoquinolin-6-yl | —CH2—CH2— | H,H,H | Methoxy | Methoxy | trans | |
| 1a.350 | 2-(4-Thiazolyl)-thiazol-4-yl | —CH2—CH2— | H,H,H | Methoxy | Methoxy | trans | |
| 1a.351 | 4-Phenoxyphenyl | —CH2—CH2— | H,H,H | Methoxy | Methoxy | trans | |
| 1a.352 | 2-Phenyl-thiazol-4-yl | —CH2—CH2— | H,H,H | Methoxy | Methoxy | trans | |
| 1a.353 | 3-Cyclohexylphenyl | —CH2—CH2— | H,H,H | Methoxy | Methoxy | trans | |
| 1a.354 | Phenyl | —C(CH3)=N—O—CH2— | H,H,H | Methoxy | Methoxy | trans | oil; 5.36 |
| 1a.355 | 3-Bromophenyl | —C(CH3)=N—O—CH2— | H,H,H | Methoxy | Methoxy | trans | oil; 5.38 |
| 1a.356 | 4-Chlorophenyl | —C(CH3)=N—O—CH2— | H,H,H | Methoxy | Methoxy | trans | oil; 5.36 |
| 1a.357 | 4-Chlorophenyl | —C(H)=N—O—CH2— | H,H,H | Methoxy | Methoxy | trans | |
| 1a.358 | 4-Chlorophenyl | —C(Ph)=N—O—CH2— | H,H,H | Methoxy | Methoxy | trans | |
| 1a.359 | 4-Phenylphenyl | —C(CH3)=N—O—CH2— | H,H,H | Methoxy | Methoxy | trans | oil; 5.35 |
| 1a.360 | Naphth-2-yl | —C(CH3)=N—O—CH2— | H,H,H | Methoxy | Methoxy | trans | |
| 1a.361 | 2-Methyl-4-chlorophenyl | —C(CH3)=N—O—CH2— | H,H,H | Methoxy | Methoxy | trans | |
| 1a.362 | 2-Methyl-2,5-dimethoxyphenyl | —C(CH3)=N—O—CH2— | H,H,H | Methoxy | Methoxy | trans | oil; 5.35 |
| 1a.363 | Furan-2-yl | —C(CH3)=N—O—CH2— | H,H,H | Methoxy | Methoxy | trans | |
| 1a.364 | Pyridin-3-yl | —C(CH3)=N—O—CH2— | H,H,H | Methoxy | Methoxy | trans | |
| 1a.365 | Pyrazin-2-yl | —C(CH3)=N—O—CH2— | H,H,H | Methoxy | Methoxy | trans | |
| 1a.366 | 1-Methyl-pyrrol-2-yl | —C(CH3)=N—O—CH2— | H,H,H | Methoxy | Methoxy | trans | oil; 5.35 |
| 1a.367 | Thiazol-2-yl | —C(CH3)=N—O—CH2— | H,H,H | Methoxy | Methoxy | trans | oil; 5.37 |
| 1a.368 | 4-n-Hexylphenyl | —C(CH3)=N—O—CH2— | H,H,H | Methoxy | Methoxy | trans | |
| 1a.369 | Phenyl | —N=CH— | H,H,H | Methoxy | Methoxy | trans | |
| 1a.370 | 2,4-Dimethylphenyl | —N=CH— | H,H,H | Methoxy | Methoxy | trans | |
| 1a.371 | 4-Phenoxyphenyl | —N=CH— | H,H,H | Methoxy | Methoxy | trans | |
| 1a.372 | 4-tert.-Butylphenyl | —N=CH— | H,H,H | Methoxy | Methoxy | trans | |
| 1a.373 | Diphenyl-4-yl | —N=CH— | H,H,H | Methoxy | Methoxy | trans | |

TABLE 1a-continued

Compounds of the formula 1a

| Comp. no. | R29— | —A— | U,V,W | R1—Xm— | —Y | Isomer | m.p.; 1H—NMR (°C.) (ppm) |
|---|---|---|---|---|---|---|---|
| 1a.374 | 4,6-Dimethylpyrimidin-2-yl | —N═CH— | H,H,H | Methoxy | Methoxy | trans | |
| 1a.375 | Isoquinolin-5-yl | —N═CH— | H,H,H | Methoxy | Methoxy | trans | |
| 1a.376 | 3-Pyridyl | —N═CH— | H,H,H | Methoxy | Methoxy | trans | |
| 1a.377 | Phenyl | —N═N— | H,H,H | Methoxy | Methoxy | trans | |
| 1a.378 | Phenyl | —ON═CH— | H,H,H | Methoxy | Methoxy | trans | |
| 1a.379 | Geranyl | —ON═CH— | H,H,H | Methoxy | Methoxy | trans | |
| 1a.380 | Benzyl | —ON═CH— | H,H,H | Methoxy | Methoxy | trans | |
| 1a.381 | 3-Chlorobenzyl | —ON═CH— | H,H,H | Methoxy | Methoxy | trans | |
| 1a.382 | 2,4-Dimethylbenzyl | —ON═CH— | H,H,H | Methoxy | Methoxy | trans | |
| 1a.383 | 4-Phenylbenzyl | —ON═CH— | H,H,H | Methoxy | Methoxy | trans | |
| 1a.384 | 1-Naphthylmethyl | —ON═CH— | H,H,H | Methoxy | Methoxy | trans | |
| 1a.385 | 2-(1-Naphthyl)-ethyl | —ON═CH— | H,H,H | Methoxy | Methoxy | trans | |
| 1a.386 | 3-(4-Chlorophenyl)-allyl | —ON═CH— | H,H,H | Methoxy | Methoxy | trans | |
| 1a.387 | 2-(4-Fluorophenyl)-oxazol-4-yl-methyl | —ON═CH— | H,H,H | Methoxy | Methoxy | trans | |
| 1a.388 | 2-(2-Fluorophenoxy)-ethyl | —ON═CH— | H,H,H | Methoxy | Methoxy | trans | |
| 1a.389 | 3-Phenyl-benzyl | —O—N═CH— | H,H,H | Methoxy | Methoxy | trans | |
| 1a.390 | 4-(3-Phenoxyphenyl)-butyl | —O—N═CH— | H,H,H | Methoxy | Methoxy | trans | |
| 1a.391 | 6-Chloro-pyridin-3-yl-methyl | —O—N═CH— | H,H,H | Methoxy | Methoxy | trans | |
| 1a.392 | 4-(4-Fluorophenyl)-3-methoximino-butyl | —O—N═CH— | H,H,H | Methoxy | Methoxy | trans | |
| 1a.393 | 2-(4-Fluorophenyl)-thiazol-4-yl | (Z)—CH═CH | H,H,H | Methoxy | Methoxy | trans | oil; 5.39 |
| 1a.394 | 2-(4-Fluorophenyl)-thiazol-4-yl | (E)—CH═CH | H,H,H | Methoxy | Methoxy | trans | 148–150; 5.48 |
| 1a.395 | 2-(4-Fluorophenyl)-thiazol-4-yl | (E)—CH═CH | H,H,H | Methoxy | n-Butoxy | trans | 155–158; 5.40 |
| 1a.396 | 2-(4-Fluorophenyl)-thiazol-4-yl | (E)—CH═CH | H,H,H | Methoxy | Ethoxy | trans | |
| 1a.397 | 2-(4-Fluorophenyl)-thiazol-4-yl | (E)—CH═CH | H,H,H | Methoxy | n-Propoxy | trans | |
| 1a.398 | 2-(4-Fluorophenyl)-thiazol-4-yl | (E)—CH═CH | H,H,H | Methoxy | iso-Butoxy | trans | |
| 1a.399 | 2-(4-Fluorophenyl)-thiazol-4-yl | (E)—CH═CH | H,H,H | Methoxy | sec-Butoxy | trans | |
| 1a.400 | 2-(4-Fluorophenyl)-thiazol-4-yl | (E)—CH═CH | H,H,H | Methoxy | n-Pentyloxy | trans | |
| 1a.401 | 2-(4-Fluorophenyl)-thiazol-4-yl | (E)—CH═CH | H,H,H | Methoxy | Cyclopentyloxy | trans | |
| 1a.402 | 2-(4-Fluorophenyl)-thiazol-4-yl | (E)—CH═CH | H,H,H | Methoxy | Allyloxy | trans | |
| 1a.403 | 2-(4-Fluorophenyl)-thiazol-4-yl | (E)—CH═CH | H,H,H | Methoxy | 2-Chloroallyloxy | trans | |
| 1a.404 | 2-(4-Fluorophenyl)-thiazol-4-yl | (E)—CH═CH | H,H,H | Methoxy | Propargyloxy | trans | |
| 1a.405 | 2-(4-Fluorophenyl)-thiazol-4-yl | (E)—CH═CH | H,H,H | Methoxy | Methylthio | trans | |
| 1a.406 | 2-(4-Fluorophenyl)-thiazol-4-yl | (E)—CH═CH | H,H,H | Methoxy | Dimethylamino | trans | |
| 1a.407 | 2-(4-Fluorophenyl)-thiazol-4-yl | (E)—CH═CH | H,H,H | Methoxy | Ethylamino | trans | |
| 1a.408 | 2-(4-Fluorophenyl)-thiazol-4-yl | (E)—CH═CH | H,H,H | Methoxy | N-Methyl-N-ethylamino | trans | |
| 1a.409 | 2-(4-Fluorophenyl)-thiazol-4-yl | (E)—CH═CH— | H,H,H | Methoxy | Diethylamino | trans | |

TABLE 1a-continued

Compounds of the formula 1a

| Comp. no. | R29— | —A— | U,V,W | R1—Xm— | —Y | Isomer | m.p.; 1H—NMR (°C.) (ppm) |
|---|---|---|---|---|---|---|---|
| 1a.410 | 2-(4-Fluorophenyl)-thiazol-4-yl | (E)—CH=CH— | H,H,H | Methoxy | Isopropylamino | trans | |
| 1a.411 | 2-(4-Fluorophenyl)-thiazol-4-yl | (E)—CH=CH— | H,H,H | Methoxy | Amino | trans | |
| 1a.412 | 2-(4-Fluorophenyl)-thiazol-4-yl | (E)—CH=CH— | H,H,H | Methoxy | Methylamino | trans | |
| 1a.413 | 2-(4-Fluorophenyl)-thiazol-4-yl | (E)—CH=CH— | H,H,H | Methoxy | N-Methyl-N-iso-propylamino | trans | |
| 1a.414 | 2-(4-Fluorophenyl)-thiazol-4-yl | (E)—CH=CH— | H,H,H | Methoxy | Allylamino | trans | |
| 1a.415 | 2-(4-Fluorophenyl)-thiazol-4-yl | (E)—CH=CH— | H,H,H | Methoxy | —NHOH | trans | |
| 1a.416 | 2-(4-Fluorophenyl)-thiazol-4-yl | (E)—CH=CH— | H,H,H | Methoxy | —N(CH3)OH | trans | |
| 1a.417 | 2-(4-Fluorophenyl)-thiazol-4-yl | (E)—CH=CH— | H,H,H | Methoxy | —NHOCH3 | trans | |
| 1a.418 | 2-(4-Fluorophenyl)-thiazol-4-yl | (E)—CH=CH— | H,H,H | Methoxy | —N(CH3)OCH3 | trans | |
| 1a.419 | 2-(4-Fluorophenyl)-thiazol-4-yl | (E)—CH=CH— | H,H,H | Methoxy | —N(C2H5)OH | trans | |
| 1a.420 | 2-(4-Fluorophenyl)-thiazol-4-yl | (E)—CH=CH— | H,H,H | Methyl | Methoxy | trans | |
| 1a.421 | 2-(4-Fluorophenyl)-thiazol-4-yl | (Z)—CH=CH— | H,H,H | Methyl | Methoxy | cis | |
| 1a.422 | 2-(4-Fluorophenyl)-thiazol-4-yl | (E)—CH=CH— | H,H,H | Methyl | Methoxy | trans | |
| 1a.423 | 2-(4-Fluorophenyl)-thiazol-4-yl | (E)—CH=CH— | H,H,H | Methyl | Methoxy | cis | |
| 1a.424 | 2-(4-Fluorophenyl)-thiazol-4-yl | (E)—CH=CH— | H,H,H | Ethyl | Methoxy | trans | |
| 1a.425 | 2-(4-Fluorophenyl)-thiazol-4-yl | (E)—CH=CH— | H,H,H | Ethyl | Methoxy | cis | |
| 1a.426 | 2-(4-Fluorophenyl)-thiazol-4-yl | (E)—CH=CH— | H,H,H | n-Propyl | Methoxy | trans | |
| 1a.427 | 2-(4-Fluorophenyl)-thiazol-4-yl | (E)—CH=CH— | H,H,H | iso-Propyl | Methoxy | cis | |
| 1a.428 | 2-(k-Fluorophenyl)-thiazol-4-yl | (E)—CH=CH— | H,H,H | Ethoxy | Methoxy | trans | |
| 1a.429 | 2-(4-Fluorophenyl)-thiazol-4-yl | (E)—CH=CH— | H,H,H | n-Propyloxy | Methoxy | trans | |
| 1a.430 | 2-(4-Fluorophenyl)-thiazol-4-yl | (E)—CH=CH— | H,H,H | i-Propyloxy | Methoxy | trans | |
| 1a.431 | 2-(4-Fluorophenyl)-thiazol-4-yl | (E)—CH=CH— | H,H,H | n-Butyloxy | Methoxy | trans | |
| 1a.432 | 2-(4-Fluorophenyl)-thiazol-4-yl | (E)—CH=CH— | H,H,H | n-Hexyloxy | Methoxy | trans | |
| 1a.433 | 2-(4-Fluorophenyl)-thiazol-4-yl | (E)—CH=CH— | H,H,H | Methylthio | Methoxy | trans | |
| 1a.434 | 2-(4-Fluorophenyl)-thiazol-4-yl | (E)—CH=CH— | H,H,H | Ethylthio | Methoxy | trans | |
| 1a.435 | 2-(4-Fluorophenyl)-thiazol-4-yl | (E)—CH=CH— | H,H,H | n-Propylthio | Methoxy | trans | |
| 1a.436 | 2-(4-Fluorophenyl)-thiazol-4-yl | (E)—CH=CH— | H,H,H | Methylamino | Methoxy | trans | |
| 1a.437 | 2-(4-Fluorophenyl)-thiazol-4-yl | (E)—CH=CH— | H,H,H | Dimethylamino | Methoxy | trans | |
| 1a.438 | 2-(4-Fluorophenyl)-thiazol-4-yl | (E)—CH=CH— | H,H,H | Methoxyamino | Methoxy | trans | |
| 1a.439 | 2-(4-Fluorophenyl)-thiazol-4-yl | (E)—CH=CH— | H,H,H | Cl | Methoxy | trans | |
| 1a.440 | 2-(4-Fluorophenyl)-thiazol-4-yl | (E)—CH=CH— | H,H,H | Methyl | sec.-Butyloxy | trans | |
| 1a.441 | 2-(4-Fluorophenyl)-thiazol-4-yl | (E)—CH=CH— | H,H,H | Methyl | Methylthio | trans | |
| 1a.442 | 2-(4-Fluorophenyl)-thiazol-4-yl | (E)—CH=CH— | H,H,H | Methyl | Amino | trans | |
| 1a.443 | 2-(4-Fluorophenyl)-thiazol-4-yl | (E)—CH=CH— | H,H,H | Methyl | Methylamino | trans | |
| 1a.444 | 2-(4-Fluorophenyl)-thiazol-4-yl | (E)—CH=CH— | H,H,H | Methyl | Dimethylamino | trans | |
| 1a.445 | 2-(4-Fluorophenyl)-thiazol-4-yl | (E)—CH=CH— | H,H,H | Methyl | —N(CH3)OCH3 | trans | |

TABLE 1a-continued

Compounds of the formula 1a

| Comp. no. | R²⁹— | —A— | U,V,W | R¹—X_m— | —Y | Isomer | m.p.; ¹H—NMR (°C.) (ppm) |
|---|---|---|---|---|---|---|---|
| 1a.446 | 2-(4-Fluorophenyl)-thiazol-4-yl | (E)—CH═CH— | H,H,H | Methyl | —NHOCH₃ | trans | |
| 1a.447 | 2-(4-Fluorophenyl)-thiazol-4-yl | (E)—CH═CH— | H,H,H | Methyl | n-Propoxy | trans | |
| 1a.448 | 2-(4-Fluorophenyl)-thiazol-4-yl | (E)—CH═CH— | H,H,H | Methyl | i-Propoxy | trans | |
| 1a.449 | 2-(4-Fluorophenyl)-thiazol-4-yl | (E)—CH═CH— | 4-Ethoxy | Methoxy | Methoxy | trans | |
| 1a.450 | 2-(4-Fluorophenyl)-thiazol-4-yl | (E)—CH═CH— | 4-Methoxy | Methoxy | Methoxy | trans | |
| 1a.451 | 2-(4-Fluorophenyl)-thiazol-4-yl | (E)—CH═CH— | 4-t-Butyl | Methoxy | Methoxy | trans | |
| 1a.452 | 2-(4-Fluorophenyl)-thiazol-4-yl | (E)—CH═CH— | 4-Fluor | Methoxy | Methoxy | trans | |
| 1a.453 | 2-(4-Flurophenyl)-thiazol-4-yl | (E)—CH═CH— | 6-Methyl | Methoxy | Methoxy | trans | |
| 1a.454 | Biphenyl-4-yl | (E)—CH═CH— | H,H,H | Methyl | Methoxy | trans | |
| 1a.455 | Biphenyl-4-yl | (Z)—CH═CH— | H,H,H | Methyl | Methoxy | cis | |
| 1a.456 | Biphenyl-4-yl | (Z)—CH═CH— | H,H,H | Methyl | Methoxy | cis | |
| 1a.457 | Biphenyl-4-yl | (E)—CH═CH— | H,H,H | Methyl | Methoxy | trans | |
| 1a.458 | Biphenyl-4-yl | (E)—CH═CH— | H,H,H | Ethyl | Methoxy | cis | |
| 1a.459 | Biphenyl-4-yl | (E)—CH═CH— | H,H,H | Ethyl | Methoxy | cis | |
| 1a.460 | Biphenyl-4-yl | (E)—CH═CH— | H,H,H | n-Propyl | Methoxy | trans | |
| 1a.461 | Biphenyl-4-yl | (E)—CH═CH— | H,H,H | iso-Propyl | Methoxy | trans | |
| 1a.462 | Biphenyl-4-yl | (E)—CH═CH— | H,H,H | Ethoxy | Methoxy | trans | |
| 1a.463 | Biphenyl-4-yl | (E)—CH═CH— | H,H,H | n-Propyloxy | Methoxy | trans | |
| 1a.464 | Biphenyl-4-yl | (E)—CH═CH— | H,H,H | i-Propyloxy | Methoxy | trans | |
| 1a.465 | Biphenyl-4-yl | (E)—CH═CH— | H,H,H | n-Butyloxy | Methoxy | trans | |
| 1a.466 | Biphenyl-4-yl | (E)—CH═CH— | H,H,H | n-Hexyloxy | Methoxy | trans | |
| 1a.467 | Biphenyl-4-yl | (E)—CH═CH— | H,H,H | Methylthio | Methoxy | trans | |
| 1a.468 | Biphenyl-4-yl | (E)—CH═CH— | H,H,H | Ethylthio | Methoxy | trans | |
| 1a.469 | Biphenyl-4-yl | (E)—CH═CH— | H,H,H | n-Propylthio | Methoxy | trans | |
| 1a.470 | Biphenyl-4-yl | (E)—CH═CH— | H,H,H | Methylamino | Methoxy | trans | |
| 1a.471 | Biphenyl-4-yl | (E)—CH═CH— | H,H,H | Dimethylamino | Methoxy | trans | |
| 1a.472 | Biphenyl-4-yl | (E)—CH═CH— | H,H,H | Methoxyamino | Methoxy | trans | |
| 1a.473 | Biphenyl-4-yl | (E)—CH═CH— | H,H,H | Cl | Methoxy | trans | |
| 1a.474 | Biphenyl-4-yl | (E)—CH═CH— | H,H,H | Methyl | iso-Butoxy | trans | |
| 1a.475 | Biphenyl-4-yl | (E)—CH═CH— | H,H,H | Methyl | Methylthio | trans | |
| 1a.476 | Biphenyl-4-yl | (E)—CH═CH— | H,H,H | Methyl | Amino | trans | |
| 1a.477 | Biphenyl-4-yl | (E)—CH═CH— | H,H,H | Methyl | Methylamino | trans | |
| 1a.478 | Biphenyl-4-yl | (E)—CH═CH— | H,H,H | Methyl | Dimethylamino | trans | |
| 1a.479 | Biphenyl-4-yl | (E)—CH═CH— | H,H,H | Methyl | —N(CH₃)OCH₃ | trans | |
| 1a.480 | Biphenyl-4-yl | (E)—CH═CH— | H,H,H | Methyl | —NHOCH₃ | trans | |
| 1a.481 | Biphenyl-4-yl | (E)—CH═CH— | H,H,H | Methyl | n-Propoxy | trans | |
| 1a.482 | Biphenyl-4-yl | (E)—CH═CH— | H,H,H | Methyl | i-Propoxy | trans | |

TABLE 1a-continued

Compounds of the formula 1a

| Comp. no. | R²⁹— | —A— | U,V,W | R¹—Xₘ— | —Y | Isomer | m.p; ¹H—NMR (°C.) (ppm) |
|---|---|---|---|---|---|---|---|
| 1a.488 | Biphenyl-4-yl | (E)—CH═CH— | 4-Ethoxy | Methoxy | Methoxy | trans | |
| 1a.489 | Biphenyl-4-yl | (E)—CH═CH— | 4-Methoxy | Methoxy | Methoxy | trans | |
| 1a.490 | Biphenyl-4-yl | (E)—CH═CH— | 4-t-Butyl | Methoxy | Methoxy | trans | |
| 1a.491 | Biphenyl-4-yl | (E)—CH═CH— | 4-Fluor | Methoxy | Methoxy | trans | |
| 1a.492 | Biphenyl-4-yl | (E)—CH═CH— | 6-Methyl | Methoxy | Methoxy | trans | |
| 1a.493 | Phenyl | —O—CO— | H,H,H | Methoxy | Methoxy | trans | |
| 1a.494 | 2-Chlorophenyl | —O—CO— | H,H,H | Methoxy | Methoxy | trans | |
| 1a.495 | 3-Fluorphenyl | —O—CO— | H,H,H | Methoxy | Methoxy | trans | |
| 1a.496 | Diphenyl-4-yl | —O—CO— | H,H,H | Methoxy | Methoxy | trans | |
| 1a.497 | 2-Methylbenzyl | —O—CO— | H,H,H | Methoxy | Methoxy | trans | |
| 1a.498 | 3-Phenoxyphenyl | —O—CO— | H,H,H | Methoxy | Methoxy | trans | |
| 1a.499 | tert.-Butyl | —O—CO— | H,H,H | Methoxy | Methoxy | trans | |
| 1a.500 | Methyl | —NH—CO— | H,H,H | Methoxy | Methoxy | trans | |
| 1a.501 | Phenyl | —NH—CO— | H,H,H | Methoxy | Methoxy | trans | |
| 1a.502 | Cyclohexyl | —NH—CO— | H,H,H | Methoxy | Methoxy | trans | |
| 1a.503 | 3-Pyridyl | —N(CH₃)—CO— | H,H,H | Methoxy | Methoxy | trans | |
| 1a.504 | Benzyl | —N(CH₃)—CO— | H,H,H | Methoxy | Methoxy | trans | |
| 1a.505 | Phenyl | —N(CH₃)—CO— | H,H,H | Methoxy | Methoxy | trans | |
| 1a.506 | 2-Pyridyl | —CH₂— | H,H,H | Methoxy | Methoxy | trans | |
| 1a.507 | Phenyl | —HC═N— | H,H,H | Methoxy | Methoxy | trans | |
| 1a.508 | Methyl | —HC═N— | H,H,H | Methoxy | Methoxy | trans | |
| 1a.509 | 3-Trifluoromethylphenyl | —HC═N— | H,H,H | Methoxy | Methoxy | trans | |
| 1a.510 | 2-Methylphenyl | —HC═N— | H,H,H | Methoxy | Methoxy | trans | |
| 1a.511 | 4-Chlorophenyl | —HC═N— | H,H,H | Methoxy | Methoxy | trans | |
| 1a.512 | Biphenyl-4-yl | —(CH₃)C═N— | H,H,H | Methoxy | Methoxy | trans | |
| 1a.513 | Phenyl | —(CH₃)C═N— | H,H,H | Methoxy | Methoxy | trans | |
| 1a.514 | 4-Trifluoromethylphenyl | —(CH₃)C═N— | H,H,H | Methoxy | Methoxy | trans | |
| 1a.516 | 4-Nitrophenyl | —(CH₃)C═N— | H,H,H | Methoxy | Methoxy | trans | |
| 1a.517 | 3-Pyridyl | —(CH₃)C═N— | H,H,H | Methoxy | Methoxy | trans | |
| 1a.518 | 4-Trifluoromethylphenyl | (E)—HC═CH— | H,H,H | Methoxy | Methoxy | trans | oil; 5.46 |
| 1a.519 | 4-Trifluoromethylphenyl | (Z)—HC═CH— | H,H,H | Methoxy | Methoxy | trans | oil; 5.32 |
| 1a.520 | 4-Trifluoromethylphenyl | —SCH₂— | H,H,H | Methoxy | Methoxy | trans | oil; 5.39 |
| 1a.521 | 4,5-Diphenyl-oxazol-2-yl | —SCH₂— | H,H,H | Methoxy | Methoxy | trans | oil; 5.48 |
| 1a.522 | 4-Carboxyethyl-imidazol-2-yl | —SCH₂— | H,H,H | Methoxy | Methoxy | trans | oil; 5.39 |
| 1a.523 | 5-Methyl-1,3,4-thiadiazol-2-yl | —SCH₂— | H,H,H | Methoxy | Methoxy | trans | oil; 5.37 |
| 1a.524 | 1-Methyl-1,3,4-triazol-2-yl | —SCH₂— | H,H,H | Methoxy | Methoxy | trans | oil; 5.41 |
| 1a.525 | 5-(4-Chlorophenyl)-1,3,4-oxa- | —SCH₂— | H,H,H | Methoxy | Methoxy | trans | |

TABLE 1a-continued

Compounds of the formula 1a

| Comp. no. | R²⁹— | —A— | U,V,W | R¹—Xₘ— | —Y | Isomer | m.p.; ¹H—NMR (°C.) (ppm) |
|---|---|---|---|---|---|---|---|
| | diazol-2-yl | | | | | | |
| 1a.526 | 5-Methylamino-1,3,4-thia-diazol-2-yl | —SCH₂— | H,H,H | Methoxy | Methoxy | trans | oil; 5.38 |
| 1a.527 | 5-Benzylmercapto-1,3,4-thia-diazol-2-yl | —SCH₂— | H,H,H | Methoxy | Methoxy | trans | oil; 5.38 |
| 1a.528 | 5-(2-Chlorobenzyl)mercapto-1,3,4-thiadiazol-2-yl | —SCH₂— | H,H,H | Methoxy | Methoxy | trans | oil; 5.38 |
| 1a.529 | 5-(3-Chlorobenzyl)mercapto-1,3,4-thiadiazol-2-yl | —SCH₂— | H,H,H | Methoxy | Methoxy | trans | oil; 5.37 |
| 1a.530 | 5-(3-Chlorobenzyl)mercapto-1,3,4-thiadiazol-2-yl | —SCH₂— | H,H,H | Methoxy | Methoxy | trans | oil; 5.38 |
| 1a.531 | 5-(2,4-Dichlorobenzyl)mercapto-1,3,4-thiadiazol-2-yl | —SCH₂— | H,H,H | Methoxy | Methoxy | trans | oil; 5.38 |
| 1a.532 | 5-(3,4-Dichlorobenzyl)mercapto-1,3,4-thiadiazol-2-yl | —SCH₂— | H,H,H | Methoxy | Methoxy | trans | oil; 5.38 |
| 1a.533 | 5-(2,6-Dichlorobenzyl)mercapto-1,3,4-thiadiazol-2-yl | —SCH₂— | H,H,H | Methoxy | Methoxy | trans | oil; 5.40 |
| 1a.534 | 5-(2-Fluoro-6-chlorobenzyl)mercapto-1,3,4-thiadiazol-2-yl | —SCH₂— | H,H,H | Methoxy | Methoxy | trans | oil; 5.40 |
| 1a.535 | 5-(2-Naphthylmethyl)mercapto-1,3,4-thiadiazol-2-yl | —SCH₂— | H,H,H | Methoxy | Methoxy | trans | oil; 5.35 |
| 1a.536 | 5-(3-Phenoxybenzyl)mercapto-1,3,4-thiadiazol-2-yl | —SCH₂— | H,H,H | Methoxy | Methoxy | trans | oil; 5.38 |
| 1a.537 | 5-(4-Phenylbenzyl)mercapto-1,3,4-thiadiazol-2-yl | —SCH₂— | H,H,H | Methoxy | Methoxy | trans | oil; 5.39 |
| 1a.538 | 5-[4-(2-Chloro-4-CF₃-Phenoxy)benzyl]-mercapto-1,3,4-thiadiazol-2-yl | —SCH₂— | H,H,H | Methoxy | Methoxy | trans | oil; 5.40 |
| 1a.539 | 3-(6-Methylpyrid-2-yl)-isoxazol-5-yl | (E)—HC═CH— | H,H,H | Methoxy | Methoxy | trans | 103-105; 5.49 |
| 1a.540 | 3-(4-Chlorophenyl)-1,2,4-oxadiazol-5-yl | (E)—HC═CH— | H,H,H | Methoxy | Methoxy | trans | 159-160; 5.51 |
| 1a.541 | 3-Isobutyl-5-methyl-4,5-dihydroisoxazol-5-yl | (E)—HC═CH— | H,H,H | Methoxy | Methoxy | trans | oil; 5.38 |
| 1a.542 | 3-Chlorophenyl | —C(CH₃)═N—O—CH₂ | H,H,H | Methoxy | Methoxy | trans | oil; 5.37 |
| 1a.543 | 4-Methylphenyl | —C(CH₃)═N—O—CH₂ | H,H,H | Methoxy | Methoxy | trans | oil; 5.36 |
| 1a.544 | 4-Methoxyphenyl | —C(CH₃)═N—O—CH₂ | H,H,H | Methoxy | Methoxy | trans | oil; 5.37 |
| 1a.545 | Benzoyl | —C(CH₃)═N—O—CH₂ | H,H,H | Methoxy | Methoxy | trans | oil; 5.35 |

TABLE 1a-continued

Compounds of the formula 1a

1a

| Comp. no. | R29— | —A— | U,V,W | R1—Xm— | —Y | Isomer | m.p.; 1H–NMR (°C.) (ppm) |
|---|---|---|---|---|---|---|---|
| 1a.546 | 3-Cyanophenyl | —C(CH3)=N—O—CH2 | H,H,H | Methoxy | Methoxy | trans | oil; 5.39 |
| 1a.547 | Indan-1-yl | —C(CH3)=N—O—CH2 | H,H,H | Methoxy | Methoxy | trans | oil; 5.35 |
| 1a.548 | Thiophen-3-yl | —C(CH3)=N—O—CH2 | H,H,H | Methoxy | Methoxy | trans | oil; 5.33 |
| 1a.549 | 3-Nitrophenyl | —C(CH3)=N—O—CH2 | H,H,H | Methoxy | Methoxy | trans | oil; 5.40 |
| 1a.550 | Cyclohexyl | —C(CH3)=N—O—CH2 | H,H,H | Methoxy | Methoxy | trans | oil; 5.34 |
| 1a.551 | Thiophen-2-yl | —C(CH3)=N—O—CH2 | H,H,H | Methoxy | Methoxy | trans | oil; 5.34 |
| 1a.552 | Diphenylmethyl | —C(CH3)=N—O—CH2 | H,H,H | Methoxy | Methoxy | trans | oil; 5.33 |
| 1a.553 | 2-Methylfuran-5-yl | —C(CH3)=N—O—CH2 | H,H,H | Methoxy | Methoxy | trans | oil; 5.33 |
| 1a.554 | 3-Acetylphenyl | —C(CH3)=N—O—CH2 | H,H,H | Methoxy | Methoxy | trans | oil; 5.39 |
| 1a.555 | 3-[(Methoxycarbonyl)amino]-phenyl | —C(CH3)=N—O—CH2 | H,H,H | Methoxy | Methoxy | trans | oil; 5.37 |
| 1a.556 | 3-[(N-Methoxy-N-methylamino)-carbonyl]amino]-phenyl | —C(CH3)=N—O—CH2 | H,H,H | Methoxy | Methoxy | trans | oil; 5.38 |
| 1a.557 | 2-(2-Methylthiazol-4-yl)-thiazol-4-yl | (E)—HC=CH— | H,H,H | Methoxy | Methoxy | trans | 163–165; 5.49 |
| 1a.558 | 2-Phenyl-eth-1-yl | (E)—HC=CH— | H,H,H | Methoxy | Methoxy | trans | oil; 5.35 |
| 1a.559 | Phenyl | —CO—O—CH2 | H,H,H | Methoxy | Methoxy | trans | oil; 5.35 |
| 1a.560 | Benzyl | —CO—O—CH2 | H,H,H | Methoxy | Methoxy | trans | oil; 5.35 |
| 1a.561 | 2-Phenylethen-1-yl | —CO—O—CH2 | H,H,H | Methoxy | Methoxy | trans | oil; 5.38 |
| 1a.562 | trans-2,2-Dimethyl-3-(2,2-dibromethen-1-yl)-cyclopropan-1-yl | —CO—O—CH2 | H,H,H | Methoxy | Methoxy | trans | oil; 5.37 |
| 1a.563 | 1-Methyl-cycloprop-1-yl | —CO—O—CH2 | H,H,H | Methoxy | Methoxy | trans | oil; 5.36 |
| 1a.564 | 4-(4-Nitrophenoxy)-phenyl | —CO—O—CH2 | H,H,H | Methoxy | Methoxy | trans | oil; 5.37 |
| 1a.565 | 1-(4-Chlorophenyl)-cycloprop-1-yl | —CO—O—CH2 | H,H,H | Methoxy | Methoxy | trans | oil; 5.31 |
| 1a.566 | 4-Benzoylphenyl | —CO—O—CH2 | H,H,H | Methoxy | Methoxy | trans | oil; 5.40 |
| 1a.567 | 4-(4-Methylphenoxy)-phenyl | —CO—O—CH2 | H,H,H | Methoxy | Methoxy | trans | oil; 5.35 |
| 1a.568 | 3-(3-Chloropyridazin-6-yloxy)-phenyl | —CO—O—CH2 | H,H,H | Methoxy | Methoxy | trans | oil; 5.35 |
| 1a.569 | 2-(4-tert.-Butylphenyl)-ethen-1-yl | —CO—O—CH2 | H,H,H | Methoxy | Methoxy | trans | oil; 5.39 |
| 1a.570 | Biphenyl-4-yl | —CO—O—CH2 | H,H,H | Methoxy | Methoxy | trans | oil; 5.38 |

TABLE 1b
Compounds of the formula 1b
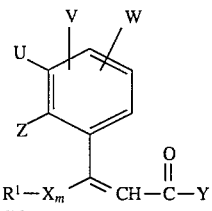
| Comp. no. | 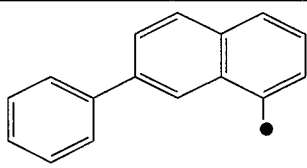 | R¹—Xₘ— | —Y | Isomer | m.p. (°C.); ¹H—NMR (ppm) |
|---|---|---|---|---|---|
| 1b.1 | 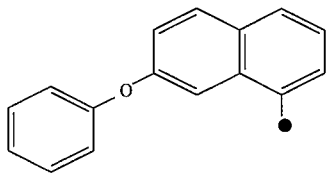 | Methoxy | Methoxy | trans | 62–64 → 5.61 |
| 1b.2 | 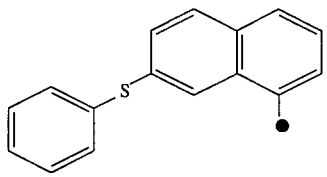 | Methoxy | Methoxy | trans | |
| 1b.3 | 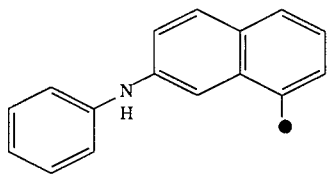 | Methoxy | Methoxy | trans | |
| 1b.4 | 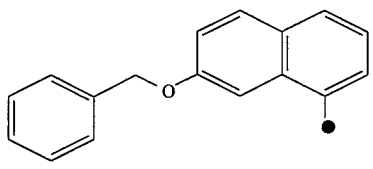 | Methoxy | Methoxy | trans | |
| 1b.5 | 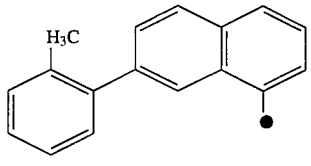 | Methoxy | Methoxy | trans | |
| 1b.6 |  | Methoxy | Methoxy | trans | |

TABLE 1b-continued
Compounds of the formula 1b
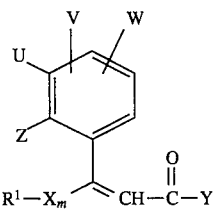
| Comp. no. | 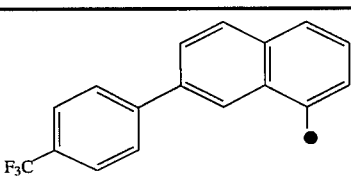 | $R^1$—$X_m$— | —Y | Isomer | m.p. (°C.); $^1$H—NMR (ppm) |
|---|---|---|---|---|---|
| 1b.7 | 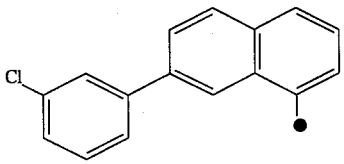 | Methoxy | Methoxy | trans | |
| 1b.8 | 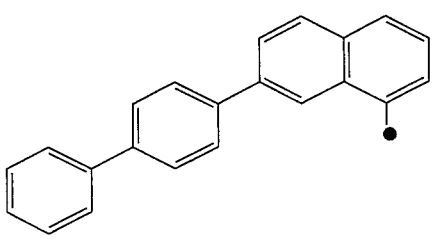 | Methoxy | Methoxy | trans | |
| 1b.9 | 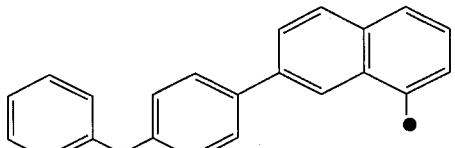 | Methoxy | Methoxy | trans | 96–98 → 5.61 |
| 1b.10 | 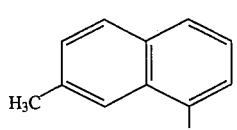 | Methoxy | Methoxy | trans | oil → 5.60 |
| 1b.11 | 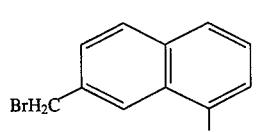 | Methoxy | Methoxy | trans | oil → 5.58 |
| 1b.12 | 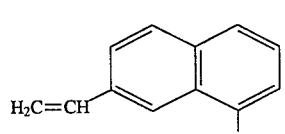 | Methoxy | Methoxy | trans | |
| 1b.13 |  | Methoxy | Methoxy | trans | |

TABLE 1b-continued
Compounds of the formula 1b
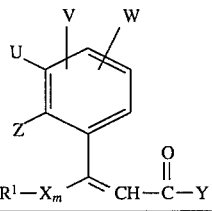
| Comp. no. | | $R^1-X_m-$ | $-Y$ | Isomer | m.p. (°C.); $^1H-$NMR (ppm) |
|---|---|---|---|---|---|
| 1b.14 | 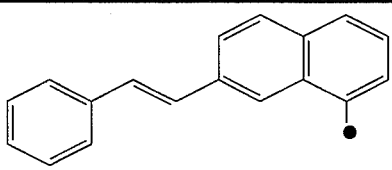 | Methoxy | Methoxy | trans | |
| 1b.15 | 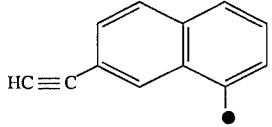 | Methoxy | Methoxy | trans | 95–97 → 5.58 |
| 1b.16 | 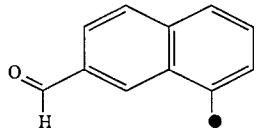 | Methoxy | Methoxy | trans | |
| 1b.17 | 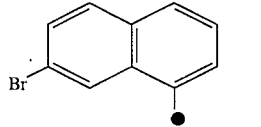 | Methoxy | Methoxy | trans | 111–113 → 5.58 |
| 1b.18 | 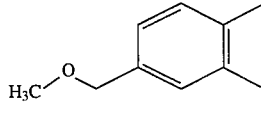 | Methoxy | Methoxy | trans | |
| 1b.19 | 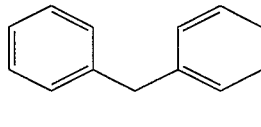 | Methoxy | Methoxy | trans | |
| 1b.20 | 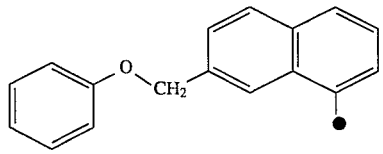 | Methoxy | Methoxy | trans | oil → 5.56 |

TABLE 1b-continued
Compounds of the formula 1b
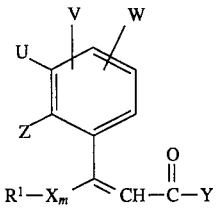
| Comp. no. | | $R^1-X_m-$ | $-Y$ | Isomer | m.p. (°C.); $^1H$—NMR (ppm) |
|---|---|---|---|---|---|
| 1b.21 | 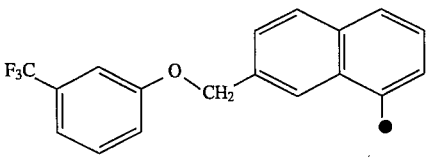 | Methoxy | Methoxy | trans | |
| 1b.22 | 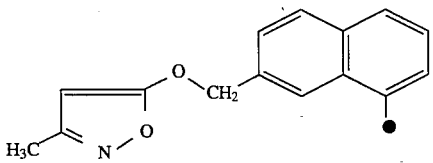 | Methoxy | Methoxy | trans | |
| 1b.23 | 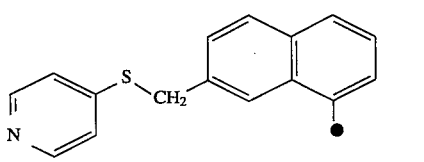 | Methoxy | Methoxy | trans | |
| 1b.24 | 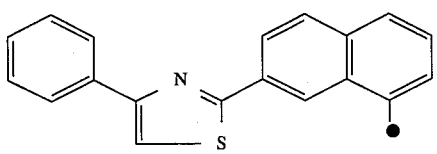 | Methoxy | Methoxy | trans | |
| 1b.25 | 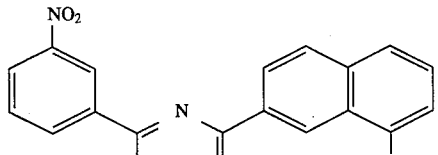 | Methoxy | Methoxy | trans | |
| 1b.26 | 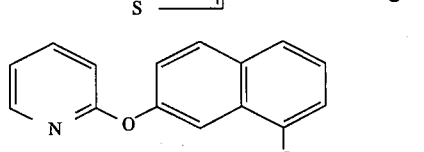 | Methoxy | Methoxy | trans | |

TABLE 1b-continued

Compounds of the formula 1b

| Comp. no. | (structure with Z) | $R^1-X_m-$ | $-Y$ | Isomer | m.p. (°C.); $^1$H—NMR (ppm) |
|---|---|---|---|---|---|
| 1b.27 | isoxazoline-pyridine group; naphthyl | Methoxy | Methoxy | trans | |
| 1b.28 | CH₃-C(=N-O-N=CH-)-; naphthyl | Methoxy | Methoxy | trans | |
| 1b.29 | CH₃-C(=N-)-oxadiazole; naphthyl | Methoxy | Methoxy | trans | |
| 1b.30 | phenyl-thiophene; naphthyl | Methoxy | Methoxy | trans | |
| 1b.31 | ethyl-isoxazole; naphthyl | Methoxy | Methoxy | trans | |
| 1b.32 | CH₃-C(=N-N=)-oxadiazole; naphthyl | Methoxy | Methoxy | trans | |

TABLE 1b-continued

Compounds of the formula 1b

| Comp. no. | [structure] | R¹—Xₘ— | —Y | Isomer | m.p. (°C.); ¹H—NMR (ppm) |
|---|---|---|---|---|---|
| 1b.33 | [5-methyl-1,3,4-thiadiazol-2-yl naphthyl] | Methoxy | Methoxy | trans | |
| 1b.34 | [pyrimidin-2-yl naphthyl] | Methoxy | Methoxy | trans | |
| 1b.35 | [1,2,4-triazol-1-yl naphthyl] | Methoxy | Methoxy | trans | |
| 1b.36 | [1-methylpyrazol naphthyl] | Methoxy | Methoxy | trans | |
| 1b.37 | [1-methylimidazol naphthyl] | Methoxy | Methoxy | trans | |
| 1b.38 | [2-cyanophenyl-pyrazolyl naphthyl] | Methoxy | Methoxy | trans | |
| 1b.39 | [6-methylpyridazin-3-yl naphthyl] | Methoxy | Methoxy | trans | |

TABLE 1b-continued

Compounds of the formula 1b

| Comp. no. | [structure] | $R^1-X_m-$ | $-Y$ | Isomer | m.p. (°C.); $^1H-NMR$ (ppm) |
|---|---|---|---|---|---|
| 1b.40 | | Methoxy | Methoxy | trans | |
| 1b.41 | | Methoxy | Methoxy | trans | |
| 1b.42 | | Methoxy | Methoxy | trans | |
| 1b.43 | | Methoxy | Methoxy | trans | |
| 1b.44 | | Methoxy | Methoxy | trans | |
| 1b.45 | | Methoxy | Methoxy | trans | |

TABLE 1b-continued
Compounds of the formula 1b
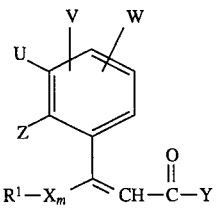
| Comp. no. | | $R^1-X_m-$ | $-Y$ | Isomer | m.p. (°C.); $^1H$—NMR (ppm) |
|---|---|---|---|---|---|
| 1b.46 | 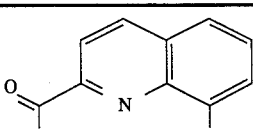 | Methoxy | Methoxy | trans | |
| 1b.47 | 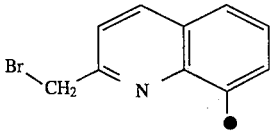 | Methoxy | Methoxy | trans | |
| 1b.48 | 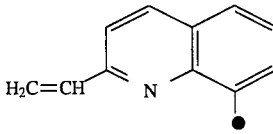 | Methoxy | Methoxy | trans | |
| 1b.49 | 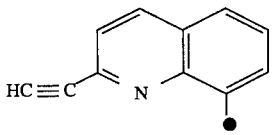 | Methoxy | Methoxy | trans | |
| 1b.50 | 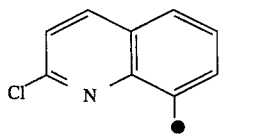 | Methoxy | Methoxy | trans | |
| 1b.51 | 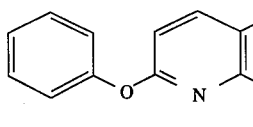 | Methoxy | Methoxy | trans | |
| 1b.52 | 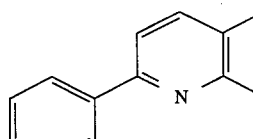 | Methoxy | Methoxy | trans | |
| 1b.53 | 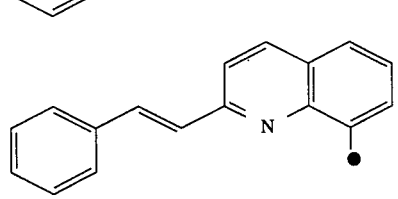 | Methoxy | Methoxy | trans | |

TABLE 1b-continued
Compounds of the formula 1b
| Comp. no. | [structure with U, V, W, Z] | $R^1-X_m-$ | $-Y$ | Isomer | m.p. (°C.); $^1H-NMR$ (ppm) |
|---|---|---|---|---|---|
| 1b.54 | 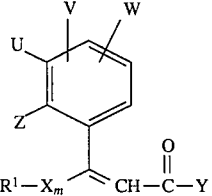 | Methoxy | Methoxy | trans | |
| 1b.55 | 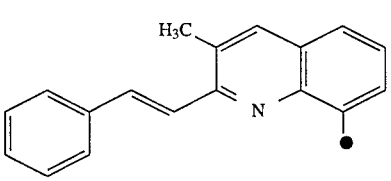 | Methoxy | Methoxy | trans | |
| 1b.56 | 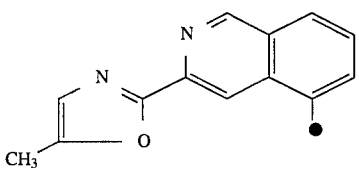 | Methoxy | Methoxy | trans | |
| 1b.57 | 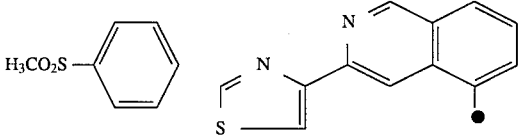 | Methoxy | Methoxy | trans | |
| 1b.58 | 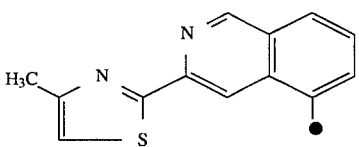 | Methoxy | Methoxy | trans | |
| 1b.59 | 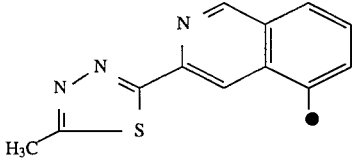 | Methoxy | Methoxy | trans | |
| 1b.60 | 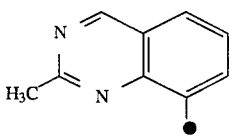 | Methoxy | Methoxy | trans | |

TABLE 1b-continued

Compounds of the formula 1b

[Structure: substituted phenyl with U, V, W, Z and R¹-Xₘ-C(=CH-C(=O)-Y)- group] 1b

| Comp. no. | [aryl structure with U, V, W, Z] | R¹—Xₘ— | —Y | Isomer | m.p. (°C.); ¹H—NMR (ppm) |
|---|---|---|---|---|---|
| 1b.61 | 4-bromophenyl; quinazolin-8-yl | Methoxy | Methoxy | trans | |
| 1b.62 | 3-(trifluoromethyl)phenyl-C(=N-)-S (thiazole linkage); quinazolin-8-yl | Methoxy | Methoxy | trans | |
| 1b.63 | 2,5-dimethylphenyl-O-CH₂-; quinolin-5-yl | Methoxy | Methoxy | trans | |
| 1b.64 | phenyl; quinolin-5-yl | Methoxy | Methoxy | trans | |
| 1b.65 | phenyl-C(=N-)-S (thiazole); quinolin-5-yl | Methoxy | Methoxy | trans | |
| 1b.66 | 3-methylquinolin-5-yl | Methoxy | Methoxy | trans | |

TABLE 1b-continued
Compounds of the formula 1b
| Comp. no. | (structure) | $R^1-X_m-$ | $-Y$ | Isomer | m.p. (°C.); $^1H$—NMR (ppm) |
|---|---|---|---|---|---|
| 1b.67 | 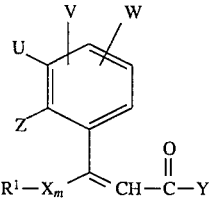 | Methoxy | Methoxy | trans | |
| 1b.68 | 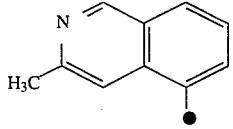 | Methoxy | Methoxy | trans | |
| 1b.69 | 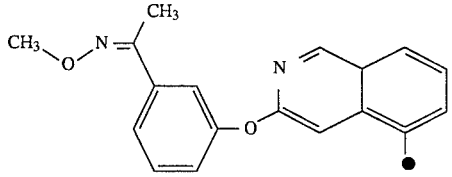 | Methoxy | Methoxy | trans | |
| 1b.70 | 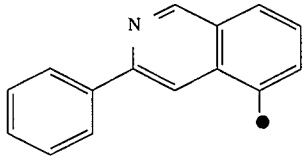 | Methoxy | Methoxy | trans | |
| 1b.71 | 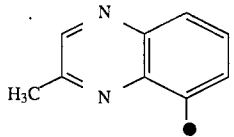 | Methoxy | Methoxy | trans | |
| 1b.72 | 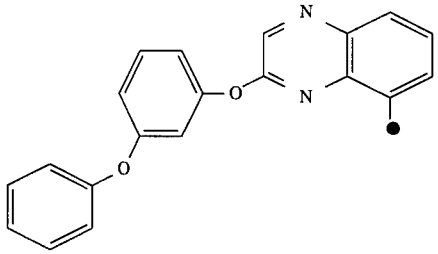 | Methoxy | Methoxy | trans | |

TABLE 1b-continued

Compounds of the formula 1b

| Comp. no. | [U,V,W,Z substituent structure] | R¹—Xₘ— | —Y | Isomer | m.p. (°C.); ¹H—NMR (ppm) |
|---|---|---|---|---|---|
| 1b.73 | quinoxaline with 4-biphenyl substituent | Methoxy | Methoxy | trans | |
| 1b.74 | benzotriazine with CH₃ substituent | Methoxy | Methoxy | trans | |
| 1b.75 | benzotriazine with —CH₂—O—(4-phenoxyphenyl) substituent | Methoxy | Methoxy | trans | |
| 1b.76 | cinnoline with O-(3-cyanophenyl) substituent | Methoxy | Methoxy | trans | |
| 1b.77 | cinnoline with —CH₂—O-(2-methylphenyl) substituent | Methoxy | Methoxy | trans | |
| 1b.78 | cinnoline with 3-chlorophenyl substituent | Methoxy | Methoxy | trans | |
| 1b.79 | H₃C—C= substituent | Methoxy | Methoxy | trans | |

TABLE 1b-continued

Compounds of the formula 1b

| Comp. no. | [structure] | $R^1-X_m-$ | $-Y$ | Isomer | m.p. (°C.); $^1H-NMR$ (ppm) |
|---|---|---|---|---|---|
| 1b.80 | [phenyl-CH2-C(=)- fused to benzene] | Methoxy | Methoxy | trans | |
| 1b.81 | [phenyl-C(=)-CH fused to benzene (indene)] | Methoxy | Methoxy | trans | |
| 1b.82 | [phenyl-C(=)- fused benzothiophene] | Methoxy | Methoxy | trans | |
| 1b.83 | [H3C-C(=)- fused benzothiophene] | Methoxy | Methoxy | trans | |
| 1b.84 | [H3C-C(=)- fused benzofuran] | Methoxy | Methoxy | trans | |
| 1b.85 | [OHC-C(=)- fused benzofuran] | Methoxy | Methoxy | trans | |
| 1b.86 | [BrH2C-C(=)- fused benzofuran] | Methoxy | Methoxy | trans | |
| 1b.87 | [H2C=CH-C(=)- fused benzofuran] | Methoxy | Methoxy | trans | |

TABLE 1b-continued
Compounds of the formula 1b
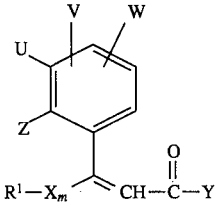
| Comp. no. | 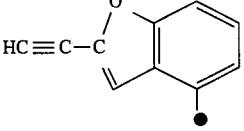 | $R^1-X_m-$ | $-Y$ | Isomer | m.p. (°C.); $^1H$—NMR (ppm) |
|---|---|---|---|---|---|
| 1b.88 | 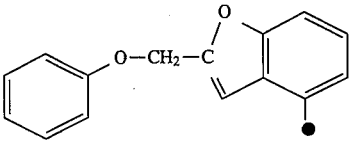 | Methoxy | Methoxy | trans | |
| 1b.89 | 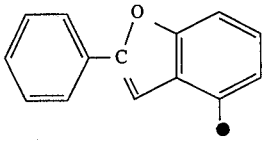 | Methoxy | Methoxy | trans | |
| 1b.90 | 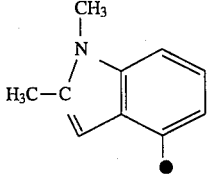 | Methoxy | Methoxy | trans | |
| 1b.91 | 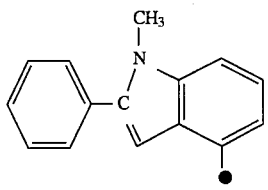 | Methoxy | Methoxy | trans | |
| 1b.92 | 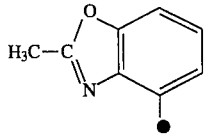 | Methoxy | Methoxy | trans | |
| 1b.93 | 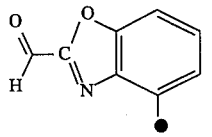 | Methoxy | Methoxy | trans | |
| 1b.94 | | Methoxy | Methoxy | trans | |

TABLE 1b-continued
Compounds of the formula 1b
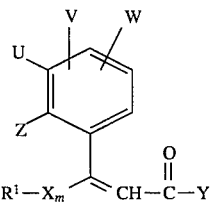
| Comp. no. | | $R^1-X_m-$ | $-Y$ | Isomer | m.p. (°C.); $^1H$—NMR (ppm) |
|---|---|---|---|---|---|
| 1b.95 | 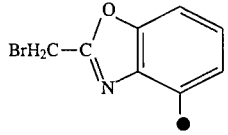 | Methoxy | Methoxy | trans | |
| 1b.96 | 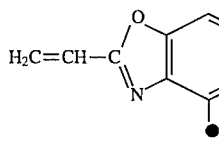 | Methoxy | Methoxy | trans | |
| 1b.97 | 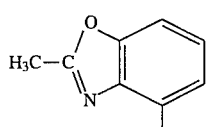 | Methoxy | Methoxy | trans | |
| 1b.98 | 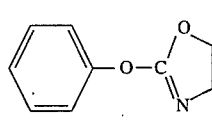 | Methoxy | Methoxy | trans | |
| 1b.99 | 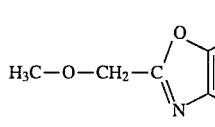 | Methoxy | Methoxy | trans | |
| 1b.100 | 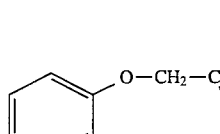 | Methoxy | Methoxy | trans | |
| 1b.101 | 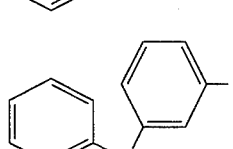 | Methoxy | Methoxy | trans | |
| 1b.102 | 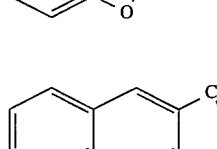 | Methoxy | Methoxy | trans | |

TABLE 1b-continued
Compounds of the formula 1b
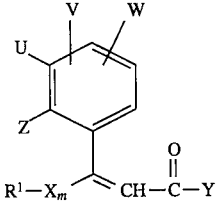
| Comp. no. | 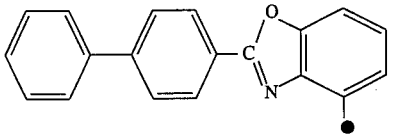 | R¹—Xₘ— | —Y | Isomer | m.p. (°C.); ¹H—NMR (ppm) |
|---|---|---|---|---|---|
| 1b.103 | 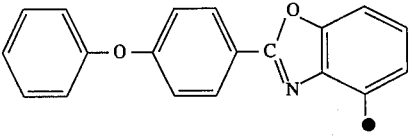 | Methoxy | Methoxy | trans | |
| 1b.104 | 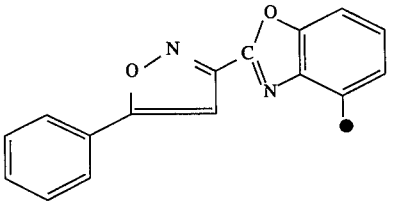 | Methoxy | Methoxy | trans | |
| 1b.105 | 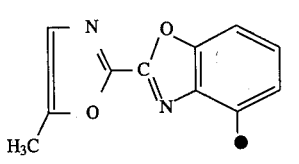 | Methoxy | Methoxy | trans | |
| 1b.106 | 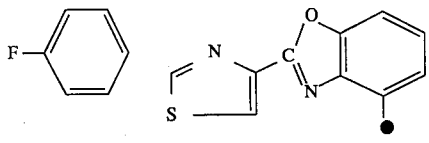 | Methoxy | Methoxy | trans | |
| 1b.107 | 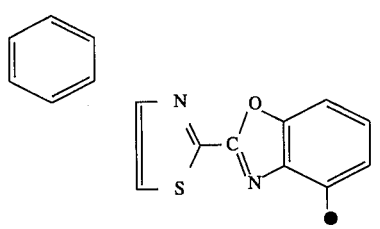 | Methoxy | Methoxy | trans | |
| 1b.108 | | Methoxy | Methoxy | trans | |

TABLE 1b-continued

Compounds of the formula 1b

| Comp. no. | (structure) | R¹—X_m— | —Y | Isomer | m.p. (°C.); ¹H—NMR (ppm) |
|---|---|---|---|---|---|
| 1b.109 | (N=N, CH₃-CH-CH₃, S-oxazole-benzoxazole) | Methoxy | Methoxy | trans | |
| 1b.110 | (phenyl, thiophene-benzoxazole) | Methoxy | Methoxy | trans | |
| 1b.111 | (pyridine-oxazole-benzoxazole) | Methoxy | Methoxy | trans | |
| 1b.112 | (H₃C-benzothiazole) | Methoxy | Methoxy | trans | |
| 1b.113 | (Cl-phenyl-benzothiazole) | Methoxy | Methoxy | trans | |
| 1b.114 | (H₅C₂-oxazole-benzothiazole) | Methoxy | Methoxy | trans | |
| 1b.115 | (Br-phenyl-thiazole-benzothiazole) | Methoxy | Methoxy | trans | |

TABLE 1b-continued
Compounds of the formula 1b
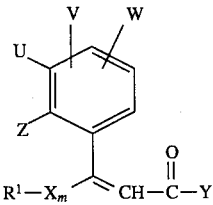
| Comp. no. | 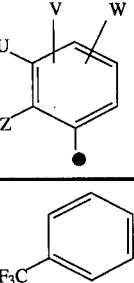 | $R^1—X_m—$ | —Y | Isomer | m.p. (°C.); $^1$H—NMR (ppm) |
|---|---|---|---|---|---|
| 1b.116 | 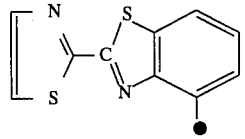 | Methoxy | Methoxy | trans | |
| 1b.117 | 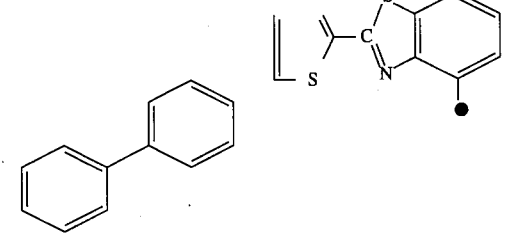 | Methoxy | Methoxy | trans | |
| 1b.118 | 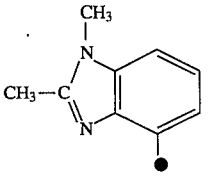 | Methoxy | Methoxy | trans | |
| 1b.119 | 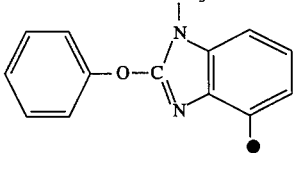 | Methoxy | Methoxy | trans | |
| 1b.120 | 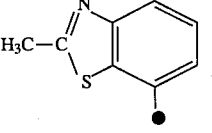 | Methoxy | Methoxy | trans | |
| 1b.121 | 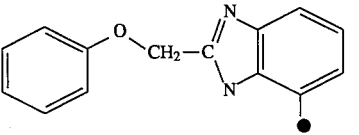 | Methoxy | Methoxy | trans | |

TABLE 1b-continued

Compounds of the formula 1b

| Comp. no. | [structure] | $R^1-X_m-$ | $-Y$ | Isomer | m.p. (°C.); $^1H$—NMR (ppm) |
|---|---|---|---|---|---|
| 1b.122 | 2-phenyl-benzimidazol-7-yl | Methoxy | Methoxy | trans | |
| 1b.123 | 2-methyl-benzoxazol-7-yl | Methoxy | Methoxy | trans | |
| 1b.124 | 2-(bromomethyl)-benzoxazol-7-yl | Methoxy | Methoxy | trans | |
| 1b.125 | 2-phenoxy-benzoxazol-7-yl | Methoxy | Methoxy | trans | |
| 1b.126 | 2-(phenoxymethyl)-benzo[1,3]dioxol-4-yl | Methoxy | Methoxy | trans | |
| 1b.127 | 2-phenyl-benzoxazol-7-yl | Methoxy | Methoxy | trans | |
| 1b.128 | 2-styryl-benzoxazol-7-yl | Methoxy | Methoxy | trans | |
| 1b.129 | 2-(5-methyl-oxazol-2-yl)-benzoxazol-7-yl | Methoxy | Methoxy | trans | |

TABLE 1b-continued
Compounds of the formula 1b
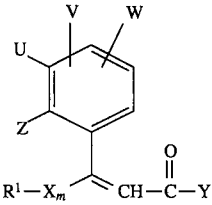
| Comp. no. | | $R^1-X_m-$ | $-Y$ | Isomer | m.p. (°C.); $^1H$—NMR (ppm) |
|---|---|---|---|---|---|
| 1b.130 | 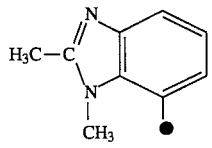 | Methoxy | Methoxy | trans | |
| 1b.131 | 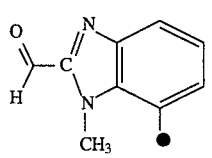 | Methoxy | Methoxy | trans | |
| 1b.132 | 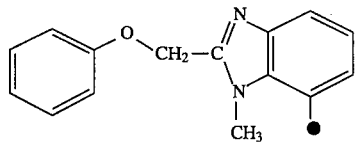 | Methoxy | Methoxy | trans | |
| 1b.133 | 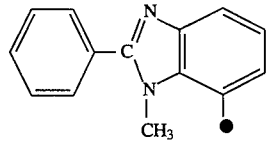 | Methoxy | Methoxy | trans | |
| 1b.134 | 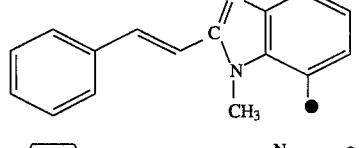 | Methoxy | Methoxy | trans | |
| 1b.135 | 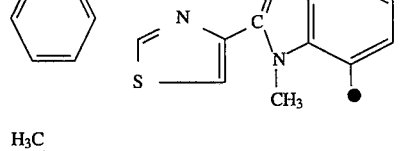 | Methoxy | Methoxy | trans | |
| 1b.136 | 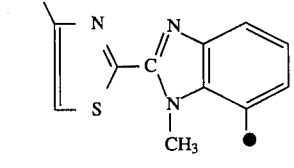 | Methoxy | Methoxy | trans | |

TABLE 1b-continued

Compounds of the formula 1b

| Comp. no. | (aryl group) | R¹—Xₘ— | —Y | Isomer | m.p. (°C.); ¹H—NMR (ppm) |
|---|---|---|---|---|---|
| 1b.137 | benzimidazole with N—N, S, H₃C, CH₃ substituents | Methoxy | Methoxy | trans | 96–97 → 5.25 |
| 1b.138 | 6-methylnaphthalen-1-yl | Methoxy | Methoxy | cis | oil; 5.23 |
| 1b.139 | naphthalenyl with CH₃—O—CH= substituent | Methoxy | Methoxy | trans | oil; 5.58 |
| 1b.140 | naphthalenyl with thiazoline substituent | Methoxy | Methoxy | trans | oil; 5.62 |
| 1b.141 | naphthalenyl with phenyl-oxazole-CH₃ substituent | Methoxy | Methoxy | trans | oil; 5.66 |
| 1b.142 | naphthalenyl with 3-(4-fluorophenyl)isoxazol-5-yl substituent | Methoxy | Methoxy | trans | 155–158; 5.67 |

TABLE 1b-continued

Compounds of the formula 1b

| Comp. no. | [structure] | R¹—X$_m$— | —Y | Isomer | m.p. (°C); $^1$H—NMR (ppm) |
|---|---|---|---|---|---|
| 1b.143 | | Methoxy | Methoxy | trans | 190–192; 5.63 |
| 1b.144 | | Methoxy | Methoxy | trans | oil; 5.60 |
| 1b.145 | | Methoxy | Methoxy | cis | oil; 5.25 |
| 1b.146 | | Methoxy | Methoxy | cis | oil; 5.24 |
| 1b.147 | | Methoxy | Methoxy | trans | oil; 5.61 |

TABLE 1b-continued
Compounds of the formula 1b
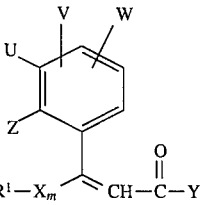
| Comp. no. | 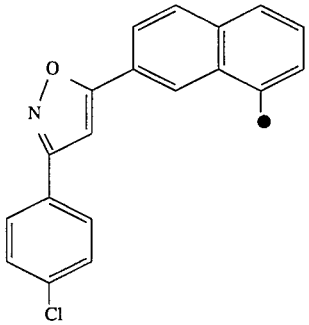 | R¹—X$_m$— | —Y | Isomer | m.p. (°C.); ¹H—NMR (ppm) |
|---|---|---|---|---|---|
| 1b.148 | 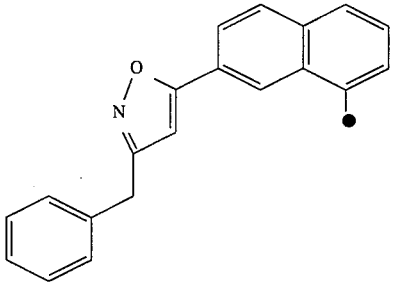 | Methoxy | Methoxy | trans | 184–187; 5.62 |
| 1b.149 | 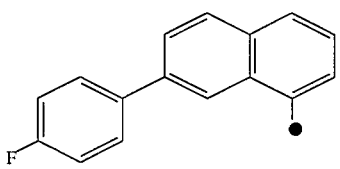 | Methoxy | Methoxy | trans | oil; 5.62 |
| 1b.150 | 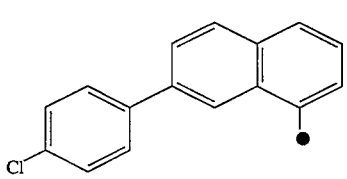 | Methoxy | Methoxy | cis | 65–67; 5.61 |
| 1b.151 | 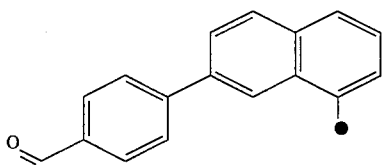 | Methoxy | Methoxy | cis | oil; 5.60 |
| 1b.152 | | Methoxy | Methoxy | cis | 102–105; 5.62 |

TABLE 1b-continued
Compounds of the formula 1b
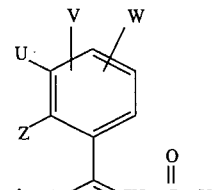
| Comp. no. | 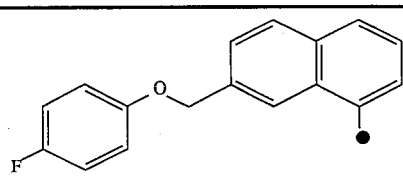 | $R^1-X_m-$ | $-Y$ | Isomer | m.p. (°C.); $^1H$—NMR (ppm) |
|---|---|---|---|---|---|
| 1b.153 | 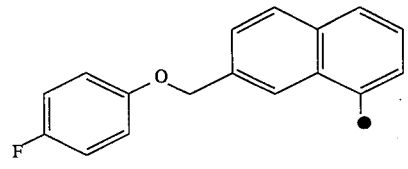 | Methoxy | Methoxy | trans | 93–95; 5.58 |
| 1b.154 | 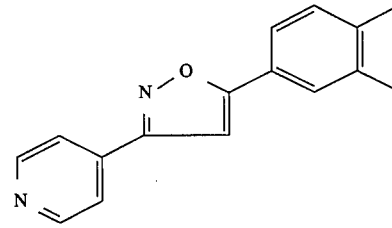 | Methoxy | Methoxy | cis | oil; 5.24 |
| 1b.155 | 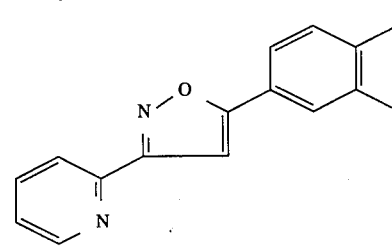 | Methoxy | Methoxy | trans | oil; 5.68 |
| 1b.156 | 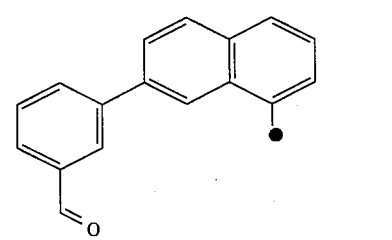 | Methoxy | Methoxy | trans | 114–116; 5.67 |
| 1b.157 |  | Methoxy | Methoxy | trans | oil; 5.63 |

TABLE 1b-continued
Compounds of the formula 1b
| Comp. no. | (structure) | $R^1-X_m-$ | $-Y$ | Isomer | m.p. (°C.); $^1H$—NMR (ppm) |
|---|---|---|---|---|---|
| 1b.158 | 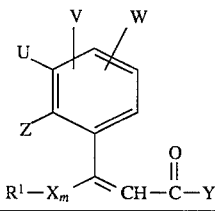 | Methoxy | Methoxy | trans | oil; 5.61 |
| 1b.159 | 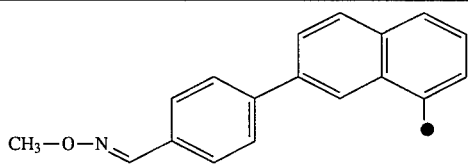 | Methoxy | Methoxy | trans | oil; 5.60 |
| 1b.160 | 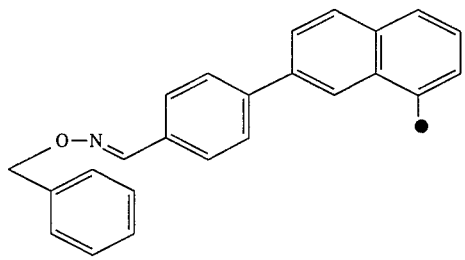 | Methoxy | Methoxy | trans | 154–155; 5.67 |
| 1b.161 | 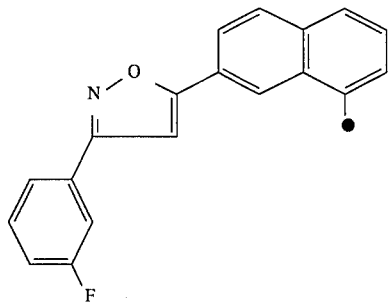 | Methoxy | Methoxy | trans | 144–146; 5.67 |
| 1b.162 | 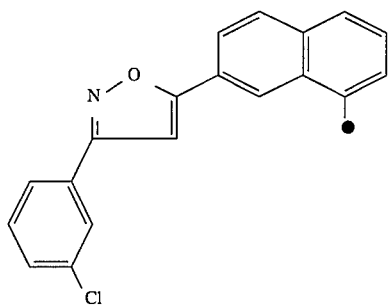 | Methoxy | Methoxy | trans | oil; 5.56 |

TABLE 1b-continued

Compounds of the formula 1b

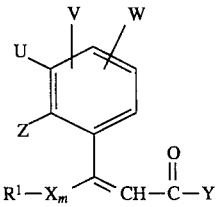

| Comp. no. | 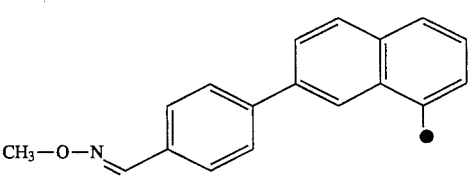 | $R^1-X_m-$ | $-Y$ | Isomer | m.p. (°C.); $^1H$—NMR (ppm) |
|---|---|---|---|---|---|
| 1b.163 | 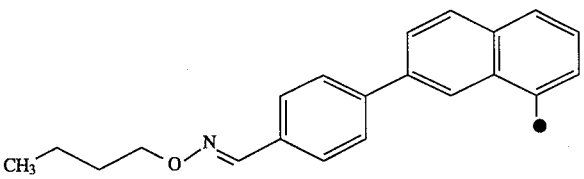 | Methoxy | Amino | trans | 181; 5.61 |
| 1b.164 | 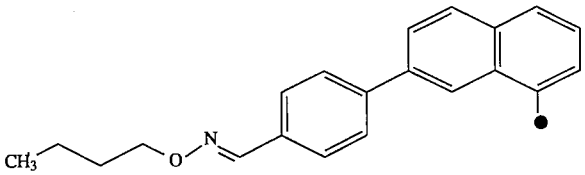 | Methoxy | Amino | trans | oil; 5.58 |
| 1b.165 | 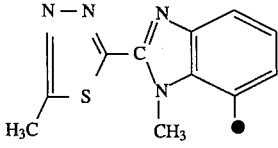 | Methoxy | Amino | cis | oil; 5.25 |
| 1b.166 |  | Methoxy | Methoxy | trans | |

It is known that inhibitors of the mitochondrial respiration of fungi can be used as fungicides, e.g., antimycin (cf. U.S. Rieske in M. Erecinska, D. F. Wilson (ed.) "Inhibitors of Mitochondrial Function", Pergamon Press, Oxford, 1981, p. 110). However, there are various drawbacks to the use of antimycin, e.g., its production is difficult and elaborate, and it is insufficiently stable when used in the open.

The cinnamic acid derivatives according to the invention inhibit the mitochondrial respiration of fungi (v. Use Example 1) and may be used as fungicides.

Mitochondrial respiration is essential for metabolism. With the aid of respiration, energy is stored in the mitochondria in the form of adenosine triphosphate (ATP). The inhibition of respiration caused by mitochondrial respiration inhibitors ultimately results in the inhibition of ATP formation. As a consequence, metabolic processes dependent on ATP or energy come to a stop in fungi treated with β-substituted cinnamic acid derivatives according to the invention, growth coming to a standstill or the fungi dying.

Further, the compounds according to the invention may also be used as animal or human antimycotics, as the mitochondrial respiration of animal-pathogenic and human-pathogenic fungi is inhibited. Some of the compounds are also effective on insects and spinning mites, as mitochondrial respiration is also inhibited in these organisms (v. Use Example 1).

Certain β-aryl-substituted cinnamides having a fungicidal action, e.g., β-phenylcinnamyl morpholide, are known from German Offenlegungsschrift 33 06 996. However, these compounds have virtually no effect on the mitochondrial respiration of fungi (v. Use Example 1) and their fungicidal action on several fungi is unsatisfactory.

By contrast, the compounds according to the invention have a broad spectrum of action both on Phycomycetes and Ascomycetes, Basidiomycetes and Deuteromycetes.

The novel compounds are suitable for use as fungicides.

The compounds I according to the invention, or fungicidal agents containing them, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

Normally, the plants are sprayed or dusted with the active ingredients or the seeds of the crop plants are treated with the active ingredients.

The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as ligninsulfite waste liquors and methylcellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acids, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, andureas, and vegetable products such as grain meals, bark meal, wood meal, and nutshell meal, cellulosic powders, etc.

Examples of such formulations are:

I. A solution of 90 parts by weight of compound no. 1.38 and 10 parts by weight of N-methyl-α-pyrrolidone, which is suitable for application in the form of very fine drops.

II. A mixture of 20 parts by weight of compound no. 1a.108, 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By finely dispersing the mixture in water, an aqueous dispersion is obtained.

III. An aqueous dispersion of 20 parts by weight of compound no. 1a.2, 40 parts by weight of cyclohexanone, 30 parts by weight of isobutanol, 20 parts by weight of the adduct of 40 moles of ethylene oxide and 1 mole of castor oil.

IV. An aqueous dispersion of 20 parts by weight of compound no. 1.1, 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil.

V. A hammer-milled mixture of 80 parts by weight of compound no. 1a.108, 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel. By finely dispersing the mixture in water, a spray liquor is obtained.

VI. An intimate mixture of 3 parts by weight of compound no. 1a.2 and 97 parts by weight of particulate kaolin. The dust contains 3wt % of the active ingredient.

VII. An intimate mixture of 30 parts by weight of compound no. 1.1, 92 parts by weight of powdered silica gel and 8 parts by weight of paraffin oil sprayed onto the surface of this silica gel. This formulation of the active ingredient exhibits good adherence.

VIII. A stable aqueous dispersion of 40 parts by weight of compound no. 1a.2, 10 parts of the sodium salt of a phenolsulfonic acid-urea-formaldehyde condensate, 2 parts of silica gel and 48 parts of water, which dispersion can be further diluted.

IX. A stable oily dispersion of 20 parts by weight of compound no. 1b.1, 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil.

In general terms, the novel compounds are extremely effective on a broad spectrum of phytopathogenic fungi, in particular those from the class consisting of the Ascomycetes and Basidiomycetes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits, and the seeds of these plants.

The compounds are applied by spraying or dusting the plants with the active ingredients, or treating the seeds of the plants with the active ingredients. They may be applied before or after infection of the plants or seeds by the fungi.

The novel compounds I are particularly useful for controlling the following plant diseases:

*Erysiphe graminis* in cereals,

*Erysiphe cichoracearum* and *Sphaerotheca fuliginea* in cucurbits,

*Podosphaera leucotricha* in apples,

*Uncinula necator* in vines,

Puccinia species in cereals,

*Rhizoctonia solani* in cotton,

Ustilago species in cereals and sugar cane,

*Venturia inaequalis* (scab) in apples,

Helminthosporium species in cereals,

*Septoria nodorum* in wheat,

*Botrytis cinerea* (gray mold) in strawberries and grapes,

*Cercospora arachidicola* in groundnuts,

*Pseudocercosporella herpotrichoides* in wheat and barley,

*Pyricularia oryzae* in rice,

*Phytophthora infestans* in potatoes and tomatoes,

Fusarium and Verticillium species in various plants,
*Plasmopara viticola* in grapes,
Alternaria species in fruit and vegetables.

The novel compounds may also be used for protecting materials (timber), e.g., against Paecilomyces variotii.

The fungicidal agents generally contain from 0.1 to 95, and preferably from 0.5 to 90, wt % of active ingredient. The application rates depend on the type of effect desired, and vary from 0.02 to 3 kg/ha.

When the active ingredients are used for treating seed, active ingredient amounts of from 0.001 to 50, and preferably from 0.01 to 10, g per Kg of seed are generally required.

In these application forms, the agents according to the invention may also be present together with other active ingredients, for example herbicides, insecticides, growth regulators, and fungicides, and may furthermore be mixed and applied together with fertilizers. Admixture with other fungicides frequently results in a greater fungicidal action spectrum.

The following list of fungicides with which the novel compounds may be combined is intended to illustrate possible combinations but not to impose any restrictions.

Examples of fungicides which may be combined with the novel compounds are:

sulfur,
dithiocarbamates and their derivatives, such as
  ferric dimethyldithiocarbamate,
  zinc dimethyldithiocarbamate,
  zinc ethylenebisdithiocarbamate,
  manganese ethylenebisdithiocarbamate,
  manganese zinc ethylenediaminebisdithiocarbamate,
  tetramethylthiuram disulfides,
  ammonia complex of zinc N,N'-ethylenebisdithiocarbamate,
  ammonia complex of zinc N,N'-propylenebisdithiocarbamate,
  zinc N,N'-propylenebisdithiocarbamate and
  N,N'-polypropylenebis(thiocarbamyl) disulfide;
nitro derivatives, such as
  dinitro(1-methylheptyl)-phenyl crotonate,
  2-sec-butyl-4,6-dinitrophenyl 3,3-dimethylacrylate,
  2-sec-butyl-4,6-dinitrophenyl isopropylcarbonate and
  diisopropyl 5-nitroisophthalate;
heterocyclic substances, such as
  2-heptadecylimidazol-2-yl acetate,
  2,4-dichloro-6-(o-chloroanilino)-s-triazine,
  0,0-diethyl phthalimidophosphonothioate,
  5-amino-1-[-bis-(dimethylamino)-phosphinyl]-3-phenyl-1,2,4-triazole,
  2,3-dicyano-1,4-dithioanthraquinone,
  2-thio-1,3-dithio[4,5-b]quinoxaline,
  methyl 1-(butylcarbamyl)-2-benzimidazolecarbamate,
  2-methoxycarbonylaminobenzimidazole,
  2-(fur-2-yl)-benzimidazole,
  2-(thiazol-4-yl)benzimidazole,
  N-(1,1,2,2-tetrachloroethylthio)-tetrahydrophthalimide,
  N-trichloromethylthiotetrahydrophthalimide,
  N-trichloromethylthiophthalimide,
  N-dichlorofluoromethylthio-N',N'-dimethyl-N-phenylsulfuric acid diamide,
  5-ethoxy-3-trichloromethyl-1,2,3-thiadiazole,
  2-thiocyanatomethylthiobenzothiazole,
  1,4-dichloro-2,5-dimethoxybenzene,
  4-(2-chlorophenylhydrazono)-3-methyl-5-isoxazolone,
  2-thiopyridine 1-oxide,
  8-hydroxyquinoline and its copper salt,
  2,3-dihydro-5-carboxanilido-6-methyl-1,4-oxathiyne,
  2,3-dihydro-5-carboxanilido-6-methyl-1,4-oxathiyne 4,4-dioxide,
  2-methyl-5,6-dihydro-4H-pyran-3-carboxanilide,
  2-methylfuran-3-carboxanilide,
  2,5-dimethylfuran-3-carboxanlide,
  2,4,5-trimethylfuran-3-carboxanilide,
  2,5-dimethyl-N-cyclohexylfuran-3-carboxamide,
  N-cyclohexyl-N-methoxy-2,5-diethylfuran-3-carboxamide,
  2-methylbenzanlide,
  2-iodobenzanilide,
  N- formyl-N-morpholine-2,2,2-trichloroethylacetal,
  piperazine-1,4-diylbis-(1-(2,2,2-trichloroethyl)-formamide),
  1-(3,4-dichloroanilino)-1-formylamino-2,2,2-trichloroethane,
  2,6-dimethyl-N-tridecylmorpholine and its salts,
  2,6-dimethyl-N-cyclododecylmorpholine and its salts,
  N-[3-(p-tert.-butylphenyl)-2-methylpropyl]-cis-2,6-dimethylmorpholine,
  N-[3-(p-tert.-butylphenyl)-2-methylpropyl]-piperidine,
  1-[2-(2,4-dichlorophenyl)-4-ethyl-1,3-dioxolan-2-ylethyl]-1H-1,2,4-triazole,
  1-[2-(2,4-dichlorophenyl)-4-n-propyl-1,3-dioxolan-2-ylethyl]-1H-1,2,4-triazole,
  N-(n-propyl)-N-(2,4,6-trichlorophenoxyethyl)-N'-imidazolyl-urea,
  1-(4-chlorophenoxy)-3,3-dimethyl-1-(1H-1,2,4-triazol-1-yl)-butan-2-one,
  1-(4-chlorophenoxy)-3,3-dimethyl-1-(1H-1,2,4-triazol-1-yl)-butan-2-ol,
  α-(2-chlorophenyl)-α-(4-chlorophenyl)-5-pyrimidinemethanol,
  5-butyl-(2-dimethylamino-4-hydroxy-6-methylpyrimidine,
  bis-(p-chlorophenyl)-3-pyridinemethanol,
  1,2-bis-(3-ethoxycarbonyl-2-thioureido)-benzene,
  1,2-bis-(3-methoxycarbonyl-2-thioureido)-benzene,
and various fungicides, such as
  dodecylguanidine acetate,
  3-[3-(3,5-dimethyl-2-oxycyclohexyl)-2-hydroxyethyl]-glutaramide,
  hexachlorobenzene,
  DL-methyl-N-(2,6-dimethylphenyl)-N-fur-2-yl alanate,
  methyl DL-N-(2,6-dimethylphenyl)-N-(2'-methoxyacetyl)-alanate,
  N-(2,6-dimethylphenyl)-N-chloroacetyl-DL-2-aminobutyrlactone,
  methyl DL-N-(2,6-dimethylphenyl)-N-(phenylacetyl)-alanate,
  5-methyl-5-vinyl-3-(3,5-dichlorophenyl)-2,4-dioxo-1,3-oxazolidine,
  3-[3,5-dichlorophenyl]-5-methyl-5-methoxymethyl-1,3-oxazolidine-2,4-dione,
  3-(3,5-dichlorophenyl)-1-isopropylcarbamylhydantoin,
  N-(3,5-dichlorophenyl)-1,2-dimethylcyclopropane-1,2-dicarboximide,
  2-cyano-[N-(ethylaminocarbonyl)-2-methoximino]-acetamide,
  1-[2-(2,4-dichlorophenyl)-pentyl]-1H-1,2,4-triazole,
  2,4-difluoro-α-(1H-1,2,4-triazol-1-ylmethyl)-benzhydryl alcohol,
  N-(3-chloro-2,6-dinitro-4-trifluoromethylphenyl)-5-trifluoromethyl-3-chloro-2-aminopyridine, and 1-((bis-(4-fluorophenyl)-methylsilyl)-methyl)-1H-1,2,
4-triazole.

The novel compounds are also suitable for effectively combating pests such as insects, arachnids and nematodes. They may be used as pesticides in crop protection and in the hygiene, stores protection and veterinary sectors.

Examples of injurious insects belonging to the Lepidoptera order are *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholita funebrana, Grapholita molesta, Heliothis armigera, Heliothis virescens, Heliothis zea, Hellula undalis, Hibernia defoliaria, Hyphantria cunea, Hyponomeuta malinellus, Keifferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flamea, Pectinophora gossypiella, Peridroma saucia, Phalera bucephala, Phthorimaea operculella, Phyllocnistis citrella, Pieris brassicae, Plathypena scarbra, Plutella xylostella, Pseudoplusia includens, Phyacionia frustrana, Scrobipalpula absoluta, Sitotroga cerelella, Sparganothis pilleriana, Spodoptera frugiperda, Spodoptera littoralis, Spodoptera litura, Thaumatopoea pityocampa, Tortfix viridana, Trichoplusia ni* and *Zeiraphera canadensis.*

Examples from the Coleoptera order are *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrynchus napi, Chaetocnema tibialis, Conoderus vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Onlema oryzae, Ortiorrhynchus sulcatus, Ortiorrhynchus ovatus, Phaedon cochleariae, Phyllotreta chrysocephala*, Phyllophaga sp., *Phyllopertha horticola, Phyllotreta nemorum, Phyllotreta striolata, Popillia japonica, Sitona lineatus* and *Sitophilus granaria.*

Examples from the Diptera order are *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex piplens, Dacus cucurbitae, Dacus oleae, Dasineura brassicae, Fannia canicularis, Gasterophilus intestinalis, Glossia morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea* and *Tipula paludosa.*

Examples from the Thysanoptera order are *Frankliniella fusca, Frankliniella occidentalis, Frankliniella tritici, Scirtothrips citri, Thrips oryzae, Thrips palmi* and *Thrips tabaci.*

Examples from the Hymenoptera order are *Athalia rosae, Atta cephalotes, Atta sexdens, Atta texana, Hoplocampa minuta, Hoplocampa testudinea, Monomorium pharaonis, Solenopsis geminata* and *Solenopsis invicta.*

Examples from the Heteroptera order are *Acrosternum hilare, Blissus leucopterus, Cyrtopeltis notatus, Dysdercus cingulatus, Dysdercus intermedius, Eurygaster integriceps, Euchistus impictiventris, Leptoglossus phyllopus, Lygus lineolaris, Lygus pratensis, Nezara viridula, Piesma quadrata, Solubea insularis* and *Thyanta perditor.*

Examples from the Homoptera order are *Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dyasphis radicola, Dysaulacorthum pseudosolani, Empoasca fabae, Macrosiphum avenae, Macrosiphum euphorbiae, Macrosiphon rosae, Megoura viciae, Metopolophium dirhodum, Myzodes persicae, Myzus cerasi, Nilaparvata lugens, Pemphigus bursarius, Perkinsiella saccharicida, Phorodon humuli, Psylla mali, Psylla piri, Rhopalomyzus ascalonicus, Rhopalosiphum maidis, Sappaphis mala, Sappaphis mali, Schizaphis graminum, Schizoneura lanuginosa, Trialeurodes vaporariorum* and *Viteus vitifolii.*

Examples from the Isoptera order are *Calotermes flavicollis, Leucotermes flavipes, Reticulitermes lucifugus* and *Termes natalensis.*

Examples from the Orthoptera order are *Acheta domestica, Blatta orientalis, Blattella germanica, Forficula auricularia, Gryllotalpa gryllotalpa, Locusta migratoria, Melanoplus birittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus* and *Tachycines asynamorus.*

Examples from the Acarina order are *Amblyomma americanum, Amglyomma variegatum, Argas persicus, Boophilus annulatus, Boophilus decoloratus, Boophilus microplus, Brevipalpus phoenicis, Bryobia praetiosa, Dermacentor silvarum, Eotetranychus carpini, Eriophyes sheldoni, Hyalomma truncatum, Ixodes ricinus, Ixodes rubicundus, Ornithodorus moubata, Otobins megnini, Paratetranychus pilosus, Permanyssus gallinae, Phyllocaptrata oleivora, Polyphagotarsonemus latus, Psoroptes ovis, Rhipicephalus appendiculatus, Rhipicephalus evertsi, Saccoptes scabiei, Tetranychus cinnabarinus, Tetranychus kanzawai, Tetranychus pacificus, Tetranychus telarius* and *Tetranychus urticae.*

Examples from the nematodes class are root-knot nematodes, e.g., *Meloidogyne hapla, Meloidogyne incognita* and *Meloidogyne javanica*, cyst-forming nematodes, e.g., *Globodera rostochiensis, Heterodera avenae, Hetrodera glycinae, Heterodera schachtii* and *Heterodera trifolii*, and stem and leaf eelworms, e.g., *Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus* and *Pratylenchus goodeyi.*

The active ingredient concentrations in the ready-to-use formulations may vary considerably, but are generally from 0.0001 to 10, and preferably from 0.01 to 1%.

The active ingredients may also be successfully used in the ultra-low-volume (ULV) method, where it is possible to apply formulations containing more than 95 wt % of active ingredient, or even the active ingredient without any additives.

When the active ingredients are used for combating pests in the open, application rates are from 0.1 to 2.0, and preferably from 0.2 to 1.0, kg/ha.

Surprisingly, the novel compounds have not only a very good antimycotic in vitro action, but also a good therapeutically utilizable in vivo action, especially on dermatophytes, but also on Candida. They also have anti-bacterial effects. The active ingredients are thus a valuable enrichment of the pharmaceutical art.

The action on dermatophytes, bacteria and Protozoa can be demonstrated by methods described for instance in P. Klein, Bakteriologische Grundlagen der chemotherapeutischen Laboratoriumspraxis, Springer-Verlag, Berlin, 1957. The action on yeasts can be proved in the pseudomycelium or mycelium test with *Candida albicans* (cf. DE-OS 30 20 093).

In the model of guinea pig trichophytosis (*Trichophyton mentagrophytes*) (cf. Heffter-Heubner: Handbuch der exp. Pharmakologie, Vol. XVI/II A) the novel compounds have a good action and prevent relapse when applied externally.

The action of the compounds when applied topically in the model of experimental *Candida albicans* vaginitis was also good.

The compounds also have oral activity. In the experimental models of generalised candidiasis in mice and of *Candida albicans* vaginitis in rats the infections were satisfactorily cleared up with low oral doses of the test substances.

The compounds are therefore particularly suitable for external as well as oral treatment of fungal infections in humans and animals. Examples of indications for humans and animals are: dermatomycoses, especially caused by dermatophytes such as species of the genera Epidermophyton, Microsporum or Trichophyton, yeasts such as species of the genus Candida, and molds such as species of the genera Aspergillus, Mucor or Absidia.

The compounds can be used alone or together with known agents, especially antibiotics.

The chemotherapeutic agents or formulations are prepared with conventional solid, semisolid or liquid carriers or diluents and the auxiliaries conventionally used in pharmaceutical technology for the required mode of administration and with a dosage suitable for use in a conventional manner, in particular by mixing (cf. H. Sucker et al., Pharmazeutische Technologie, Thieme-Verlag, Stuttgart, 1978).

Examples of suitable administration forms are uncoated or coated tablets, capsules, pills, aqueous solutions, suspensions and emulsions, where appropriate sterile injectable solutions, non-aqueous emulsions, suspensions and solutions, ointments, creams, pastes, lotions etc.

The therapeutically active compound is present in pharmaceutical formulations preferably in a concentration of from 0.01 to 90% of the total weight of the mixture.

It is possible in general to administer the agent or agents orally both in human and in veterinary medicine in amounts of from about 1.0 to about 50.0, preferably 2 to 10, mg/kg of body weight per day, preferably in the form of several individual doses to achieve the required results. However, it may be necessary to deviate from the stated dosages, specifically as a function of the type and severity of the disease, the type of formulation and of administration of the drug, and the time or interval over which administration takes place. Thus, less than the abovementioned amount of agent may suffice in some cases, whereas more than the abovementioned amount of agent must be used in other cases.

Examples of pharmaceutical formulations:
Example A
Tablet containing 250 mg of agent
Composition for 1000 tablets:

| | |
|---|---|
| Agent | 250 g |
| Potato starch | 100 g |
| Lactose | 50 g |
| 4% gelatin solution | 45 g |
| Talc | 10 g |

Preparation:

The finely powdered agent, potato starch and lactose are mixed. The mixture is moistened with about 45 g of 4% gelatin solution, granulated to fine particles and dried. The dried granules are screened, mixed with 10 g of talc and compressed to tablets in a rotary tableting machine. The tablets are packed in polypropylene containers with a tightly fitting cap.

Example B
Cream containing 1% agent

| | |
|---|---|
| Agent | 1.0 g |
| Glycerol monostearate | 10.0 g |
| Cetyl alcohol | 4.0 g |
| Polyethylene glycol 400 stearate | 10.0 g |
| Polyethylene glycol sorbitan monostearate | 10.0 g |
| Propylene glycol | 6.0 g |
| Methyl p-hydroxybenzoate | 0.2 g |
| Demineralized water ad | 100.0 g |

Preparation:

The very finely powdered agent is suspended in propylene glycol, and the suspension is stirred into the melt of glycerol monostearate, cetyl alcohol, polyethylene glycol 400 stearate and polyethylene glycol sorbitan monostearate at 65° C. The solution of the methyl p-hydroxybenzoate in water at 70° C. is emulsified in this mixture. After cooling, the cream is homogenized in a colloid mill and packed into tubes.

Example C
Dusting powder containing 1% agent

| | |
|---|---|
| Agent | 1.0 g |
| Zinc oxide | 10.0 g |
| Magnesium oxide | 10.0 g |
| Highly disperse silica | 2.5 g |
| Magnesium stearate | 1.0 g |
| Talc | 75.5 g |

Preparation:

The agent is micronized in an airjet mill and homogeneously mixed with the other components. The mixture is forced through a screen (mesh size No. 7) and packed in polyethylene containers with a sprinkler top.

USE EXAMPLE 1

Effect of the compounds as inhibitors of mitochondrial respiration.

In order to determine the effect of the compounds according to the invention on mitochondrial respiration it is first necessary to isolate the mitochondria from the organisms being investigated. For this, in the case of the yeast *Saccharomyces cerevisiae*, the cells in a 30 to 40% strength suspension of the yeast in an aqueous solution of 0.6M mannitol+0.01M tris[hydroxymethyl]-aminomethane+ 0.002M disodium ethylenediaminetetraacetate (pH 6.8) are disrupted in a glass bead mill, and the extract is fractionated by differential centrifugation at 1000× g and 12000× g. The mitochondria are in the pellet from the 12000× g centrifugation.

It is also possible similarly to isolate mitochondria from other organisms, e.g. from the phytopathogenic fungus *Drechslera sorokiniana* (synonym: *Helminthosporium sativum*), from the dermatophyte *Trichophyton mentagrophytes*, which is a human pathogen, and, for example, from the house fly (*Musca domestica*) as insect or from the spider mite *Tetranychus urticae*.

The effect of the compounds on the respiratory chain is determined by adding a solution of the compound to be tested in dimethyl sulfoxide to a suspension of mitochondria in an aqueous solution of 0.01M tris-[hydroxymethyl]aminomethane+0.65M sorbitol+0.01M $KH_2PO_4$+0.01M KCl+ 0.0004M disodium ethylenediaminetetraacetate+0.3% bovine serum albumin+0.0007M KCN $6×10^{-6}$M ubiquinone 50+0.01M sodium succinate+0.15% cytochrome c (pH 7.5), and determining the rate of reduction of cytochrome c by photometry, measuring the increase in extinction at 546 nm. Used as control is a mixture with the equivalent amount of pure DMSO. The inhibition at the concentration of agent in each case is then calculated as follows $$\% \text{ inhibition} = 100 \cdot \frac{\left(\frac{\Delta E}{\Delta t}\right)_o - \left(\frac{\Delta E}{\Delta t}\right)_x}{\left(\frac{\Delta E}{\Delta t}\right)_o}$$

where $\Delta E$ is the change in extinction, at is the change in time, $$\left(\frac{\Delta E}{\Delta t}\right)_o$$

is the reaction rate for the control and $$\left(\frac{\Delta E}{\Delta t}\right)_x$$

is the reaction rate for the sample x.

The following table shows the effects of a number of compounds according to the invention as inhibitors of mitochondrial respiration in the yeast *Saccharomyces cerevisiae*, the phytopathogenic fungus *Drechslera sorokiniana* and the house fly *Musca domestica*. The inhibition was determined in each case at a test substance concentration of $1.8/10^{-5}$ mol/l. For comparison, the corresponding value for the morpholide of β-phenylcinnamic acid (A), which is disclosed in DE 33 06 996, has been indicated.

Table for Use Example 1
Inhibition of mitochondrial respiration by β-substituted cinnamic acid derivatives

| Compound No. | % inhibition of respiration at $1.8 \times 10^{-5}$ mol/l test substance | | |
|---|---|---|---|
| | Saccharomyces cerevisiae | Drechslera sorokiniana | Musca domestica |
| 1.1 | 23 | | |
| 1.71 | 30 | | 18 |
| 1.90 | 85 | | |
| 1.91 | 22 | | |
| 1.167 | 99 | | |
| 1a.2 | 88 | | 21 |
| 1a.37 | 98 | | |
| 1a.60 | 97 | 99 | 93 |
| 1a.61 | 98 | | 97 |
| 1a.62 | 87 | | 74 |
| 1a.63 | 93 | | 85 |
| 1a.64 | 94 | 98 | 93 |
| 1a.72 | 98 | 100 | 94 |
| 1a.74 | 99 | | |
| 1a.75 | 70 | | |
| 1a.77 | 63 | | |
| 1a.82 | 94 | | |
| 1a.83 | 78 | | |
| 1a.84 | 98 | | |
| 1a.86 | 97 | | |
| 1a.88 | 99 | | |
| 1a.89 | 99 | | |
| 1a.91 | 99 | | |
| 1a.98 | 100 | | |
| 1a.101 | 69 | | |
| 1a.108 | 98 | | |
| 1a.109 | 31 | | |
| 1a.110 | | | 12 |
| 1a.112 | 99 | | |
| 1a.113 | 80 | | |
| 1a.162 | 76 | | |
| 1a.181 | 99 | | |
| 1a.182 | 98 | | |
| 1a.233 | 88 | | 89 |
| 1a.238 | 99 | 74 | 87 |
| 1a.239 | 44 | | 16 |
| 1a.240 | 94 | | 84 |
| 1a.241 | 20 | | 9 |
| 1a.243 | 99 | 94 | 89 |
| 1a.244 | 65 | | 50 |
| 1a.245 | 98 | | 91 |
| 1a.246 | 84 | | 81 |
| 1a.247 | 99 | | |
| 1a.248 | 95 | | |
| 1a.250 | 99 | | |
| 1a.251 | 54 | | |
| 1a.264 | 98 | | |
| 1a.268 | 95 | 97 | 95 |
| 1a.269 | 96 | 81 | 76 |
| 1a.271 | 92 | | 94 |
| 1a.272 | 51 | | 78 |
| 1a.273 | 95 | 96 | 95 |
| 1a.288 | 50 | | 22 |
| 1a.290 | 98 | | 86 |
| 1a.292 | 87 | 79 | 61 |
| 1a.293 | 65 | | 27 |
| 1a.294 | 98 | | 95 |
| 1a.295 | 94 | | 76 |
| 1a.297 | 70 | | 22 |
| 1a.300 | 98 | | 93 |
| 1a.302 | 97 | | 96 |
| 1a.303 | 98 | | 86 |
| 1a.304 | 97 | | 96 |
| 1a.305 | 30 | | 39 |
| 1a.306 | 98 | | 96 |
| 1a.307 | 58 | | 71 |
| 1a.308 | 99 | | |
| 1a.310 | 99 | | |
| 1a.312 | 99 | | |
| 1a.314 | 99 | | |
| 1a.316 | 98 | | |
| 1a.317 | 29 | | |
| 1a.318 | 98 | | |
| 1a.319 | 11 | | |
| 1a.320 | 98 | | |
| 1a.321 | 19 | | |
| 1a.322 | 99 | | |

Table for Use Example 1
Inhibition of mitochondrial respiration by β-substituted
cinnamic acid derivatives

| Compound No. | % inhibition of respiration at $1.8 \times 10^{-5}$ mol/l test substance | | |
|---|---|---|---|
| | *Saccharomyces cerevisiae* | *Drechslera sorokiniana* | *Musca domestica* |
| 1a.323 | 99 | | |
| 1a.324 | 99 | | |
| 1a.329 | 9 | | |
| 1a.331 | 79 | | |
| 1a.333 | 20 | | |
| 1a.358 | 99 | | |
| 1a.394 | 96 | | 99 |
| 1a.519 | 97 | | 89 |
| Morpholide of β-phenyl-cinnamic acid (comparison compound A) | 2 | 0 | 5 |

USE EXAMPLE 2

Activity against *Plasmopara viticola*

Leaves of potted vines of the Müller Thurgau variety were sprayed with an aqueous liquor which contained 80% of active ingredient and 20% of emulsifier in dry matter. To assess the duration of action of the active ingredient, after the sprayed-on layer had dried the plants were placed in a greenhouse for 8 days. The leaves were then infected with a suspension of *Plasmopara viticola* zoospores. The vines were then placed first in a chamber saturated with water vapor at 24° C. for 48 hours and then in a greenhouse at from 20° to 30° C. for 5 days. After this, to speed up sporangiophore discharge, the plants were again placed in the humidity chamber for 16 hours. The extent of fungus attack was then assessed on the undersides of the leaves.

The result of the tests shows that novel compounds Nos. 1a.31, 1a.61, 1a.62, 1a.63, 1a.72, 1a.110, 1a.182, 1a.238, 1a.310, 1a.312, 1a.318, 1a.321, 1a.323, 1a.356 and 1a.394 have, when used as aqueous dispersion containing 250 ppm active ingredient, a better fungicidal effect (10% fungal attack) than the known active ingredient A (35% fungal attack).

USE EXAMPLE 3

Activity against wheat mildew

Leaves of pot-grown wheat seedlings of the Frühgold variety were sprayed with an aqueous liquor which contained 80% of active ingredient and 20% of emulsifier in dry matter and, 24 hours after the sprayed-on layer had dried, were dusted with spores of wheat mildew (*Erysiphe graminis* var. *tritici*). The test plants were then placed in a greenhouse at from 20° to 22° C. and from 75 to 80% relative humidity. The extent of mildew spread was assessed after 7 days.

The result of the tests shows that novel compounds Nos. 1a.2, 1a.60, 1a.61, 1a.63, 1a.72, 1a.239, 1a.245, 1a.246, 1a.248, 1a.290, 1a.292, 1a.294, 1a.304 and 1a.356 have, when used as aqueous dispersion containing 250 ppm active ingredient, a better fungicidal effect (15% fungal attack) than the known active ingredient A (45% fungal attack).

USE EXAMPLE 4

Activity against *Pyricularia oryzae* (protective)

Leaves of pot-grown rice seedlings of the Bahia variety were sprayed to runoff with aqueous emulsions which contained 80% of active ingredient and 20% of emulsifier in dry matter and, 24 hours later, inoculated with an aqueous suspension of *Pyricularia oryzae* spores. The test plants were then placed in chambers at from 22 to 24° C. and from 95 to 99% relative humidity. The extent of disease was assessed after 6 days.

The result of the tests shows that novel compounds Nos. 1a.72, 1a.181, 1a.248, 1a.302, 1a.314 and 1a.356 have, when used as aqueous dispersion containing 250 ppm active ingredient, a better fungicidal effect (15% fungal attack) than the known active ingredient A (60% fungal attack).

The compounds of the formula 1 where $R^1$, U, V, W, $X_m$, Y and Z have the abovementioned meanings can be prepared by the synthetic routes and processes described in the following section.

The compounds of the formula 3 where U, V, W, Y and Z have the abovementioned meanings are important intermediates in this connection, and the present invention relates to them. The possible ways of preparing these intermediates of the formula 3 are indicated in Scheme 1. Their use for the synthesis of final products of the formula 1 is explained thereafter (see, for example, Schemes 2 and 3).

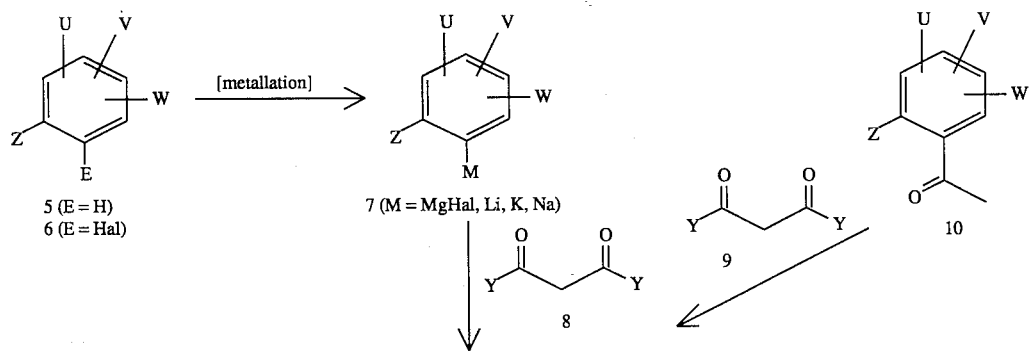

Scheme 1

-continued
Scheme 1

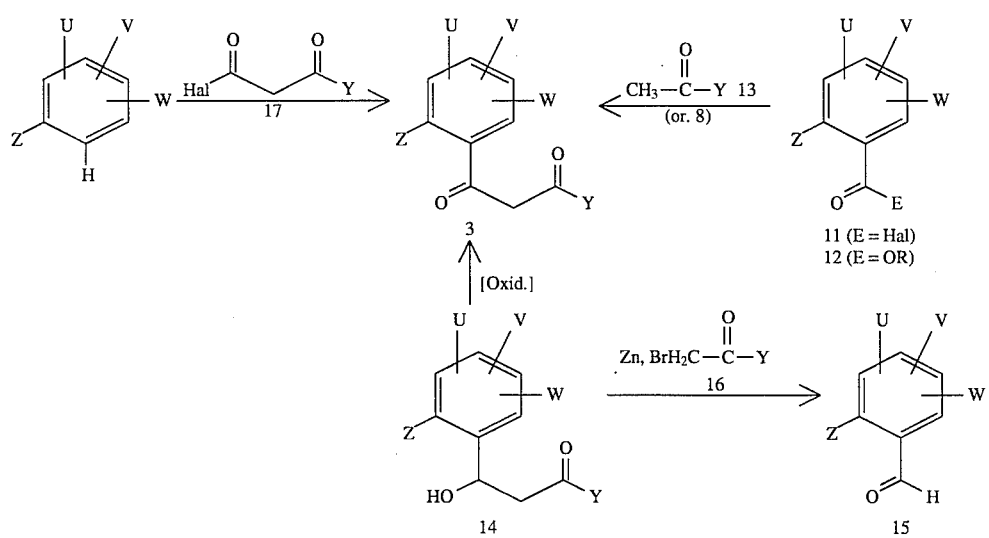

The intermediates of the formula 3 are obtained, for example, by reacting the appropriate organometallic compounds 7, which in turn can be obtained by metallation or metal/halogen exchange from the corresponding precursors 5 and 6 by conventional processes (cf. Advanced Org. Chem., 3rd. Ed., 545 et seq., 1985) with the malonic acid derivatives 8 in a conventional manner (cf., for example, Houben-Weyl, Vol. VII/2a, 595 et seq.).

The intermediates of the formula 3 can be prepared from the acetophenone derivatives 10 in a condensation with the carbonic acid derivatives 9 in the presence of a base such as sodium hydride in a conventional manner (cf., for example, Org. Synth. 47 (1967) 20).

The β-keto acid derivatives 3 are obtained from the benzoic acid derivatives 11 and 12 by reaction with an acetic acid derivative 13 in the presence of a base such as sodium hydride, sodium methanolate or potassium tert-butanolate in a conventional manner (cf., for example, Org. Synth. 23, (1943) 35).

Oxidation of the benzyl alcohols 14 in a conventional manner (cf. Organikum 16th Ed., page 358, 1986) likewise provides the intermediates 3. The benzyl alcohols 14 themselves can be prepared from the corresponding aldehydes 15 by processes known from the literature, eg. by a Reformatsky synthesis (cf., for example, J. Org. Chem., 35 (1970) 3966).

The intermediates 3 can also be prepared from the benzene derivatives of the formula 5 by Friedel-Crafts acylation, in the presence or absence of a catalyst such as $AlCl_3$, $FeCl_3$, $ZnCl_2$, in a conventional manner (cf., for example, Organikum 16th Ed., pp. 323 et seq., 1986).

The acetophenones 10, benzoic acid derivatives 11 and 12 and benzaldehydes 15 which can be employed as precursors are either known or preparable by a conventional method, e.g. from the metallated intermediates of the formula 7 by reaction of an electrophile, eg. with an acetic acid derivative (→10), a carbonic acid derivative (→12) or a formic acid derivative (→15).

The compounds of the formula 1 where $R^1$, U, V, W, Y and Z have the abovementioned meanings and where X is oxygen and m is 1 can be prepared, for example, as shown in Scheme 2.

Scheme 2

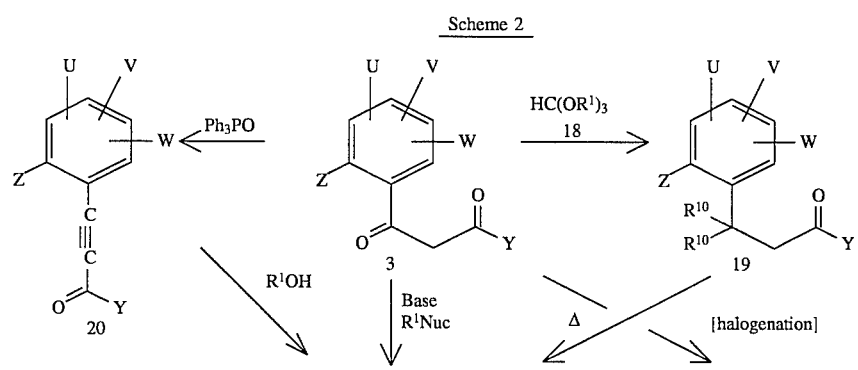

-continued
Scheme 2

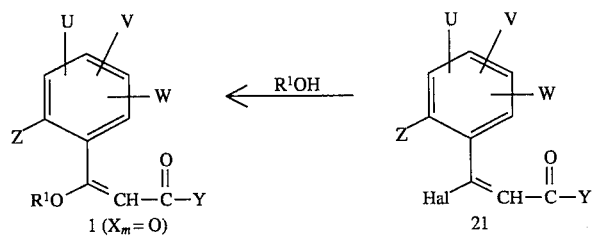

Reaction of the β-keto acid derivatives 3, in particular the β-keto esters, in a conventional manner with an alkylating agent $R^1Nuc$, e.g. with a dialkyl sulfate such as dimethyl sulfate or with an alkyl halide such as methyl chloride or butyl chloride, in a solvent or diluent such as dimethyl sulfoxide or hexamethylphosphoric triamide, in the presence or absence of a base such as sodium hydride or potassium tert-butylate, results in compounds of the formula 1 where $X_m$ is oxygen (cf., for example, Synthesis (1970) 1).

An alternative possibility is to react β-keto acid derivatives of the formula 3 in a conventional manner with an orthoformic ester 18, in the presence or absence of an acid such as hydrochloric acid, sulfuric acid or p-toluenesulfonic acid. The resulting ketals 19 can be either isolated and then converted into the products 1 by heating, or else converted directly without isolation into the products 1 (cf. Houben-Weyl, Vol. 6/3, page 112, 1965).

The novel compounds of the formula 1 can be prepared from the acetylene derivatives 20 by addition of an alcohol $R^1OH$ in the presence or absence of a catalyst such as HCl or KOH (cf., for example, Houben-Weyl, Vol. 6/3, page 114, 1965).

The acetylene derivatives 20 themselves can be obtained by conventional processes, for example, from the β-keto acid derivatives 3, eg. by reaction with triphenylphosphine oxide (cf., for example, Synthesis (1989) 217).

In addition, the novel compounds of the formula 1 can be prepared from the vinyl halides 21 by nucleophilic substitution with an alcohol $R^1OH$ in the presence or absence of a base such as sodium hydride (cf., for example, J. Org. Chem. 50 (1985) 4664).

The vinyl halides 21 themselves can be obtained, for example, by halogenation of the β-keto acid derivatives 3 in a conventional manner (cf., for example, Org. Synth. 6 (1926) 505).

Scheme 3 explains the synthesis of compounds of the formula 1 where $R^1$, U, V, W, Y and Z have the abovementioned meanings, and where $X_m$ is sulfur (corresponds to formula 22 in Scheme 3).

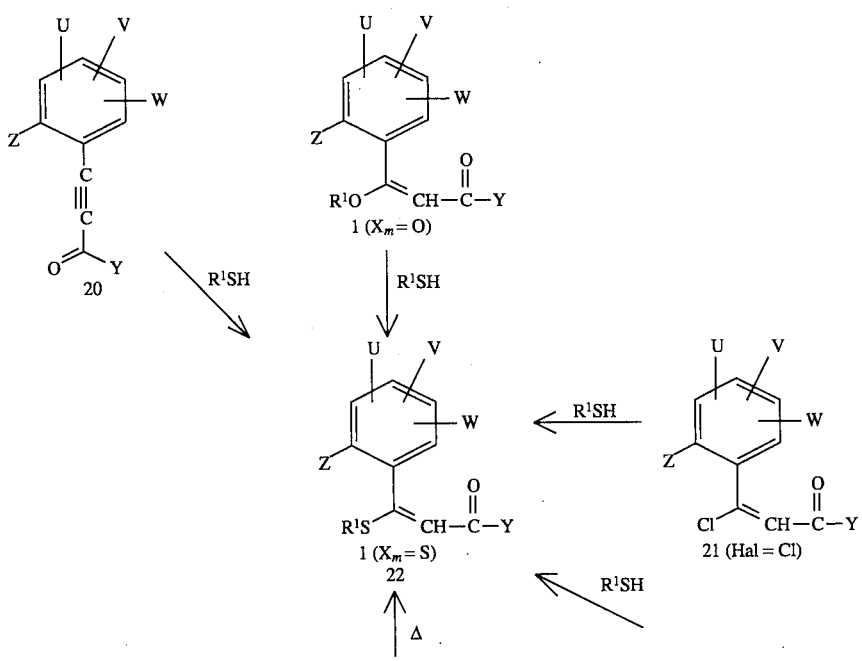

Scheme 3

-continued
Scheme 3

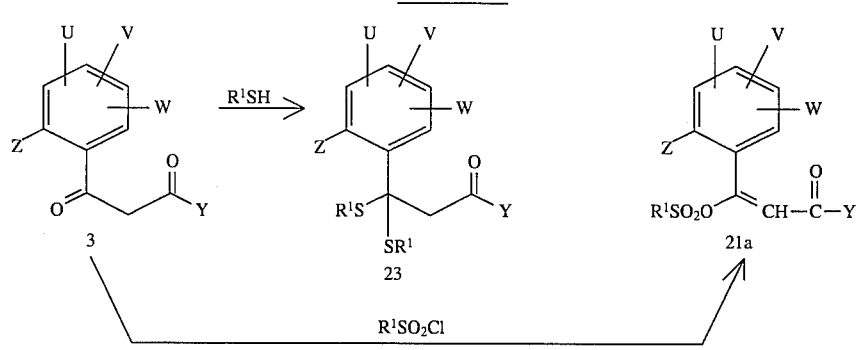

The novel compounds of the formula 22 can be prepared from the acetylene derivatives 20 by addition of a thiol $R^1SH$ in the presence or absence of a base such as KOH or pyridine, or of an acid such as HCl (cf., for example, E. Larsson, J. Prakt. Chem. 325 (1983) 328; Synthesis 12 (1986) 1070; Houben-Weyl Vol. 9., page 133 (1955).

Compounds of the formula 22 can also be prepared by reacting β-keto acid derivatives, especially β-keto esters 3, in a conventional manner in the presence or absence of an acid such as hydrochloric acid, sulfuric acid or p-toluenesulfonic acid, or of a Lewis acid such as $ZnCl_2$ or $BF_3$, with thiols $R^1SH$. The resulting thioketals 23 can be converted either directly or, after isolation, by heating into the products 22 (cf., for example, Angew. Chem. 77 (1965) 1140; J. Org. Chem. 40 (1975) 812).

Compounds of the formula 22 can be prepared from compounds of the formula 21 or 21a by reaction with thiols $R^1SH$ in the presence or absence of a base, in a conventional manner. Compounds of the formula 21a can be prepared by reacting compounds of the formula 3 with sulfonyl chlorides $R^1SO_2Cl$ such as methanesulfonyl chloride (R'=methyl) or toluenesulfonyl chloride (R'=p-methylphenyl), with or without the addition of bases (e.g. triethylamine or sodium hydride).

Compounds of the formula 22 can also be prepared by reacting compounds of the formula 1 where X is oxygen and m is 1 with thiols $R^1SH$ under acidic or alkaline conditions.

The enamines of the formulae 24 and 25 (corresponding to formula 1 with $X_m=NR^2$ and $NOR^3$ respectively) where $R^1$, $R^2$, $R^3$, U, V, W, Y and Z have the abovementioned meanings can be prepared, for example, as shown in Scheme 4.

Scheme 4

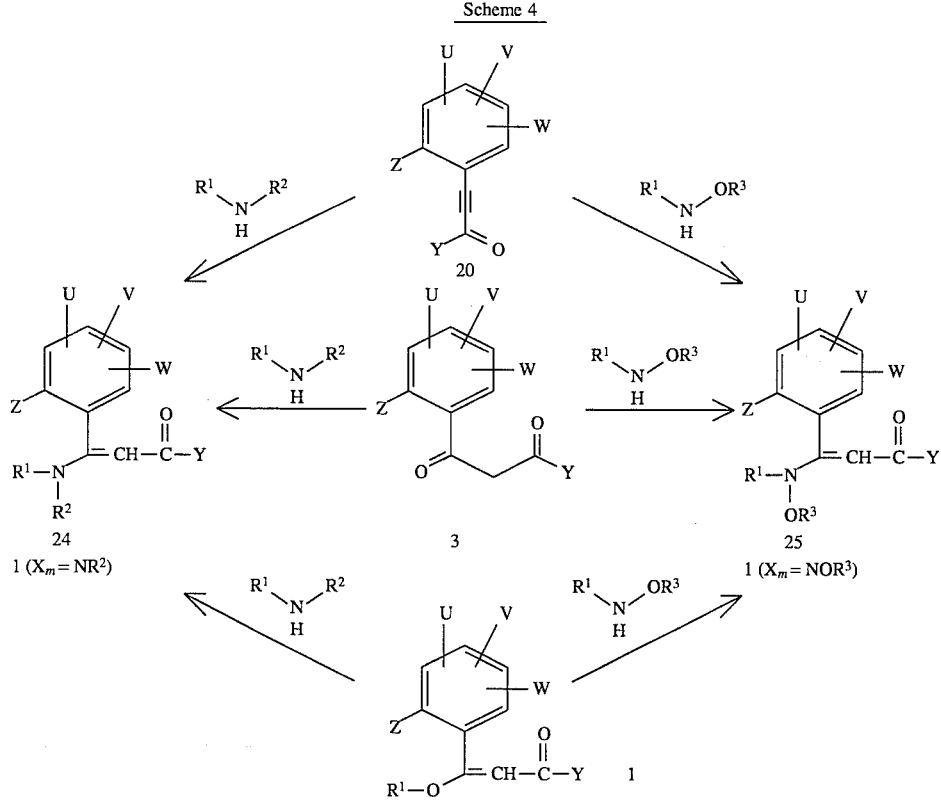

The novel compounds of the formula 24 can be prepared from compounds of the formula 20 in a conventional manner by addition of amines of the formula $R^1R^2NH$ (cf., for example, Houben-Weyl, Vol. 11/1, pages 299 et seq. 1957). The compounds of the formula 25 can be prepared similarly by addition of alkoxyamines $R^1R^3ONH$ onto compounds of the formula 20.

Enamines of the formula 24 can furthermore be prepared by reacting β-keto acid derivatives, especially β-keto esters 3 with primary or secondary amines $R^1R^2NH$, where appropriate under acidic or basic conditions in a conventional manner (cf., for example, Houben-Weyl, Vol. 11/1, page 172, 1957). For example β-keto esters 3 can firstly be converted with a base such as sodium hydride or sodium hydroxide into the enolates which react with the hydrochlorides of primary or secondary amines to give compounds of the formula 24 with liberation of sodium chloride (cf., for example, Ann. Chim. [10] 18 (1932) 103; J. Am. Chem. Soc. 70 (1948) 3350). Compounds of the formula 25 are prepared from β-keto acid derivatives 3 similarly by reaction with alkoxyamines $R^3ONHR^1$.

It is furthermore possible to prepare enamines 24 by reacting compounds of the formula 1 where X is oxygen and m is 1 with primary or secondary amines $R^1R^2NH$, where appropriate under acidic or basic conditions, in a conventional manner (cf., for example, Houben-Weyl, Vol. 11/1, page 198 (1957); J. Heterocycl. Chem. 21 (1984) 1753; Indian J. Chem. 27 (1988) 1044).

Scheme 5 illustrates the synthesis of compounds of the formula 1 where $R^1$ U, V, W, Y and Z have the abovementioned meanings, and m is 0 (corresponding to formula 26 in Scheme 5).

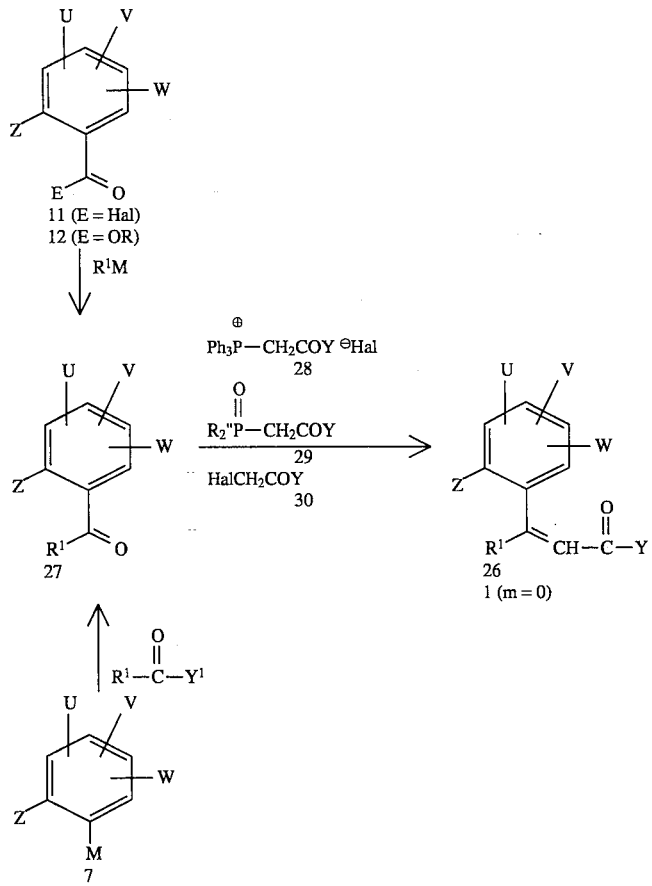

Scheme 5

The β-alkylcinnamic acid derivatives 26 are obtained from the aryl ketones 27 by, for example, reaction in a conventional manner (cf., for example, Tetrahedron 46 (1990) 5859) with a Wittig reagent or Wittig-Horner reagent of the formula 28 or 29 in an inert organic solvent in the presence of a base such as sodium hydride or potassium t-butylate. Hal in the formula 28 is a halogen atom such as chlorine or bromine. R" in the formula 29 is alkoxy such as methoxy or ethoxy.

An alternative possibility for the preparation of compounds of the formula 26 is to react 27 in a conventional manner (cf., for example, Bull. Soc. Chim. Belg. 79 (1970) 61–74) with e-haloacetic acid derivatives of the formula 30 and zinc in a Reformatsky reaction, followed by dehydration. Hal in formula 30 is chlorine or bromine.

The aryl ketones 27 are either known or obtainable by known methods, for example from compounds of the formula 7 by reaction with carboxylic acid derivatives $R^1COY'$ where Y' is halogen, OR or $NR_2$, or from compounds of the formula 11 or 12 by reaction with organometallic compounds $R^1M$.

Compounds of the formula 1, where COY represents the various suitable ester, thiol ester and amide groups can easily be prepared by a number of standard processes by conversion of COY (see, for example, Houben-Weyl, Methoden der Organischen Chemie, Volume E5 and preparation examples 9–11). Thus, for example, the esters of the formula 1 where Y is $OR^1$ can easily be converted into the corresponding carboxylic acids by hydrolysis by conventional processes (see, for example, Houben-Weyl, Volume E5, pages 223–254, specifically 231–237). The latter can subsequently be converted into activated derivatives such as the imidazolides with Y=1-imidazolyl or the chlorides with Y=Cl (see, for example, Houben-Weyl, Volume VIII, pages 463 et seq.). In turn, reaction of the latter with alcohols or oximes gives the corresponding esters of the formula 1 with $Y=OR^4$ or the oxime esters with $Y=O-N=CR^5R^6$ (see, for example, Houben-Weyl, Volume VIII, pages 543 et seq.), or with thiols gives the corresponding thiol esters of the formula 1 with $Y=SR^{11}$ (see, for example, Houben-Weyl, Volume IX, pages 753–755), or with amines gives the corresponding amides of the formula 1 with $Y=NR^7R^8$ or $Y=N(OR^9)R^{10}$ (see, for example, Houben-Weyl, Volume VIII, pages 655 et seq.).

The novel compounds of the formula 1b where V, W, $X_m$, Y and $R^1$ have the meanings stated in claim 1, and Z and U in adjacent positions on the phenyl ring together form an unsubstituted or substituted five- or six-membered aromatic or heteroaromatic ring, are prepared by the processes described above from the corresponding benzo-fused intermediates, eg. similar to the synthetic routes indicated in Schemes 1 to 5. The preparation of the fused intermediates is described hereinafter (cf. Schemes 6 to 8).

For example, suitable precursors are 1,7-di-substituted naphthalene derivatives of the formula 10a which are known or can be prepared in a conventional manner. For example, compounds of the formula 10a are obtained from 2-substituted naphthalenes by Friedel-Crafts acylation, in the presence or absence of a catalyst such as $AlCl_3$, $FeCl_3$, $ZnCl_2$, similar to known methods (cf., for example, J. Chem. Soc. C (1966) 518).

Scheme 6

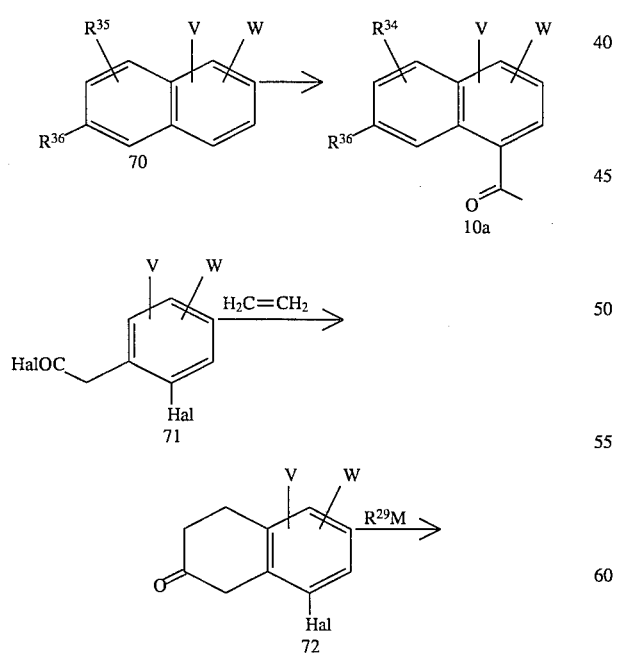

-continued
Scheme 6

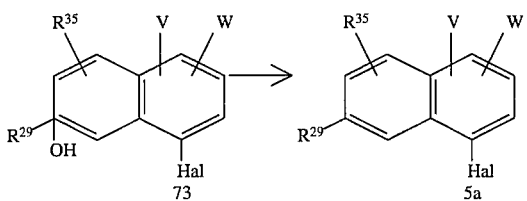

V, W, Hal, $R^{29}$, $R^{35}$ and $R^{36}$ as defined above.

Furthermore, compounds of the formula 6a where $R^{29}$ has the abovementioned meanings are obtained from (2-halophenyl)acetic acid derivatives, for example the corresponding chlorides, by reaction with ethylene in the presence of a Lewis acid, for example $AlCl_3$, to give the ketones 72. Reaction of the ketones with organometallic compounds $R^{29}M$, for example with organolithium compounds or Grignard compounds, provides the alcohols 73 which are aromatised with triphenylmethanol under acidic conditions to give the naphthalene derivatives 6a which are required as intermediates (cf., for example, EP 393 941). The latter can be converted by the routes explained in Scheme 1 into the final products of the formula 1 or 1b.

The 2-substituted 8-quinolinecarboxylic acid derivatives of the formula 12b required as intermediates can be obtained from aldehydes and o-toluidines, when $R^{36}=R^{29}$, as shown in the following Scheme 7:

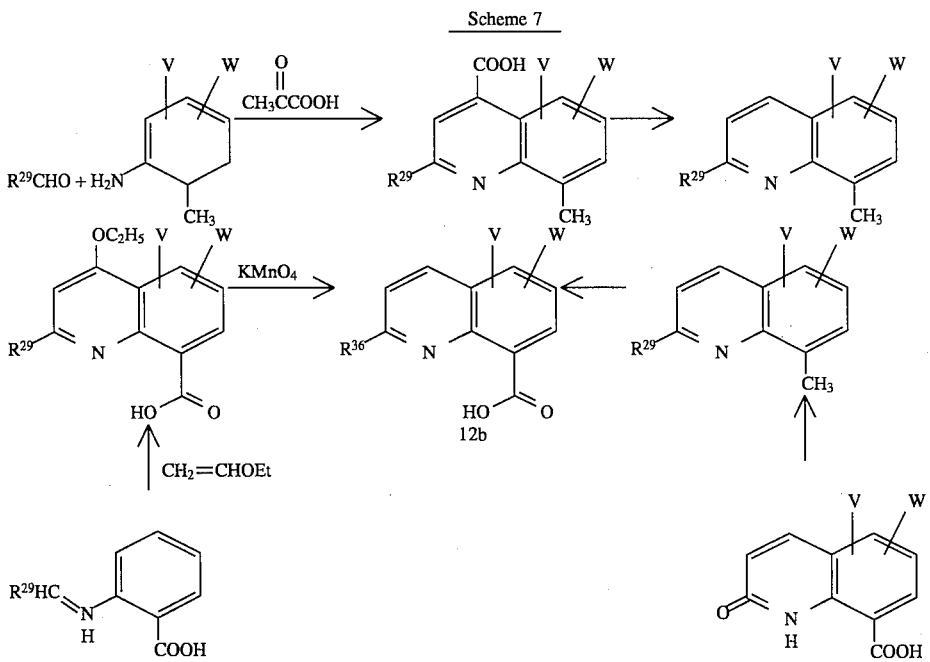

V, W, $R^{29}$ and $R^{36}$ as defined above

Aldehydes undergo a Doebner reaction with o-toluidines to give 2-substituted 8-methylquinoline-4-carboxylic acids which are converted by copper-catalyzed decarboxylation into the corresponding methylquinolines. Oxidation of the methyl group by conventional methods gives the required 8-quinolinecarboxylic acids 12b (cf., for example, J. Am. Chem. Soc. 68 (1946) 1589).

Furthermore, when $R^{36}=R^{29}$, 8-quinolinecarboxylic acids of the formula 12b are obtained from Schiff's bases of anthranilic acid derivatives by reaction with vinyl ethers in the presence of an acid catalyst, for example $H_2SO_4$ or $BF_3$, and subsequent oxidative aromatisation of the 4-alkoxy-1,2,3,4-tetrahydroquinoline-8-carboxylic acid, for example with $KMnO_4$ (cf., for example, Izv. AN SSSR, Ser. kim. (1966) 120 (Engl.)).

In the case where $R^{36}$ is $OR^{12}$, $SR^{13}$ or $NR^{37}R^{38}$, the compounds 12b can be obtained from the 2-haloquinolines by reaction with an alcohol ($R^{12}OH$), a mercaptan ($R^{13}SH$) or an amine ($R^{37}R^{38}NH$), in the presence or absence of a base. The 2-haloquinolines are obtained by conventional processes (cf., for example, Houben-Weyl, Vol. V/3, 920) from the 2-quinolones (cf., for example, Chem. Pharm. Bull. 34 (1986) 682).

The carboxylic acids of the formula 12b are then converted into the esters or halides, which are converted like the compounds of the formula 11 or 12 by the routes shown in Schemes 1 and 2 into the final products of the formula 1 or 1b.

5-Quinolinecarboxylic acid derivatives of the formula 12c are obtained from 3-aminobenzoic acids and β-alkoxyacryloyl halides as shown in Scheme 8:

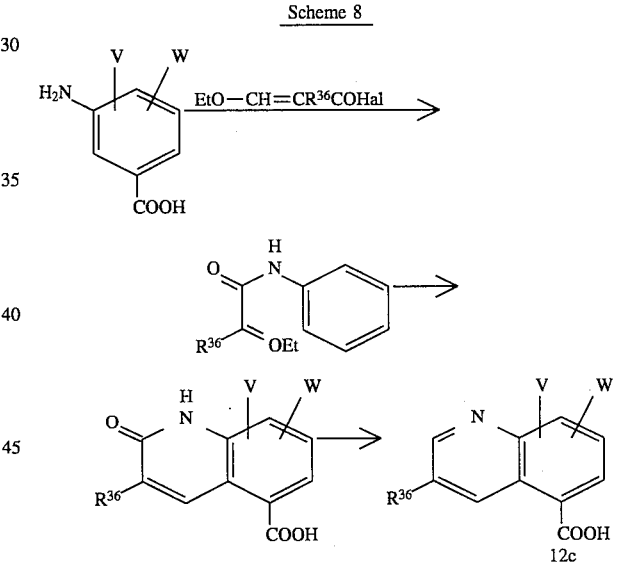

The 2-quinolones are converted into the quinolines by conventional methods (cf., for example, J. Heterocyclic Chem. 24 (1987) 351).

Further quinoline intermediates can be prepared by processes similar to those described in Chem. Heterocyclic Comp. Vol. 32, Chap. 2.

Quinazolines can be obtained from o-aminobenzaldehydes by Bischler condensation with ammonia (cf., for example, J. Chem. Soc. (1965) 5360).

Cinnolines can be obtained from 2-aminoacetophenones by diazotization and cyclization to 4-hydroxycinnolines in a Borsche synthesis (cf., for example, Liebigs Ann. Chem. 546 (1941) 293) and subsequent reduction (cf., for example, J. Chem. Soc. (1959) 2858).

Quinoxalines can be obtained from o-phenylenediamines by reaction with α-bromo ketones and oxidation to the aromatic system (cf., for example, J. Chem. Eng. Data 18 (1973) 102).

1,2,4-Benzotriazines are prepared from o-nitrophenylhydrazides of carboxylic acids by known processes (cf., for example, Chem. Bet. 22 (1889) 2801).

3,5-disubstituted isoquinolines are known or can be prepared by known processes (cf., for example, J. Org. Chem. 23 (1958) 435).

2,4- and 2,7-disubstituted benzoxazoles are obtained by conventional processes from o-aminophenols by reaction with a carboxylic acid derivative, eg. a carbonyl chloride (cf., for example, J. Med. Chem. 20 (1977) 169). The o-aminophenols which can be employed as precursors are known or can be prepared by known methods (cf., for example, Biochem. Prep. 6 (1958) 20).

2,4-disubstituted indole derivatives can be prepared from 2-haloanilines, for example 2-bromoanilines, and enamines in the presence of a transition metal catalyst such as a Pd compound (cf., for example, J. Heterocycl. Chem. 24 (1987) 1555).

2,4-disubstituted benzofuran derivatives are obtained by conventional processes from 2-vinylfurans and acetylene derivatives, for example methyl propiolate, by cycloaddition and subsequent oxidation (cf., for example, Aust. J. Chem. 26 (1973) 1059).

2,4- and 2,7-disubstituted benzimidazoles are known or can be prepared in a conventional manner from o-phenylenediamines and carboxylic acids or derivatives thereof in the presence of a condensing agent, for example phosphonium anhydride (cf., for example, J. Org. Chem. 54 (1989) 1144). 2,4-disubstituted benzothiazoles are known or can be prepared by known processes from 2-halothioanilides (cf., for example, Synthesis (1976) 730).

The synthesis of the various side chains Z is explained in detail in Schemes 9 to 21 which follow.

For example, compounds of the formula 33 can be prepared by the routes indicated in Scheme 9.

Scheme 9

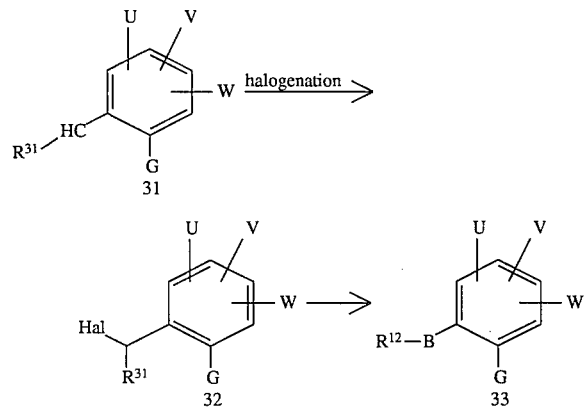

-continued
Scheme 9

Hal: Cl, Br, I

B: $-O-CHR^{31}-$, $-S-CHR^{31}-$, $-\overset{O}{\overset{\|}{C}}-O-CHR^{31}-$, $-R^{30}C=N-O-CHR^{31}-$, $-R^{17}N-CHR^{31}-$ G: $R^1-X_m\overset{O}{\overset{\|}{\underset{CH-C-Y}{\diagup\diagdown}}}$, $-COOR^4$, $-COR^1$, $-CHO$, Hal, H $R^1$, $R^4$, $R^{12}$, $R^{17}$, $R^{30}$, $R^{31}$, U, V, W, X, Y, m as defined above.

The benzyl halides of the formula 32 where $R^{31}$ is preferably hydrogen can be prepared by conventional methods by reacting the compounds 31 where $R^{31}$ is likewise preferably hydrogen with a halogenating agent such as chlorine, bromine, iodine, N-bromosuccinimide or N-chlorosuccinimide in an inert solvent such as tetrachloromethane, methylene chloride or cyclohexane, with our without exposure to a light source (e.g. Hg vapor lamp, 300 W) or addition of free radical initiators such as dibenzoyl peroxide or azoisobutyronitrile [see Angew. Chem. 71 (1959) 349].

Compounds 32 with Hal=iodide can also be prepared by methods known from the literature from the chlorides or bromides by reaction with, for example, sodium iodide in acetone [see J. Chem. Soc., Perkin Trans. I (1976) 416].

The benzyl halides 32 where $R^{31}$ is preferably hydrogen can be reacted by standard processes with nucleophiles, preferably N, O or S nucleophiles such as carboxylic acids, phenols, alcohols, mercaptans, amines and oximes, to give the compounds 33 according to the invention where $R^{31}$ is again preferably hydrogen, for example by reacting the compounds of the formula 32 with the abovementioned nucleophiles themselves or with the alkali metal, alkaline earth metal, silver or ammonium salts derived therefrom in a solvent such as acetone, acetonitrile, toluene, DMF or THF, with or without the addition of a catalyst, eg. 0.01 to 10% by weight potassium iodide [see Organikum, 17th Ed., pages 172 et seq., VEB Berlin (1988); Org. Synth. Coll. Vol. 5, pages 1031 et seq., J. Wiley & Sons (1973)].

The compounds of the formulae 35, 38, 39 and 40 can be prepared as described in Scheme 10, for example.

Scheme 10

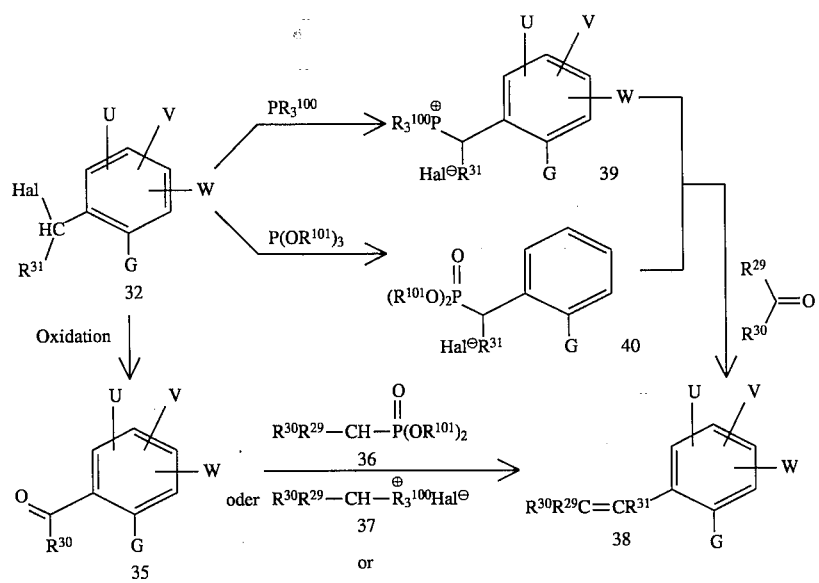

Hal=Cl, Br, I
$R^{100}$=Phenyl
$R^{101}$=$C_1$-$C_8$-alkyl
G, $R^{29}$, $R^{30}$, $R^{31}$, U, V and W as defined above.

The benzyl halides of the formula 32 where $R^{31}$ is preferably hydrogen can be reacted with oxidizing agents such as N-methylmorpholine N-oxide monohydrate or dimethyl sulfoxide in a conventional manner to give the oxo compounds 35 where $R^{31}$ is again preferably hydrogen [see J. Org. Chem. 24 (1959) 1792].

To prepare the olefins 38, the oxo compounds 35 can be reacted, for example, with a phosphonic ester of the formula 36 or a phosphonium salt of the formula 37. The reaction is carried out in a conventional manner [see J. Am. Chem. Soc. 83 (1961) 1733; Angew. Chem. 71 (1959) 260].

The starting materials are normally employed in the stoichiometric ratio. An excess of up to 10% (by weight) of one of the reactants above the stoichiometric amount is possible. The reaction is carried out in an inert solvent or diluent (eg. hexane, toluene, methylene chloride, dimethyl sulfoxide, particularly preferably tetrahydrofuran, dimethylformamide or diethyl ether; it is also possible to use mixtures of the said solvents) in the presence of an equivalent amount of a base (e.g. sodium hydride, sodium amide, potassium tert-butylate, sodium methylate, butyllithium, lithium diisopropylamide, potassium hydroxide).

The reactions normally take place in the range from $-70°$ C. to $+80°$ C., preferably $-70°$ C. to $+60°$ C.

The invention relates to both the E and Z isomers, but especially to the E isomers.

The phosphonates 36 and phosphonium salts 37 can easily be obtained from the halides $R^{30}R^{29}$—CH—Hal (Hal=Cl, Br, I) [see Houben-Weyl, 4th Ed., Vol. XII/1, pages 79 et seq. and 433 et seq. (1963)].

As an alternative, the olefins 38 can also be obtained by reaction of the carbonyl compounds 41 with the phosphonium salts 39 or the phosphonic esters 40 [see J. Am. Chem. Soc. 83 (1961) 1733; Angew. Chem. 71 (1959) 260].

The phosphonium salts 39 and phosphonic esters 40 are obtained, for example, by reacting the halides 32 with a phosphine of the formula $P(R^{100})_3$ or a phosphite of the formula $P(OR^{101})_3$. The reaction is carried out in a conventional manner [see Houben-Weyl, 4th Ed. Vol. XII/1, pages 79 et seq. and 433 et seq. (1963)].

The phosphonates of the formula 40 with $R^{31}\ne$hydrogen can also be prepared, for example, by reacting the phosphonates 40 where $R^{31}$=H with alkyl halides $R^{31}$-Hal (Hal=Cl, Br, I) using a base [see J. Am. Chem. Soc. 83 (1961) 1733].

The hydrogenation of the styrene derivatives 38 with diamine or else with $H_2$ in the presence of suitable hydrogenation catalysts such as Pd or Pt in suitable organic solvents such as tetrahydrofuran, methanol or acetic acid in a conventional manner gives the alkylated aromatic compounds 42 [see Organikum, 17th Ed. pages 288 et seq., VEB Berlin (1988)] (Scheme 11).

The compounds of the formulae 43 to 47 can be prepared, for example, as described in Scheme 12.

Scheme 11

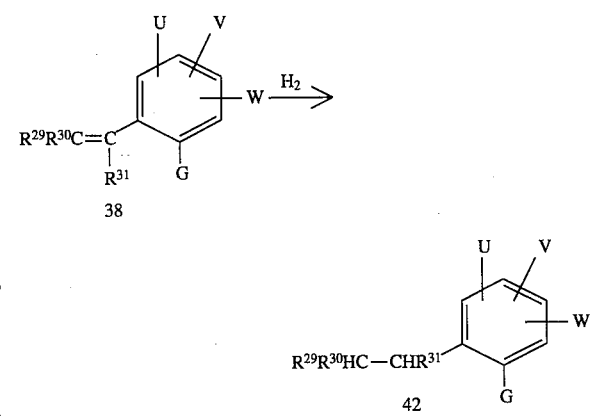

G, $R^{29}$, $R^{30}$, $R^{31}$, U, V, W as defined above

Scheme 12

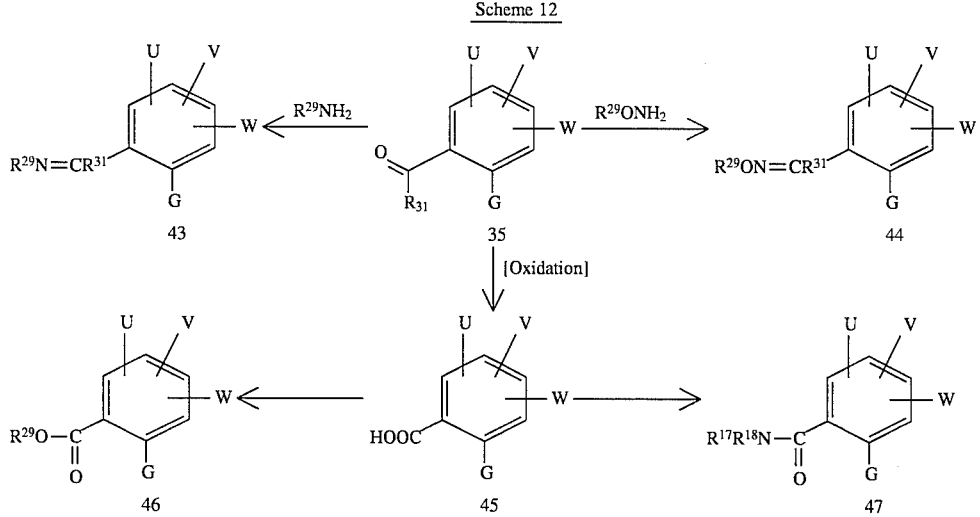

G, $R^{17}$, $R^{18}$, $R^{29}$, $R^{31}$, U, V, W as defined above

The reaction of the oxo compounds 35 with primary amines $R^{29}$—$NH_2$ to give the Schiff's bases 43 and with O-substituted hydroxylamines $R^{29}O$—$NH_2$ to give the oxime ethers 44 can be carried out in a conventional manner in an inert solvent or diluent such as methanol, ethanol, toluene or in a two-phase system such as toluene/water. It is possible to carry out the reaction with the addition of a suitable base such as triethylamine, sodium carbonate, potassium carbonate, potassium hydroxide or pyridine [see Houben-Weyl, 4th Ed., Vol. XI/2, pages 73 et seq. (1958); Houben-Weyl, 4th Ed., Vol. X/4, pages 55 et seq. (1968)]. The invention relates to both the E and Z isomers, especially to the E isomers.

The benzoic acids 45 can be prepared, for example, by oxidation of the aldehydes 35 ($R^{31}$=H) by known processes [see J. March, Advanced Organic Chemistry, 3rd Ed., pages 629 et seq., Wiley-Interscience Publication (1985)].

Standard methods of organic chemistry can be used to obtain further carboxylic acid derivatives therefrom, such as the esters 46 and amides 47 [see Organikum, 17th Ed., pages 400 et seq., VEB Berlin (1988)].

Schemes 13 to 15 illustrate the synthesis of compounds of the formula 1 where the side chain Z is OH, SH or $NH_2$ (cf. formulae 49, 50 and 51). These compounds are of particular interest as intermediates for synthesizing other compounds of formula 1 (eg. as shown in Scheme 17) and the present invention therefore also relates to them.

Scheme 13

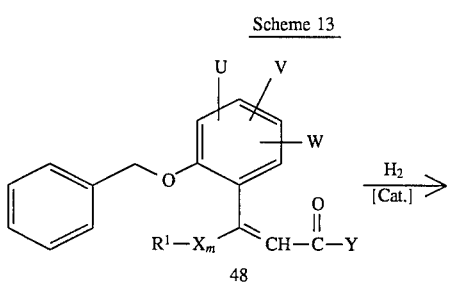

-continued
Scheme 13

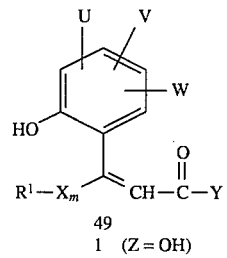

1 (Z = OH)

$R^1$, U, V, W, $X_m$, Y as defined above.

The ortho-substituted phenols 49 can be obtained as described in Scheme 13 in a conventional manner from the benzyl ethers 48 by catalytic hydrogenation (cf., for example, Prot. Groups in Org. Synth., page 19, 1981). The benzyl ethers 48 in turn can be prepared, for example, in the way described in Scheme 1 from the corresponding acetophenone derivatives 10 (with Z=—O—$CH_2$Ph).

The thiophenols 50 can be prepared from the phenols 49, for example, by reaction with dimethylthiocarbamoyl chloride by known methods (cf. Chem. Ber. 106 (1973) 2419) (Scheme 14).

Scheme 14

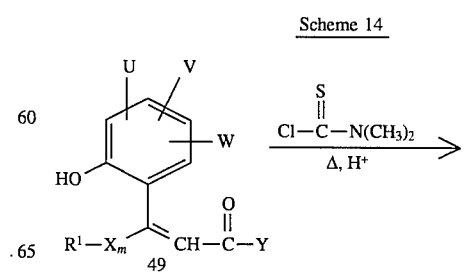

-continued
Scheme 14

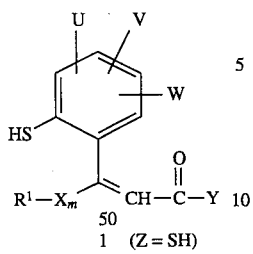

$R^1$, U, V, W, $X_m$, Y as defined above.

The anilines 51 can be prepared, for example, by catalytic reduction from the corresponding nitroaromatic compounds 52 (cf., for example, Organikum, 16th Ed., pages 534 et seq., 1986) (Scheme 15).

Scheme 15

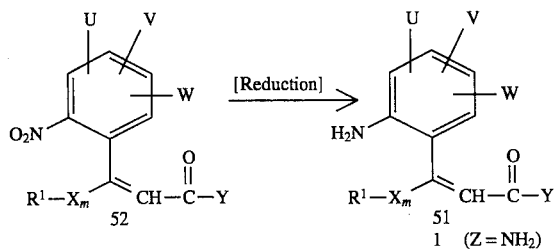

$R^1$, U, V, W, $X_m$, Y as defined above.

The novel compounds of the formula 54 where Z is $OR^{12}$, $SR^{13}$ or $NR^{37}R^{38}$ or can be prepared as shown in Scheme 16:

Scheme 16

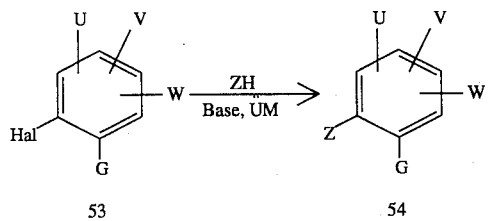

Hal: Bromine, chlorine
Z: $OR^{12}$, $SR^{13}$, $NR^{37}R^{38}$
G:

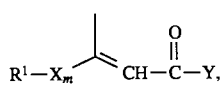

$CO_2R^4$, $COR^1$, CHO, H, Hal
$R^1, R^4, R^{12}, R^{13}, R^{37}, R^{38}$, X, Y, U, V, W and m as defined above.

The ortho-halo compounds 53 where Hal is preferably bromine can be reacted in the presence of a base such as $K_2CO_3$, NaH or potassium t-butylate, in the presence or absence of a transition metal catalyst (TM) such as copper powder or copper(I) chloride, with an alcohol ($R^{12}$OH), a mercaptan ($R^{13}$SH) or an amine ($R^{37}R^{38}$NH), in the presence or absence of a solvent or diluent such as acetone or DMF, in a conventional manner, eg. in an Ullmann reaction (cf., for example, Russ. Chem. Rev. 43 (1974) 679; J. Org. Chem. 29 (1964) 977) to give the novel compounds of the formula 54 where Z is $OR^{12}$, $SR^{13}$ or $NR^{37}R^{38}$.

As an alternative, compounds of the formula 54 can also be synthesized as shown in Scheme 17:

Scheme 17

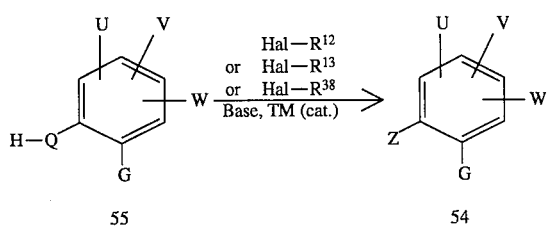

Q: O, S, $NR^{37}$
Hal: F, Cl, Br, I
G, Z, $R^{12}$, $R^{13}$, $R^{37}$, $R^{38}$, U, V, W as defined in Scheme 16.

The novel compounds of the formula 54 can be prepared by subjecting the compounds of the formula 55 to, for example, an Ullmann reaction (cf., for example, Russ. Chem. Rev. 43 (1974) 679; J. Org. Chem. 29 (1964) 977) or to a nucleophilic substitution reaction (cf., for example, J. Chem. Soc. (1942) 381; J. Heterocycl. Chem. 15 (1978) 1513) in the presence of a base, in the presence or absence of a transition metal catalyst [TM (cat.)] with a halogen compound, $R^{12}$-Hal, $R^{13}$-Hal or $R^{38}$-Hal, preferably a corresponding bromine compound, in the presence or absence of a solvent or diluent such as acetone or DMF, in a conventional manner.

The novel compounds of the formula 1 where Z is an acetylenic side chain $R^{29}$—C≡C— (see formula 56) can be prepared as shown in Scheme 18, for example.

Scheme 18

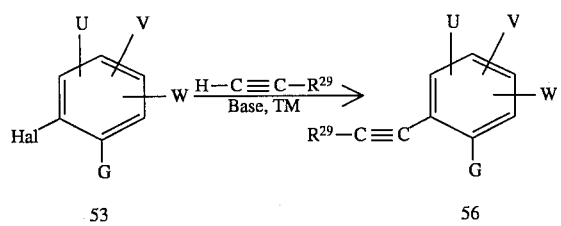

Hal: F, Cl, Br, I
G, U, V, W, $R^{29}$ as defined in Scheme 16.

The ortho-halo compounds 53, preferably the ortho-bromo compounds 53 (Hal=Br), can be subjected in a conventional manner to a Beck reaction (cf., for example, J. Organomet. Chem. 93. (1975) 259) with the terminal acetylenes H—C≡C—$R^{29}$, in the presence or absence of a base such as $K_2CO_3$, NaH, $NHEt_2$ or $NEt_3$, in the presence or absence of a solvent or diluent such as DMF, acetonitrile, THF or toluene, in the presence of a transition metal catalyst TM, for example a palladium or nickel compound such as $Pd(OAc)_2$, $NiCl_2$, $PdCl_2$ or $Pd(PPh_3)_4$, to give the acetylenes 56.

Novel compounds of the formula 1 where Z is a hetaryl group (see formula 58), can be prepared as shown in Scheme 19, for example.

Scheme 19

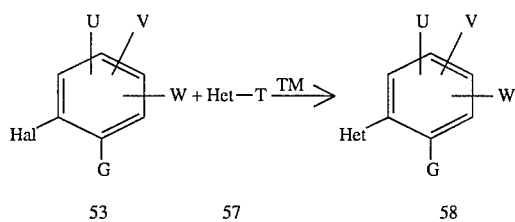

Hal: F, Cl, Br, I

T: Sn(C$_1$–C$_4$-alkyl)$_3$, B(O—H)$_2$

Het: Hetaryl as defined above

G, U, V, W: as defined in Scheme 16.

The ortho-halo compounds, preferably the orthobromo compounds 53 (Hal=Br), can be reacted in a conventional manner with the hetarylstannanes 57 (T=Sn(C$_1$–C$_4$-alkyl)$_3$) or with the hetaryl-boron compounds 57 (T=B(O—H)$_2$) in the presence of a transition metal catalyst TM, such as PdCl$_2$, Pd(OAc)$_2$, NiCl$_2$ or Pd(PPh$_3$)$_4$, to give the novel compounds of the formula 58 (cf., for example, Tetrahedron Lett. 27 (1986) 4407; Synth. Commun. 19 (1989) 101).

Furthermore, compounds of the formula 1 where Z is a five-membered heteroaromatic group can in many cases be synthesized by employing acetylenes of the formula 56 as dipolarophiles in 1,3-dipolar cycloadditions [cf., for example, R. Huisgen, Angew. Chem. Intern. Ed., 2 (1963) 565, 633].

Compounds of the formula 1 where Z is a substituted imino group (corresponding to formula 59) can be prepared as shown in Scheme 20.

Scheme 20

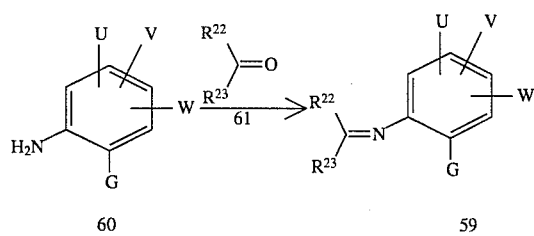

R$^{22}$, R$^{23}$, as defined above

G, U, V, W as defined in Scheme 16.

The imines of the formula 59 can be prepared in a conventional manner [cf., for example, Houben-Weyl, Vol. 7/1, 453; Houben-Weyl, Vol. 11/2, 74] from the aniline derivatives 60, by reacting the latter with the carbonyl compounds 61, in the presence or absence of an acid (e.g. HCl, H$_2$SO$_4$) or of a base (e.g. K$_2$CO$_3$, NEt$_3$), preferably with simultaneous removal of the water produced in the reaction using molecular sieves or by azeotropic distillation.

Novel compounds of the formulae 63 and 64 can be prepared as shown in Scheme 21.

Scheme 21

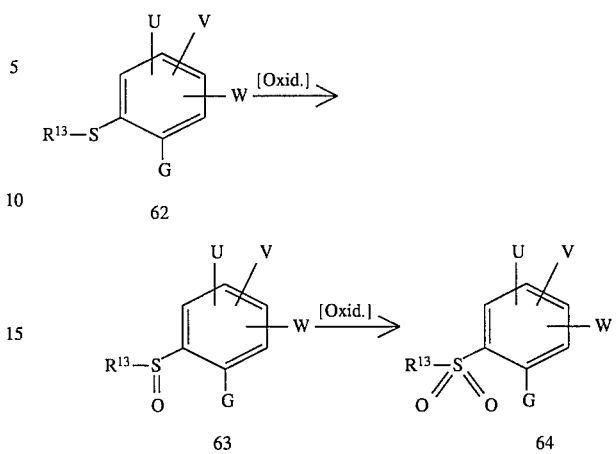

R$^{13}$, G, U, V, W as defined in Scheme 16.

The thio compounds 62 can be converted in a conventional manner (cf., for example, Houben-Weyl, Vol. 9, 219 et seq.) by an oxidizing agent such as oxygen, hydrogen peroxide or m-chloroperbenzoic acid, in the presence or absence of a solvent or a diluent such as toluene, into the sulfoxides 63 or the sulfones 64, which in this way are obtained selectively or as a mixture from which the individual components can be isolated by known processes, such as distillation or chromatography.

The preparation of the compounds according to the invention is illustrated by the following preparation examples:

EXAMPLE 1

Preparation of methyl (E)-β-methoxy-2-methylcinnamate (Compound No. 1.1 in Table 1).

a) A solution of 200 g (1.5 mol) of 2-methylacetophenone in 500 ml of tetrahydrofuran is slowly added dropwise at 60° C. under a nitrogen atmosphere to a suspension of 48 g (2.0 mol) of NaH and 180 g (2.0 mol) of dimethyl carbonate in 1.5 l of tetrahydrofuran. The mixture is stirred at 60° C. for 2 h.

After cooling, 100 ml of methanol are added, and the mixture is poured into ice-water and acidified with 10% strength hydrochloric acid. After extraction with methyl tert-butyl ether, the combined organic phases are washed with NaHCO$_3$ solution and water, dried over Na$_2$SO$_4$ and concentrated. The residue comprises 271 g (94%) of methyl 2-methylbenzoyl acetate as reddish brown oil.

$^1$H—NMR (CDCl$_3$): Keto form: δ=2.56 (s, 3H); 3.73 (s, 3H); 3.97 (s, 2H); 7.13–7.63 (m, 4H); ppm.

Also evident to a minor extent (about 30%) are the signals of the relevant enol form:

2.45 (s, 3H); 3.77 (s, 3H); 5.28 (s, 1H); 7.13–7.63 (m, 4H); 12.45 (s, 1H) ppm.

b) A mixture of 1280 g (6.7 mol ) of methyl 2-methylbenzoyl acetate, 848 g (8.0 mol) of trimethyl orthoformate, 400 ml of methanol and 10 ml of concentrated H$_2$SO$_4$ is stirred at room temperature for 12 h. The mixture is subsequently neutralized with 20 ml of pyridine and then concentrated, and the residue is fractionally distilled (boiling point 120–123° C./0.6 torr). 1300 g (94%) of methyl (E)-β-methoxy-2-methylcinnamate are obtained as a pale yellow oil.

$^1$H—NMR (CDCl$_3$): δ=2.23 (s, 3H); 3.52 (s, 3H); 3.76 (s, 3H); 5.34 (s, 1H); 7.13–7.31 (m, 4H) ppm

EXAMPLE 2

Preparation of methyl (E)-β-methoxy-2-bromomethylcinnamate (Compound No. 1.4 in Table 1).

200 g (0.97 mol) of methyl (E)-β-methoxy-2-methylcinnamate and 190 g (1.07 mol) of N-bromosuccinimide which has been washed with methanol and dried, in 2 l of dry tetrachloromethane, are irradiated with a 300 watt UV lamp for 75 min, during which the solution begins to reflux.

The precipitated succinimide is filtered off with suction, and the organic phase is washed with $NaHCO_3$ solution and water. After drying over $Na_2SO_4$, the solvent is removed by distillation, and the residue is crystallized from methyl tert-butyl ether/n-hexane. This results in 152 g (55%) of methyl (E)-2-methoxy-β-bromomethylcinnamate as colorless crystals of melting point 55°–57° C.

$^1$H—NMR ($CDCl_3$): δ=3.54 (s, 3H); 3.82 (s, 3H); 4.44 (s, 2H); 5.41 (s, 1H); 7.16–7.47 (m, 4H) ppm.

EXAMPLE 3

Preparation of Methyl (E)-2-formyl-β-methoxycinnamate (Compound No. 1.5 in Table 1).

100 g (0.35 mol) of methyl (E)-β-methoxy-2-bromomethylcinnamate (see Example 2) and 142 g (1.05 mol) of N-methylmorpholine N-oxide monohydrate in 300 ml of dimethyl sulfoxide are stirred at 5° C. for 1 h.

400 ml of saturated $NH_4Cl$ solution are added and the mixture is extracted with ethyl acetate. The combined organic phases are washed with water, dried over $Na_2SO_4$ and concentrated. The residue is taken up in methyl tert-butyl ether/n-hexane (2:1), filtered through silica gel and concentrated.

Treatment of the residue with methyl tert-butyl ether/n-hexane results in 52 g (68%) of methyl (E)-2-formyl-β-methoxycinnamate as colorless crystals with melting point 56°–58° C.

$^1$H—NMR ($CDCl_3$): δ=3.52 (s, 3H); 3.86 (s, 3H); 5.49 (s, 1H); 7.33–7.97 (m, 4H); 10.03 (s, 1) ppm.

EXAMPLE 4

Preparation of methyl (E)- and (Z)-2-{2-[2-(4-fluorophenyl)-4-thiazolyl]ethenyl}-(E)-β-methoxycinnamate (Compounds Nos. 1a.394 and 1a.393 in Table1a)

a) 20 g (88 mol) of 4-chloromethyl-2-(4-fluorophenyl)thiazole and 23 g (88 mmol) of triphenylphosphine in 250 ml of tetrahydrofuran are refluxed for 24 h. Filtration with suction and washing with tetrahydrofuran result in 21 g (49%) of beige crystals (melting point >220° C.) of 2-(4-fluorophenyl)-4-thiazolylmethyltriphenylphosphonium chloride.

$^1$H—NMR ($CDCl_3$): δ=5.77 (d, 2H ); 6.98–8.22 (m, 20H) ppm.

b) A suspension of 10 g (20 mmol) of 2-(4-fluorophenyl)-4-thiazolylmethyltriphenylphosphonium chloride and 4.0 g (18 mmol) of methyl (E)-2-formyl-β-methoxycinnamate (see Example 3) in 50 ml of tetrahydrofuran is added to a suspension of 0.65 g (27 mmol) of NaH in 100 ml of tetrahydrofuran at 60° C. and the mixture is refluxed for 45 min.

After cooling, $NH_4Cl$ solution is added and the organic phase is separated off. The aqueous phase is extracted with methyl tert-butyl ether, and the combined organic phases are washed with water, dried over $Na_2SO_4$ and concentrated. The residue is chromatographed on silica gel (methyl tert-butyl ether/n-hexane=1:5). This results in 0.8 g (11%) of methyl 2-{2-[2-(4-fluorophenyl)-4-thiazolyl]-(Z)ethenyl}-(E)-β-methoxycinnamate as yellow oil which is eluted first and 2.3 g (33%) of methyl 2-{2-[2-(4-fluorophenyl)-4-thiazolyl]-(E)-ethenyl}-(E)-β-methoxycinnamate which is eluted second and is obtained in the form of beige crystals.

(Z), (E) isomer: $^1$H-NMR ($CDCl_3$): δ=3.50 (s, 3H ); 3.74 (s, 3H); 5.39 (s, 1H); 6.67 and 6.74 (AB, 2H); 6.89–7.94 (m, 9H) ppm.

(E), (E) isomer: Melting point 148°–150° C.

$^1$H-NMR ($CDCl_3$): δ=3.51 (s, 3H); 3.86 (s, 3H); 5.48 (s, 1H); 7.04–7.99 (m, 11H) ppm.

EXAMPLE 5

Preparation of methyl (E)- and (Z)-2-[2-(4-phenylphenyl)ethenyl]-(E)-β-methoxycinnamate (Compounds Nos. 1a.268 and 1a.269 in Table1a).

a) 115 g (0.4 mol) of methyl (E)-2-bromomethyl-β-methoxycinnamate and 105 g (0.4 mol) of triphenylphosphine in 700 ml of tetrahydrofuran are refluxed for 24 h. Filtration with suction and washing with tetrahydrofuran result in 181 g (82% yield) of (E)-2-(1-methoxy-2-methoxycarbonylethenyl)benzyltriphenylphosphonium bromide in the form of colorless crystals with melting point 189–°192° C.

$^1$H-NMR ($CDCl_3$): δ=3.45 (s, 3H); 3.57 (s, 3H); 4.95 (d, 2H); 5.06 (s, 1H); 6.96–7.84 (m, 19H) ppm.

b) A suspension of 3.3 g (18 mmol) of 4-phenylbenzaldehyde and 10 g (18 mmol) of E-2-(1-methoxy-2-methoxycarbonylethenyl)benzyltriphenylphosphonium bromide in 150 ml of tetrahydrofuran is added to a solution of 2.1 g (19.6 mmol) of lithium diisopropylamide in 100 ml of tetrahydrofuran at 0° C. After stirring at room temperature for 3 h, $NH_4Cl$ solution is added and the organic phase is separated off. The aqueous phase is extracted with methyl tert-butyl ether, and the combined organic phases are washed with water, dried over $Na_2SO_4$ and concentrated. The residue is chromatographed on silica gel (methyl tert-butyl ether/n-hexane=1:5). This results in 0.6 g (9%) of methyl 2-[2-(4-phenylphenyl)-(Z)-ethenyl]-(E)-β-methoxycinnamate as yellow oil which is eluted first and 1.1 g (16%) of methyl 2-[2-(4-phenylphenyl)-(E)-ethenyl]-(E)-β-methoxycinnamate which is eluted second and is obtained in the form of yellow crystals.

(Z), (E) isomer: $^1$H-NMR ($CDCl_3$): δ=3.52 (s, 3H); 3.74 (s, 3H); 5.33 (s, 1H); 6.51 and 6.58 (AB, 2H); 7.13–7.65 (m, 13H) ppm.

(E), (E) isomer: Melting point 110°–112° C.

$^1$H-NMR ($CDCl_3$): δ=3.50 (s, 3H); 3.83 (s, 3H); 5.44 (s, 1H); 7.10–7.74 (m, 15H) ppm.

EXAMPLE 6

Preparation of methyl 2-[2-(4-benzyloxyphenyl )-(E)-ethenyl]-(E)-β-methoxycinnamate (Compound No. 1a.264 in Table1a).

a) 0.1 g of potassium iodide is added to 20 g (70 mmol) of methyl (E)-2-bromomethyl-β-methoxycinnamate and 50 ml of trimethyl phosphite in 100 ml of dimethylformamide, and the mixture is stirred first at 40° C. for 1 h and then 100° C. for 1 h. The solvent and excess trimethyl phosphite are removed by distillation and the residue is taken up in dichloromethane. The solution is washed with water, dried over $Na_2SO_4$ and concentrated, and the residue is purified by column chromatography on silica gel (first methyl tert-butyl ether and then methanol). This results in 12 g (55%) of dimethyl (E)-2-(1-methoxy-2-methoxycarbonylethenyl)benzylphosphonate as brown oil.

$^1$H-NMR (CDCl$_3$): δ=3.18 (d, 2H); 3.53 (s, 3H); 3.61 (d, 6H); 3.79 (s, 3H); 5.38 (s, 1H); 7.18–7.50 (m, 4H) ppm.

b) A solution of 3.0 g (10 mmol) of dimethyl (E)-2-(1-methoxy- 2-methoxycarbonylethenyl)benzylphosphonate and 2.1 g (10 mmol) of 4-benzyloxybenzaldehyde in 50 ml of dimethylformamide is added dropwise at room temperature to 0.26 g (11 mmol) of NaH in 20 ml of dimethylformamide. The mixture is stirred for 3 h, and then NH$_4$Cl solution is added. After extraction with ethyl acetate, the organic phase is washed with water, dried over Na$_2$SO$_4$ and concentrated. Recrystallization from diisopropyl ether/n-hexane results in 1.9 g (48%) of pale yellow crystals of methyl 2-[2-(4-benzyloxyphenyl)-(E)-ethenyl]-(E)-β-methoxycinnamate of melting point 118°–120° C.

$^1$H-NMR (CDCl$_3$): δ=3.51 (s, 3H); 3.82 (s, 3H); 5.07 (s, 2H); 5.43 (s, 1H); 6.88–7.72 (m, 15H) ppm.

EXAMPLE 7

Preparation of methyl (E)-2-{2-[2-(4-fluorophenyl)-4-thiazolyl]ethyl}-β-methoxycinnamate (Compound No. 1a.347 in Table 1a).

3 g (7.6 mmol) of methyl 2-{2-[2-(4-fluorophenyl)-4thiazolyl]-(Z)-ethenyl}-(E)-β-methoxycinnamate in 100 ml of methanol are hydrogenated in the presence of 0.2 g of Pd/C (10%) under a gage pressure of 0.05 bar of hydrogen and at 20°–25° C. until hydrogen uptake ceases (1 h). The mixture is then filtered and concentrated.

Crystallization from diisopropyl ether/n-hexane results in 1.5 g (50%) of methyl (E)-2-{2-[2-(4-fluorophenyl)-4-thiazolyl]ethyl}-β-methoxycinnamate as orange crystals of melting point 157°–159° C.

H-NMR (CDCl$_3$): δ2.95–3.10 (m, 4H); 3.55 (s, 3H); 3.80 (s, 3H); 5.38 (s, 1H); 6.76–7.94 (m, 9H) ppm.

EXAMPLE 8

Preparation of methyl (E)-β-methoxy-2- [2-methyl-4-(1-methoximinoethyl)phenoxymethyl]cinnamate (Compound No. 1a.72 in Table 1a).

a) 25 g of dry molecular sieves (3 Å) are added to a solution of 52.6 g (0.35 mol) of 2-methyl-4-acetylphenol and 35.0 g (0.42 mol) of O-methylhydroxylamine hydrochloride in 150 ml of methanol, and the mixture is left to stand at room temperature for 24 h. The molecular sieves are filtered off and the solution is concentrated, the residue is taken up in dichloromethane, the solution is washed twice with water, dried over MgSO$_4$ and concentrated. This results in 58.3 g (93% yield) of 2-methyl-4-(1-methoximinoethyl)phenol as white solid of melting point 96°–99° C. which is >95% pure according to GC and $^1$H-NMR and therefore apparently is the more thermodynamically favored isomer with the E configuration of the C=N double bond.

$^1$H-NMR (CDCl$_3$): δ=2.19 (3H, s); 2.21 (3H, s); 3.96 (3H, s); 6.0 (O—H, s); 6.69 (1H, m); 7.30 (1H, m); 7.42 (1H, m) ppm.

b) 12.6 g of a 30 percent solution of sodium methanolate (0.07 mol) in methanol are added to 12.5 g (0.07 mol) of 2-methyl-4-(1-methoximinoethyl)phenol in 50 ml of methanol, and the solution is evaporated to dryness under reduced pressure. The residue is dissolved in 300 ml of dimethylformamide (DMF) and then 0.5 g of potassium iodide and a solution of 21.9 g (0.074 mol) of methyl (E)-β-methoxy-2-bromomethylcinnamate (see Example 2) in 100 ml of DMF are added. The mixture is stirred at room temperature for 8 hours and then evaporated to dryness under reduced pressure, the residue is dissolved in dichloromethane, and the organic phase is extracted twice with water, dried and concentrated. Trituration with methanol results in 25.0 g (93% yield) of methyl (E)-β-methoxy-2-[2-methyl-4-(1-methoximinoethyl)phenoxymethyl]cinnamate in the form of almost colorless crystals of melting point 58°–60° C. The product is >95% pure according to GC and $^1$H-NMR and therefore is the isomer with the E configuration of the C=N double bond.

$^1$H-NMR (CDCl$_3$): δ=2.17 (3H, s); 2.26 (3H, s); 3.55 (3H, s); 3.74 (3H, s); 3.94 (3H, s); 5.06 (2H, s); 5.38 (1H, s); 6.77 (1H, dd); 7.1–7.7 (6H, m) ppm.

EXAMPLE 9

Preparation of (E)-β-methoxy-2-[2-methyl-4-(1-methoximinoethyl)phenoxymethyl]cinnamic acid A mixture of 24.5 g (0.064 mol) of methyl (E)-β-methoxy-2-[2-methyl-4-(1-methoximinoethyl)phenoxymethyl] cinnamate (see Example 8), 4.6 g (0.07 mol) of 85 percent potassium hydroxide, 10 ml of water and 90 ml of methanol is refluxed for 16 hours, then cooled and poured into 1 l of ice-water. Aqueous hydrochloric acid is added dropwise to the stirred solution until the pH is 2, when the carboxylic acid separates as crystals. Filtration with suction and drying at 75° C. under reduced pressure result in 17.2 g (73% yield) of (E)-β-methoxy-2-[2-methyl-4-(1-methoximinoethyl)phenoxymethyl]cinnamic acid of melting point 154° C. in the form of white crystals. According to GC and $^1$H-NMR, the isomerism of the C=N double bond is unchanged after the hydrolysis.

$^1$H-NMR (CDCl$_3$): δ=2.14 (3H, s); 2.24 (3H, s); 3.73 (3H, s); 3.93 (3H, s); 5.04 (2H, s); 5.32 (1H, s); 6.74 (1H, dd); 7.1–7.6 (6H, m); 8–9 (COO—H, very broad signal) ppm.

EXAMPLE 10

Preparation of ethyl (E)-β-methoxy-2-[2-methyl-4-(1-methoximinoethyl)phenoxymethyl]cinnamate (Compound No. 1a. 74 in Table 1a).

0.4 g (0.0033 mol) of thionyl chloride is added to a stirred mixture of 1.1 g (0.003 mol) of (E)-β-methoxy-2-[2-methyl-4-(1-methoximinoethyl)phenoxymethyl]cinnamic acid (EXAMPLE 9), 0.9 g of pyridine and 20 ml of methyl tert-butyl ether at 0° C., and the mixture is then stirred at room temperature for one hour. 5 g of ethanol are then added dropwise, and the mixture is stirred at room temperature for a further hour. It is subsequently extracted with water, then with dilute hydrochloric acid and finally with sodium carbonate solution, and the organic phase is dried over MgSO$_4$ and evaporated to dryness under reduced pressure. 1.0 g (88% yield) of the abovementioned ethyl ester is obtained in the form of a pale yellow oil. Once again, according to GC and NMR, the isomerism of the C=N double bond remains E during the reaction.

$^1$H-NMR (CDCl$_3$): δ=1.10 (3H, tr); 2.19 (3H, s); 2.29 (3H, s); 3.76 (3H, s); 3.97 (3H, s); 3.99 (2H, q); 5.08 (2H, s); 5.37 (1H, s); 6.80 (1H, dd); 7.1–7.7 (6H, m) ppm.

EXAMPLE 11

Preparation of (E)-β-methoxy-2-[2-methyl-4-(1-methoximinoethyl) phenoxymethyl]cinnamide (Compound No. 1a. 88 in Table 1a).

0.4 g (0.0033 mol) of thionyl chloride is added to a stirred mixture of 1.1 g (0.003 mol) of (E)-β-methoxy-2-[2-methyl-4-(1-methoximinoethyl)phenoxymethyl]cinnamic acid (EXAMPLE 9), 0.9 g of pyridine and 20 ml of methyl tert-butyl ether at 0° C., and the mixture is then stirred at room temperature for 1 hour. Excess gaseous ammonia is subsequently passed in, and the mixture is then stirred at room temperature for one hour. It is subsequently extracted with water and then with dilute hydrochloric acid and finally with sodium carbonate solution, and the organic phase is dried over magnesium sulfate and evaporated to dryness under reduced pressure. The result is 1.0 g (88% yield) of the abovementioned amide in the form of colorless crystals of melting point 97°–99° C. Once again, according to GC and $^1$H-NMR, the isomerism of the C=N double bond remains E during the reaction.

$^1$H-NMR (CDCl$_3$): δ=2.20 (3H, s); 2.27 (3H, s); 3.75 (3H, s); 3.94 (3H, s); 5.0 (NH$_2$, broad signal); 5.12 (2H, s); 5.35 (1H, s); 6.83 (1H, dd); 7.2–7.7 (6H, m) ppm.

EXAMPLE 12

Preparation of methyl (E)-β-methoxy-2-(4-phenyl-2-thiazolyloxymethyl)cinnamate (Compound No. 1a. 181 in Table1a).

a) 54 g (0.35 mol) of β-chloroacetophenone are mixed with 200 ml of ethanol and 26.6 g of NH$_4$SCN. The mixture is refluxed for 15 min, the resulting NH$_4$Cl is removed by filtration with suction, and 175 ml of concentrated HCl/350 ml of H$_2$O are added. The mixture is refluxed for 2 hours, cooled to RT, a saturated Na$_2$CO$_3$ solution is added until the pH is 7, the mixture is stirred for 15 min, and the precipitate is filtered off.

It is washed with H$_2$O and dried under reduced pressure to give 40 g (67% yield) of 2-hydroxy-4-phenylthiazole as yellow solid of melting point 194° to 197° C.

$^1$H-NMR: (DMSO) 6.81 (s, 1H); 7.33–7.49 (m, 3H); 7.62–7.69 (m, 2H), 11.80 (br.s, 1H) ppm.

b) 1.2 g (0.007 mol) of 2-hydroxy-4-phenylthiazole, 2.1 g (0.0077 mol) of silver carbonate and 2.1 g (0.0074 mol) of methyl (E)-β-methoxy-2-bromomethylcinnamate (see Example 2) are stirred in 15 ml of DMF at 60° C. for 8 hours. The precipitate is filtered off and the DMF solution is poured into 100 ml of water, and the mixture is extracted with methyl tert-butyl ether. Drying and concentration of the organic phase result in a brown oil which is chromatographed on silica gel with cyclohexane/acetone (95:5). 1.5 g (56% yield) of methyl (E)-β-methoxy-2-(4-phenyl-2-thiazolyloxymethyl)cinnamate as yellowish oil are isolated as the main fraction.

$^1$H-NMR (CDCl$_3$): δ=3.52 (3H, s); 3.74 (3H, s); 5.38 (1H, s); 5.53 (2H, s); 6.82 (1H, s); 7.2–7.9 (9H, m) ppm.

IR: 1128, 1156, 1195, 1231, 1268, 1374, 1522, 1530, 1624, 1714 cm$^{-1}$.

EXAMPLE 13

Preparation of methyl (E)-β-methoxy-2-[2-(4-fluorophenyl)-4-thiazolylmethyloxy]cinnamate (Compound No. 1.71 in Table 1).

a) 11.2 g (0.05 mol) of 4-chloromethyl-2-(4-fluorophenyl)thiazole (see Example 4), 5.4 g (0.04 mol) of 2-hydroxyacetophenone, 7.5 g (0.055 mol) of potassium carbonate and 0.5 g of potassium iodide in 20 ml ethanol are refluxed for 24 hours. The mixture is filtered, the filtrate is concentrated, the residue is taken up in dichloromethane, the solution is extracted with dilute sodium hydroxide solution and then with water, and the organic phase is dried over MgSO$_4$. Removal of the solvent by distillation under reduced pressure results in a solid residue which is washed with diisopropyl ether to give 9.7 g (59% yield) of 2-[2-(4-fluorophenyl)-4-thiazolylmethyloxy]acetophenone as yellowish crystals of melting point 104°–106° C.

$^1$H-NMR (CDCl$_3$): δ=2.67 (3H, s); 5.36 (2H, s); 6.9–8.1 (9H, m) ppm.

b) A solution of 9.8 g (0.03 mol) of 2-[2-(4-fluorophenyl)-4-thiazolylmethyloxy]acetophenone in 80 ml of tetrahydrofuran is added dropwise to 3.0 g (0.033 mol) of dimethyl carbonate and 0.8 g (0.033 mol) of sodium hydride in 20 ml of tetrahydrofuran at 60° C. with stirring under nitrogen, and the mixture is then stirred at 60° C. for 1 hour. After cooling, first 5 ml of methanol and then 500 ml of water are added, and the mixture is acidified with dilute hydrochloric acid and extracted with methyl tert-butyl ether. The organic phase is washed with sodium bicarbonate solution, dried and concentrated. The result is 10.8 g (93% yield) of ω-methoxycarbonyl-2-[2-(4-fluorophenyl)-4-thiazolylmethyloxy]acetophenone as an ocher solid of melting point 86°–89° C.

$^1$H-NMR (CDCl$_3$): δ=3.62 (3H, s); 4.12 (2H, s); 5.31 (2H, s); 6.9–8.1 (9H, m) ppm.

c) One drop of concentrated sulfuric acid is added to a solution of 2.5 g (0.0065 mol) of β-methoxycarbonyl-2-[2-(4-fluorophenyl)-4-thiazolylmethyloxy]acetophenone and 0.83 g (0.0078 mol) of trimethyl orthoformate in 10 ml of methanol. The solution is refluxed for 4 hours and then concentrated under reduced pressure, the residue is taken up in toluene, and the toluene phase is washed with sodium bicarbonate solution. Drying and concentration result in 1.9 g of brownish oil. Chromatography on silica gel with toluene/acetone (98:2) results in 1.0 g (38% yield) of methyl (E)-β-methoxy-2-[2-(4-fluorophenyl)-4-thiazolylmethyloxy]cinnamate as brownish crystals of melting point 105–108° C.

$^1$H-NMR (CDCl$_3$): δ=3.51 (3H, s); 3.81 (3H, s); 5.31 (2H, s); 5.44 (1H, s); 6.9–8.1 (9H, m) ppm.

EXAMPLE 14

Preparation of methyl2-[1-(4-chlorophenyl)ethylideneaminoxymethyl]-(E)-β-methoxycinnamate (Compound No. 1a. 356 in Table1a).

3.1 g (18 mmol) of 4-chloroacetophenone oxime are added to 0.5 g (20 mmol) of sodium hydride in 80 ml of dimethylformamide at room temperature.

The mixture is stirred for 30 min and then 5 g (18 mmol) of methyl (E)-2-bromomethyl-β-methoxycinnamate in 20 ml of dimethylformamide are added dropwise. The mixture is then stirred for 1 h. After addition of NH$_4$Cl solution, the mixture is extracted with methyl tert-butyl ether, and the combined organic phases are washed with water, dried over Na$_2$SO$_4$ and concentrated. The residue is taken up in methyl tert-butyl ether/n-hexane (2:1), filtered through silica gel and concentrated.

The result is 5.8 g (86%) of methyl2-[1-(4-chlorophenyl)ethylideneaminoxymethyl]-(E)-β-methoxycinnamate as yellow oil.

H-NMR (CDCl$_3$): δ=2.20 (s, 3H); 3.50 (s, 3H); 3.78 (s, 3H); 5.20 (s, 2H); 5.36 (s, 1H); 7.20–7.57 (m, 8H) ppm.

EXAMPLE 15

Preparation of methyl (E)- and (Z)-β-methoxy-2-(3-methylphenoxy)cinnamate (Compounds Nos. 1.90 and 1.91 in Table a) A mixture of 50 g (0.324 mol) of 2-chloroacetophenone, 104.8 g (0.97 mol) of m-cresol, 45 g (0.326 mol) of potassium carbonate and 1 g of copper is heated at 120° C. for 16 hours. After cooling it is poured into water and extracted twice with methyl tert-butyl ether (MTB ether). The ether phase is washed five times with concentrated sodium hydroxide solution and then twice with water, dried and concentrated. 67.2 g (92% yield) of 2-(3-methylphenoxy)acetophenone remain as yellow oil.

$^1$H-NMR (CDCl$_3$): δ=2.35 (s, 3H); 2.65 (s, 3H); 6.79–7.84 (m, 8H) ppm.

b) 38.7 g (0.43 mol) of dimethyl carbonate are added to a suspension of 10.3 g (0.43 mol) of sodium hydride in 230 ml of THF and then, at 50° C., a solution of 67.2 g (0.30 mol) of 2-(3-methylphenoxy)acetophenone is added dropwise. The mixture is stirred at 50° C. for 3 hours, left to cool, 60 ml of methanol are added, and the mixture is stirred at room temperature overnight. It is acidified (pH 2) with 10 percent hydrochloric acid and extracted with MTB ether. The organic phase is washed with water, dried and concentrated. 79.5 g (93% yield) of methyl2-(3methylphenoxy)benzoylacetate remain as dark oil.

$^1$H-NMR (CDCl$_3$):[Keto form]δ=2.34 (s, 3H); 3.60 (s, 3H); 4.05 (s, 2H); 6.80–7.98 (m, 8H) ppm.

c) A solution of 5 g (18 mmol) of methyl2-(3-methylphenoxy)benzoylacetate in 30 ml of hexamethylphosphoric triamide (HMPT) is added dropwise to a suspension of 500 mg (21 mmol) of sodium hydride in 20 ml of HMPT, and the mixture is stirred until evolution of gas ceases. Then 2.5 g (20 mmol) of dimethyl sulfate are added dropwise, the mixture is stirred for 30 min, and then 30 ml of concentrated ammonia solution are added. The mixture is poured into water and extracted with MTB ether. The organic phase is dried and concentrated. Chromatography of the residue on silica gel with hexane/MTB ether yields in the first fractions 1.2 g (22%) of methyl (E)-β-methoxy-2-(3-methylphenoxy-)cinnamate (trans product) as yellow oil.

$^1$H-NMR (CDCl$_3$): δ=2.28 (s, 3H); 3.56 (s, 3H); 3.71 (s, 3H); 5.28 (s, 1H); 6.77–7.32 (m, 8H) ppm and then 0.5 g (9%) of methyl (Z)-β-methoxy-2-(3-methylphenoxy)cinnamate (cis product) as yellow oil $^1$H-NMR (CDCl$_3$): δ=2.33 (s, 3H); 3.70 (s, 3H); 3.75 (s, 3H); 5.21 (s, 1H); 6.77–7.36 (m, 8H) ppm.

EXAMPLE 16

Preparation of methyl (Z)- and (E)-β-ethoxy-2-methylcinnamate (Compounds Nos. 1.48 and 1.47 in Table 1)

9.6 g (50 mmol) of methyl2-methylbenzoylacetate, 6 g of ethyl bromide and 13.8 g of potassium carbonate are refluxed for 14 hours. The mixture is concentrated, the residue is taken up in methyl t-butyl ether and the solution is extracted 3x with water. The organic phase is dried over sodium sulfate and concentrated. The crude product is chromatographed on silica gel with 1,2-dichloroethane/cyclohexane (2:1). The result is 2.3 g (21%) of the (E) isomer (Compound No. 1.47) and 1.3 g (12%) of the (Z) isomer (Compound No. 1.48), each in the form of a colorless oil.

$^1$H-NMR (CDCl$_3$):

(Z) isomer (Compound No. 1.48): δ=1.24 (3H, t); 2.35 (3H, s); 3.70 (3H, s); 3.73 (2H, q); 5.07 (1H, s); 7.1–7.3 (4H, m) ppm.

(E) isomer (Compound No. 1.47): δ=1.37 (3H, t); 2.25 (3H, s); 3.53 (3H, s); 3.97 (2H, q); 5.32 (1H, s); 7.1–7.3 (4H, m) ppm.

EXAMPLE 17

Preparation of ethyl (E)-β-ethoxy-2-methylcinnamate (Compound No. 1.51 in Table 1)

19.2 g (100 mmol) of methyl2-methylbenzoylacetate and 17.7 g of triethyl orthoformate in 40 ml of ethanol plus 0.4 ml of concentrated sulfuric acid are refluxed for 16 hours. After cooling, 2 ml of pyridine are added and the mixture is then concentrated. The residue is taken up in methyl t-butyl ether and extracted 2xwith water. The organic phase is dried over sodium sulfate and concentrated. The crude product contains in addition to the title compound about 15% of the corresponding (E) methyl ester (Compound No. 1.47). Distillation results in 16.5 g (75%) of the title compound as colorless oil.

H-NMR (CDCl$_3$): δ=1.05 (3H, t); 1.37 (3H, t); 2.25 (3H, s); 3.97 (2H, q); 3.99 (2H, q); 5.32 (1H, s); 7.1–7.3 (4H, m) ppm.

EXAMPLE 18

Preparation of methyl (E)- and (Z)-β-methyl-2-(2-methylphenoxymethyl)cinnamate (Compounds Nos. 1a.109 and 1a.108 in Table1a)

a) 99.4 g (0.92 mol) of ortho-cresol and 102 g of potassium carbonate are mixed in 450 ml of ethanol. At 22° C., 202 g of 2-bromobenzyl bromide dissolved in 150 ml of ethanol are added dropwise. The mixture is refluxed for 8 h, then cooled and filtered. The filtrate is concentrated. The crude product is taken up in methyl t-butyl ether, washed with water and dried over sodium sulfate. The solvent is evaporated off, and then distillation results in 163 g (73%) of 2-(2-methylphenoxymethyl)bromobenzene as colorless oil which solidifies after some time (melting point 44°–45° C.).

b) 67 ml of n-butyllithium (1.6 molar in hexane) are added dropwise to 27.7 g (0.1 mol) of 2-(2-methylphenoxymethyl)bromobenzene dissolved in 200 ml of diethyl ether at 0° C. After 30 minutes, 11 g of N-methoxy-N-methylacetamide dissolved in 40 ml of diethyl ether are added dropwise at 0° C. The mixture is then stirred at room temperature for 3 hours, diluted with water, acidified with hydrochloric acid and extracted with diethyl ether. The combined organic phases are washed with water, dried over sodium sulfate and concentrated. The remaining crude product is chromatographed on silica gel with cyclohexane/methyl t-butyl ether (10:1). The result is 13.5 g (56%) of 2-(2-methylphenoxymethyl)acetophenone in the form of a colorless oil.

c) A solution of 20.4 g of trimethyl phosphonoacetate in 60 ml of tetrahydrofuran is added dropwise to a mixture of 2.8 g of sodium hydride and 450 ml of tetrahydrofuran at room temperature. After 20 minutes, a solution of 13.4 g (56 mmol) of 2-(2-methylphenoxymethyl)acetophenone in 45 ml of tetrahydrofuran is added dropwise. The reaction mixture is refluxed for 12 hours, then cooled, diluted with water and extracted with diethyl ether. The combined organic phases are washed with water, dried and concentrated. The crude product is chromatographed on silica gel with cyclohexane/methyl t-butyl ether (20:1).

10.9 g (66%) of (E) product (Compound No. 1a.109) and 5.0 g (30%) of (Z) product (Compound No. 1a. 108) are obtained, each in the form of a colorless oil.

$^1$H-NMR (CDCl$_3$):

(E) isomer (Compound No. 1a.109): δ=2.21 (3H,s); 2.50 (3H, s); 3.70 (3H, s); 4.97 (2H, s); 5.85 (1H, s); 6.8–7.6 (8H, m) ppm.

(Z) isomer (Compound No. 1a.108): δ=2.18 (3H, s); 2.25 (3H, s); 3.55 (3H, s); 4.95 (2H, AB); 5.98 (1H, s); 6.8–7.6 (8H, m) ppm.

EXAMPLE 19

Preparation of methyl (E)- and (Z)-β-methyl-2-methoxymethylcinnamate (Compounds No. 1.165 and 1.170 in Table 1)

A solution of 9.8 g of trimethyl phosphonoacetate in 30 ml of tetrahydrofuran is added dropwise to a mixture of 1.3 g of sodium hydride and 210 ml of tetrahydrofuran at room temperature. After 20 minutes, a solution of 5.9 g (36 mmol) of 2-methoxymethylacetophenone [see A. L. Maycock and G. A. Berchtold, J. Org. Chem. 35(8) (1970) 2532] in 30 ml of tetrahydrofuran is added dropwise. The reaction mixture is refluxed for 12 h, then cooled and diluted with water and extracted with diethyl ether. The combined organic phases are washed with water, dried and concentrated. The crude product (cis: trans 3:2) is chromatographed on silica gel with cyclohexane/methyl t-butyl ether (7:1). 4.5 g (57%) of (E) isomer (Compound No. 1.165) and 2.9 g (37%) of (Z) isomer (Compound No. 1.170) are obtained, each as a colorless oil.

$^1$H-NMR (CDCl$_3$):

E isomer (Compound No. 1.165): δ=2.48 (3H, s); 3.39 (3H, s); 3.77 (3H, s); 4.40 (2H, s); 5.82 (1H, s); 7.1–7.5 (4H, m) ppm.

Z isomer (Compound No. 1.170): δ=2.17 (3H, s); 3.38 (3H, s); 3.51 (3H, s); 4.35 (2H, AB); 6.01 (1H, s); 7.0–7.5 (4H, m) ppm.

EXAMPLE 20

Preparation of methyl (E)- and (Z)-β-methyl-2-bromomethylcinnamate (Compounds Nos. 1.167 and 1.171 in Table 1)

A solution of 48.7 g of boron tribromide in 18 ml of methylene chloride is added dropwise to a solution of 42.9 g (195 mmol) of methyl β-methyl-2-methoxymethylcinnamate (E:Z=3:2) in 470 ml of methylene chloride. The mixture is refluxed for 2 hours and then cooled, and 50 ml of methanol are added dropwise. The mixture is diluted with water and extracted with dichloromethane. The combined organic phases are dried over sodium sulfate and concentrated.

The crude product (50 g ; 95% yield) is a mixture of isomers (E:Z=3:2) of the title compound, which can be separated by chromatography.

$^1$H-NMR (CDCl$_3$):

(E) isomer (Compound No. 1.167): δ=2.51 (3H, s); 3.77 (3H, s); 5.00 (2H, s); 5.90 (1H, s); 7.1–7.5 (4H, m) ppm.

(Z) isomer (Compound No. 1.171): δ=2.25 (3H, s); 3.51 (3H, s); 5.00 (2H, s); 6.08 (1H, s); 7.0–7.5 (4H) ppm.

EXAMPLE 21

Preparation of methyl (E)- and (Z)-β-methyl-2-[2-methyl-4-(1-(E)-methoximinoethyl)phenoxy]methylcinnamate (Compounds Nos. 1a.113 and 1a.112 in Table1a)

15 g (56 mmol) of methylβ-methyl-2-bromomethylcinnamate ((E)/(Z) mixture 3:2), 10 g (56 mmol) of 2-methyl-4-(1-(E)-methoximinoethyl)phenol (see Example 8) and 11.6 g of potassium carbonate in 100 ml of dimethylformamide are stirred at 45° C. for 30 minutes. The mixture is concentrated, the residue is taken up in methyl t-butyl ether, and the solution is washed with water, dried over sodium sulfate and concentrated again.

The crude product is chromatographed on silica gel with n-hexane/methyl t-butyl ether (8:1).

7.2 g (35%) of (E) isomer (Compound No. 1a.113) and 4.8 g (23%) of (Z) isomer (Compound No. 1a.112) are obtained, each as a colorless oil.

$^1$H-NMR (CDCl$_3$):

(E) isomer (Compound No. 1a.113): δ=2.17 (3H, s); 2.25 (3H, s); 2.50 (3H, s); 3.72 (3H, s); 3.97 (3H, s); 5.03 (2H, s); 5.85 (1H, s); 6.8–7.6 (7H)-ppm.

(Z) isomer (Compound No. 1a.112): δ=2.17 (3H, s); 2.18 (3H, s); 2.26 (3H, s); 3.53 (3H, s); 3.97 (3H, s); 4.98 (2H, AB); 6.00 (1H, s); 6.8–7.6 (7H)ppm.

EXAMPLE 22

Preparation of methyl (E)-3-methoxy-3-(7-bromo-1-naphthyl)acrylate (compound No. 1b.17 in Table 1b)

a) A solution of 105 g (0.42 mol) of 1-acetyl-7-bromonaphthalene in 500 ml of tetrahydrofuran is slowly added dropwise under an argon atmosphere to a suspension of 14 g (0.58 mol) of NaH and 52 g (0.58 mol) of dimethyl carbonate in 500 ml of tetrahydrofuran at 60° C. The mixture is then stirred at 60° C. for a further 2 h. After cooling, 30 ml of methanol are added, the mixture is poured onto ice-water and acidified with 10% strength hydrochloric acid. After extraction with methyl tert-butyl ether, the combined organic phases are washed with NaHCO$_3$ solution and water, dried over Na$_2$SO$_4$ and concentrated. The residue comprises 127 g (98%) of methyl 7-bromo-1-naphthoylacetate as brownish crystals with a melting point of 82°–83° C.

$^1$H-NMR (CDCl$_3$): keto form: δ=3.78 (s, 3H); 4.12 (s, 2H); 7.40–8.01 (m, 5H); 9.17 (s, 1H) ppm The signals of the relevant enol form also appear to a minor extent (about 30%):

δ=3.83 (s, 3H); 5.48 (s, 1H); 7.40–8.01 (m, 5H); 8.51 (s, 1H) ppm b) 93 g (0.68 mol) of potassium carbonate are added to a stirred mixture of 189 g (0.61 mol) of methyl 7-bromo-1-naphthoylacetate and 500 ml of N,N'-dimethylpropyleneurea, and the mixture is stirred at 40° C. for 2 h. It is subsequently cooled to 0°–5° C., and a mixture of 85 g (0.68 mol) of dimethyl sulfate and 50 ml of N,N'-dimethylpropyleneurea is added dropwise. The mixture is then stirred at 40° C. for a further 2 h, and subsequently water and methyl tert-butyl ether are added. The aqueous phase is extracted once more with methyl tert-butyl ether, and the combined organic phases are dried over Na$_2$SO$_4$ and concentrated. The residue is taken up in 500 ml of N,N'-dimethylpropyleneurea, and 2.7 g (0.11 mol) of NaH are added. The mixture is stirred at room temperature for 15 h. Subsequently, 20 ml of methanol are added and the mixture is diluted with water and extracted with methyl tert-butyl ether. The organic phase is washed with water, dried over Na$_2$SO$_4$ and concentrated. The residue is recrystallized from methanol to give 102 g (52%) of methyl (E)-3-methoxy-3-(7-bromo-1-naphthyl)acrylate in the form of colorless crystals of melting point 111°–113° C.

$^1$H-NMR (CDCl$_3$): δ=3.48 (s, 3H); 3.88 (s, 3H); 5.58 (s, 1H); 7.44 (t, 1H); 7.54 (m, 2H); 7.72 (d, 1H); 7.86 (d, 1H); 7.90 (s, 1H) ppm The isomeric methyl (Z)-3-methoxy-3-(7-bromo-1-naphthyl)acrylate can be obtained in the form of colorless crystals of melting point 96°–97 ° C. by column chromatography of the mother liquor on silica gel (cyclohexane/toluene 2:1 to 1:10).

$^1$H-NMR (CDCl$_3$): δ=3.51 (s, 3H); 3.78 (s, 3H); 5.25 (s, 1H); 7.50 (d, 2H); 7.61 (d, 1H); 7.86 (d, 1H); 7.90 (t, 1H); 8.26 (s, 1H) ppm

EXAMPLE 23

Preparation of methyl (E)-3-methoxy-3-(7-phenyl-1-naphthyl)acrylate (compound No. 1b.1 in Table 1b)

1.4 g (4.4 mmol) of methyl (E)-3-methoxy-3-(7-bromo-1-naphthyl)acrylate, 0.36 g (0.3 mmol) of tetrakis(tri-phenylphosphine)palladium and 0.76 g (6.2 mmol) of phenylboric acid are mixed with 75 ml of dimethoxyethane and 31 ml of 20% strength Na₂CO₃ solution and subsequently stirred at 80° C. for 8 h. The mixture is extracted with methyl tert-butyl ether, and the organic phase is washed 2×with water, dried over Na₂SO₄ and concentrated. The residue is purified by column chromatography on silica gel (first cyclohexane and then toluene). This results in 0.98 g (71%) of methyl (E)-3-methoxy-3-(7-phenyl-1-naphthyl)acrylate in the form of yellowish crystals of melting point 62°–64° C.

¹H-NMR (CDCl₃): δ=3.46 (s, 3H); 3.88 (s, 3H); 5.61 (s, 1H); 7.31–7.55 (m, 5H); 7.63 (d, 2H); 7.71 (d, 1H); 7.85–7.93 (m, 3H) ppm

EXAMPLE 24

Preparation of methyl (E)-3-methoxy-3-(7-methyl-1-naphthyl)acrylate (compound No. 1b.11 in Table 1b)

a) A solution of 154 g (0.8 mol) of 1-acetyl-7-methylnaphthalene in 500 ml of tetrahydrofuran is slowly added dropwise to a suspension of 35 g (1.2 mol) of NaH and 104 g (1.2 mol) of dimethyl carbonate in 750 ml of tetrahydrofuran at 60° C. under a nitrogen atmosphere. The mixture is then stirred at 60° C. for 2 h.

After cooling, 100 ml of methanol are added, the mixture is poured into ice-water and acidified with 10% strength hydrochloric acid. After extraction with methyl tert-butyl ether, the combined organic phases are washed with NaHCO₃ solution and water, dried over Na₂SO₄ and concentrated. The residue comprises 177 g (88%) of methyl7-methyl-1-naphthoyl acetate as reddish brown oil.

¹H-NMR (CDCl₃): keto form: δ=2.52 (s, 3H); 3.73 (s, 3H); 4.08 (s, 2H); 7.29–7.46 (m, 2H ); 7.68–8.00 (m, 3H); 8.59 (s, 1H) ppm The signals of the relevant enol form also appear to a minor extent (about 30%):

δ=2.51 (s, 3H); 3.81 (s, 3H); 5.49 (s, 1H); 7.29–8.00 (m, 5H); 8.10 (s, 1H) ppm b) 30 g (0.22 mol) of potassium carbonate are added to a stirred mixture of 48 g (0.2 mol) of methyl 7-methyl-1-naphthoylacetate and 250 ml of N,N'-di-methylpropyleneurea, and the mixture is stirred at 40° C. for 2 h. It is subsequently cooled to 0°–5° C., and a mixture of 27.7 g (0.22 mol) of dimethyl sulfate and 50 ml of N,N'-dimethylpropyleneurea is added dropwise. The mixture is then stirred at 40° C. for a further 2 h and subsequently water and methyl tert-butyl ether are added. The aqueous phase is extracted once more with methyl tert-butyl ether, and the combined organic phases are dried over Na₂SO₄ and concentrated. The residue is taken up in 200 ml of N,N'-dimethylpropyleneurea, and 2.2 g (0.1 mol) of NaH are added. The mixture is stirred at room temperature for 15 h and then 50 ml of methanol are added, and the mixture is diluted with water and extracted with methyl tert-butyl ether. The organic phase is washed with water, dried over Na₂SO₄ and concentrated. The residue is purified by column chromatography on silica gel (first cyclohexane and then toluene). This results in 40.4 g (80%) of methyl (E)-3-methoxy-3-(7-methyl-1-naphthyl)acrylate as brown oil.

¹H-NMR (CDCl₃): δ=2.48 (s, 3H); 3.45 (s, 3H); 3.87 (s, 3H); 5.58 (s, 1H); 7.21–7.52 (m, 4H); 7.72–7.90 (m, 2H) ppm

EXAMPLE 25

Preparation of methyl (E)-3-methoxy-3-(7-phenoxymethyl-1-naphthyl)acrylate (compound No. 1b.20 in Table 1b)

a) 6.2 g (0.024 mol) of methyl (E)-3-methoxy-3-(7-methyl-1-naphthyl)acrylate and 7.1 g (0.025 mol) of 1,3-dibromo-5,5-dimethylhydantoin in 100 ml of dry tetrachloromethane are refluxed while irradiating with a halogen lamp for 75 min. The mixture is subsequently filtered with suction, and the filtrate is filtered once more through a layer of silica gel. The solvent is removed by distillation, and the residue is recrystallized from methyl tert-butyl ether. This results in 6. g (67%) of methyl (Z)-2-bromo-3-methoxy-3-(7-bromomethyl-1-naphthyl)acrylate as colorless crystals of melting point 116°–119° C.

¹H-NMR (CDCl₃): δ=3.40 (s, 3H); 3.41 (s, 3H); 4.63 (s, 2H); 7.40 (d, 1H); 7.50–7.61 (m, 2H); 775 (s, 1H); 7.88–7.99 (n, 2H) ppm b) A solution of 0.7 g (5.5 mmol) of potassium phenolate in 25 ml of dimethylformamide (DMF) is added dropwise to a solution of 2.1 g (5 mmol) of methyl (Z)-2-bromo-3-methoxy-3-(7-bromomethyl-1-naphthyl)acrylate in 30 ml of DMF at room temperature, and the mixture is stirred at room temperature for 4 hours. It is then evaporated to dryness under reduced pressure, the residue is dissolved in ethyl acetate, and the organic phase is extracted twice with water, dried and concentrated. This results in 1.85 g (87%) of methyl (Z)-2-bromo-3-methoxy-3-(7-phenoxymethyl-1-naphthyl)acrylate as brownish oil.

¹H-NMR (CDCl₃): δ=3.39 (s, 6H); 5.21 (s, 2H); 6.91–7.32 (m, 5H); 7.39 (d, 1H); 7.52 (t, 1H); 7.63 (d, 1H); 7.80 (s, 1H); 7.89–8.00 (m, 2H) ppm c) 1.64 g (3.8 mmol) of methyl (Z)-2-bromo-3-methoxy-3-(7-phenoxymethyl-1-naphthyl)acrylate are dissolved in 30 ml of toluene and, after addition of 2.2 g (7.6 mmol) of tributyltin hydride and a few mg of α,α'-azoisobutyronitrile, the mixture is refluxed for 15 hours. It is then concentrated, and the residue is purified by column chromatography on silica gel (first cyclohexane and then toluene). The tin compounds are eluted first, and the following fraction contains 0.89 g (66%) of methyl (E)-3-methoxy-3-(7-phenoxymethyl-1–1-naphthyl)acrylate.

¹H-NMR (CDCl₃): δ=3.43 (s, 3H); 3.82 (s, 3H); 5.19 (s, 2H); 5.56 (s, 1H); 6.90–7.56 (m, 8H); 7.78 (s, 1H); 7.84–7.91 (m, 2H) ppm 0.14 g (10%) of the isomeric methyl (Z)-3-methoxy-3-(7-phenoxymethyl-1-naphthyl)acrylate is obtained as second product.

¹H-NMR (CDCl₃): δ=3.50 (s, 3H); 3.76 (s, 3H); 5.22 (s, 2H); 5.24 (s, 1H); 6.92–7.97 (m, 10H); 8.08 (s, 1H) ppm

We claim:

1. A β-substituted cinnamic acid derivative of the formula 1,

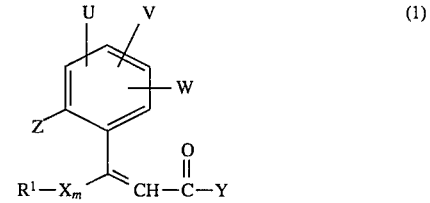

where

R¹ is unsubstituted or halogen-, C₁–C₆-alkoxy-, C₁–C₆-alkylthio- or C₃–C₆-cycloalkyl-substituted C₁–C₈-alkyl, C₂–C₈-alkenyl, C₃–C₈-alkynyl, C₃–C₈-cycloalkyl or C₃–C₈-cycloalkenyl, —X— is —O—, —S—,

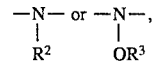

m is 1,

—Y is —OR⁴, —O—N=CR⁵R⁶, —NR⁷R⁸, —N(OR⁹)R¹⁰ or —SR¹¹, where the substituents R² to $R^{11}$ are, independently of one another, identical or different and each is unsubstituted or halogen-, $C_1$–$C_6$-alkoxy-, $C_1$–$C_6$-alkylthio- or $C_3$–$C_6$-cycloalkyl-substituted, $C_1$–$C_8$-alkyl, $C_2$–$C_8$-alkenyl, $C_2$–$C_8$-alkynyl, $C_3$–$C_8$-cycloalkyl or $C_3$–$C_8$-cycloalkenyl, Z is halogen, nitro, cyano, unsubstituted or substituted alkyl, unsubstituted or substituted cycloalkyl, unsubstituted or substituted aralkyl, unsubstituted or substituted aryloxyalkyl, unsubstituted or substituted arylthioalkyl, unsubstituted or substituted hetarylalkyl, unsubstituted or substituted hetaryloxyalkyl, unsubstituted or substituted hetarylthioalkyl, unsubstituted or substituted alkenyl, unsubstituted or substituted aralkenyl, unsubstituted or substituted aryloxyalkenyl, unsubstituted or substituted arylthioalkenyl, unsubstituted or substituted hetarylalkenyl, unsubstituted or substituted hetaryloxyalkenyl, unsubstituted or substituted hetarylthioalkenyl, unsubstituted or substituted alkynyl, unsubstituted or substituted arylalkynyl, unsubstituted or substituted hetarylalkynyl, unsubstituted or substituted aryl, unsubstituted or substituted hetaryl, unsubstituted or substituted arylazo, unsubstituted or substituted acylamino, —$OR^{12}$, —$SR^{13}$, —$SOR^{14}$, —$SO_2R^{15}$, —$COOR^{16}$, —$CONR^{17}R^{18}$, —$COR^{19}$, —$CR^{20}$=$NR^{21}$, —$N$=$CR^{22}R^{23}$, —$CR^{24}$=$N$—$OR^{25}$, —$CR^{25}R^{26}$—$O$—$N$=$CR^{27}R^{28}$, —$CH_2$—$OCOR^{39}$ or —$NR^{37}R^{38}$, provided that when U, V and W are simultaneously hydrogen, Z is not methoxy, where $R^{12}$ to $R^{28}$ and $R^{38}$ and $R^{39}$ are identical or different and are hydrogen, unsubstituted or substituted alkyl, unsubstituted or substituted alkenyl, unsubstituted or substituted alkynyl, unsubstituted or substituted cycloalkyl, unsubstituted or substituted cycloalkylalkyl, unsubstituted or substituted aryl, unsubstituted or substituted hetaryl, unsubstituted or substituted aralkyl, unsubstituted or substituted hetarylalkyl, unsubstituted or substituted aryloxyalkyl, unsubstituted or substituted arylthioalkyl, unsubstituted or substituted hetaryloxyalkyl or unsubstituted or substituted hetarylthioalkyl, and $R^{37}$ is hydrogen or $C_1$–$C_4$-alkyl, and where U, V and W are identical or different and are hydrogen or have one of the meanings specified for Z, or where two of the groups Z, U, V or W in adjacent positions on the phenyl ring may together with the carbon atoms to which they are attached form an unsubstituted or substituted five- or six-membered aromatic or aliphatic ring which is fused onto the phenyl ring and may contain one to three hetero atoms (N, S, O), provided that said derivative of formula 1 does not include 3-methylmercapto-3-(1-naphythyl)acrylic acid ethyl ester and an alkyl ester of (p-terphenyl)-2'-carboxylic acid-3-(2-carboxy-1-methoxy vinyl)-2'-methyl ester.

2. A compound of the formula 1a

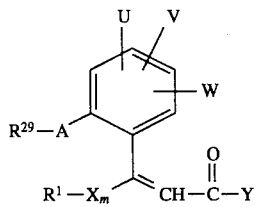

where $R^1$ is unsubstituted or halogen-, $C_1$–$C_6$-alkoxy-, $C_1$–$C_6$-alkylthio- or $C_3$–$C_6$-cycloalkyl-substituted, $C_1$–$C_8$-alkyl, $C_2$–$C_8$-alkenyl, $C_2$–$C_8$-alkynyl, $C_3$–$C_8$-cycloalkyl or $C_3$–$C_8$-cycloalkenyl, and $R^1$ can also be chlorine or bromine with the restriction that m is 0, —X— is —O—, —S—,

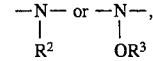

m is 0 or 1,

—Y is —$OR^4$, —O—N=$CR^5R^6$, —$NR^7R^8$, —N($OR^9$)$R^{10}$ or —$SR^{11}$, where the substituents $R^2$ to $R^{11}$ are, independently of one another, identical or different and each is unsubstituted or halogen-, $C_1$–$C_6$-alkoxy-, $C_1$–$C_6$-alkylthio- or $C_3$–$C_6$-cycloalkyl-substituted, $C_1$–$C_8$-alkyl, $C_2$–$C_8$-alkenyl, $C_2$–$C_8$-alkynyl, $C_3$–$C_8$-cycloalkyl or $C_3$–$C_8$-cycloalkenyl, and $R^2$, $R^3$ and $R^5$ to $R^{11}$ are also hydrogen when $R^4$ is not ethyl or t-butyl and when m is 0, U, V and W are identical or different and are hydrogen or halogen, nitro, cyano, unsubstituted or substituted alkyl, unsubstituted or substituted cycloalkyl, unsubstituted or substituted aralkyl, unsubstituted or substituted aryloxyalkyl, unsubstituted or substituted arylthioalkyl, unsubstituted or substituted hetarylalkyl, unsubstituted or substituted hetaryloxyalkyl, unsubstituted or substituted hetarylthioalkyl, unsubstituted or substituted alkenyl, unsubstituted or substituted aralkenyl, unsubstituted or substituted aryloxyalkenyl, unsubstituted or substituted arylthioalkenyl, unsubstituted or substituted hetarylalkenyl, unsubstituted or substituted hetaryloxyalkenyl, unsubstituted or substituted hetarylthioalkenyl, unsubstituted or substituted alkynyl, unsubstituted or substituted arylalkynyl, unsubstituted or substituted hetarylalkynyl, unsubstituted or substituted aryl, unsubstituted or substituted hetaryl, unsubstituted or substituted arylazo, unsubstituted or substituted acylamino —$OR^{12}$, —$SR^{13}$, —$SOR^{14}$, —$SO_2R^{15}$, —$COOR^{16}$, —$CONR^{17}R^{18}$, —$COR^{19}$, —$CR^{20}$=$NR^{21}$, —$N$=$CR^{22}R^{23}$, —$CR^{24}$=$N$—$OR^{25}$, —$CR^{25}R^{26}$—$O$—$N$=$CR^{27}R^{28}$, —$CH_2$—$OCOR^{39}$ or —$NR^{37}R^{38}$, where $R^{12}$ to $R^{28}$ and $R^{38}$ and $R^{39}$ are identical or different and are hydrogen, unsubstituted or substituted alkyl, unsubstituted or substituted alkenyl, unsubstituted or substituted alkynyl, unsubstituted or substituted cycloalkyl, unsubstituted or substituted cycloalkylalkyl, unsubstituted or substituted aryl, unsubstituted or substituted hetaryl, unsubstituted or substituted aralkyl, unsubstituted or substituted hetarylalkyl, unsubstituted or substituted aryloxyalkyl, unsubstituted or substituted arylthioalkyl, unsubstituted or substituted hetaryloxyalkyl or unsubstituted or substituted hetarylthioalkyl, and $R^{37}$ is hydrogen or $C_1$–$C_4$-alkyl, and $R^{19}$ is not hydrogen and $R^{12}$ is not unsubstituted or substituted alkyl when m is 0, or where two of the groups U, V or W in adjacent positions on the phenyl ring may together with the carbon atoms to which they are attached form an unsubstituted or substituted five- or six-membered aromatic or aliphatic ring which is fused onto the phenyl ring and may contain one to three hetero atoms (N, S, O), and —A— is —C=C—, —$CR^{30}$—$CR^{31}$—, —$CHR^{30}$—$CHR^{31}$—, —O—$CHR^{31}$—, —O—CO—, —NR³⁰CO—, —S—CHR³¹, —N=CR³¹—, —COO—CHR³¹—, —O—N=CR³¹—, —R³⁰—C=N—O—CHR³¹, —CR³⁰=N—, —N=N— or —CHR³⁰, and where R²⁹ is unsubstituted or substituted alkyl, unsubstituted or substituted alkenyl, unsubstituted or substituted alkynyl, unsubstituted or substituted aralkyl, unsubstituted or substituted hetarylalkyl, unsubstituted or substituted aryloxyalkyl, unsubstituted or substituted hetaryloxyalkyl or hetarylthioalkyl or unsubstituted or substituted aryl or unsubstituted or substituted hetaryl and R³⁰ and R³¹ are identical or different and are straight-chain or branched $C_1$–$C_4$-alkyl or hydrogen.

3. A compound of the formula 1a as claimed in claim 2, where R²⁹ is five- or six-membered aryl or hetaryl which is unsubstituted or substituted one or more times by halogen, $C_1$–$C_{12}$-alkyl, $C_1$–$C_{12}$-haloalkyl, $C_2$–$C_{12}$-alkenyl, $C_2$–$C_{12}$-alkynyl, unsubstituted or substituted aryl, unsubstituted or substituted hetaryl, unsubstituted or substituted aralkyl, $C_1$–$C_{12}$-alkoxy, $C_1$–$C_{12}$-haloalkoxy, $C_2$–$C_{12}$-alkenyloxy, $C_2$–$C_{12}$-alkynyloxy, unsubstituted or substituted aryloxy, formyl, $C_1$–$C_{12}$-acyl, cyano, trifluoromethyl, nitro or —CR³²=N—OR³³ or may be fused to a benzene ring, where R³², is hydrogen or $C_1$–$C_4$-alkyl and R³³ is hydrogen, $C_1$–$C_8$-alkyl, $C_2$–$C_8$-alkenyl or $C_2$–$C_8$-alkynyl.

4. A compound of the formula 1a as claimed in claim 2, where R²⁹ is unsubstituted or singly or multiply halogen-, $C_1$–$C_{12}$-alkyl-, $C_2$–$C_{12}$-alkenyl-, unsubstituted or substituted aryl-, unsubstituted or substituted hetaryl-, unsubstituted or substituted aralkyl-, $C_1$–$C_{12}$-alkoxy-, $C_1$–$C_{12}$-haloalkoxy-, $C_2$–$C_{12}$-alkenyloxy, $C_2$–$C_{12}$-alkynyloxy-, unsubstituted or substituted aryloxy-, formyl-, $C_1$–$C_{12}$-acyl-, cyano-, trifluoromethyl-, nitro- or —CR³²=NOR³³- substituted or possibly benzene-fused phenyl, furyl, thienyl, pyrrolyl, isoxazolyl, isothiazolyl, oxazolyl, thiazolyl, 1,2,4-oxadiazolyl, 1,2,4-thiadiazolyl, 1,3,4-oxadiazolyl, 1,3,4-thiadiazolyl, imidazolyl, pyrazolyl, 1,2,4-triazolyl, 1,3,4-triazolyl, pyridinyl, pyrimidinyl, pyridazinyl, pyrazinyl, 1,3,5-triazinyl or 1,2,4-triazinyl.

5. A compound of the formula 1b

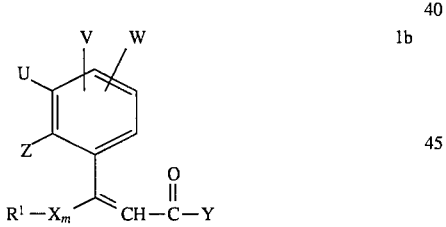

where Z and U together with the carbon atoms to which they are attached form an unsubstituted or substituted five- or six-membered aromatic ring which may contain one to three hetero atoms (N, O or S) and where $R_1$ is unsubstituted or halogen-, $C_1$–$C_6$-alkoxy-, $C_1$–$C_6$-alkylthio- or $C_3$–$C_6$-cycloalkyl-substituted $C_1$–$C_8$-alkyl, $C_2$–$C_8$-alkenyl, $C_2$–$C_8$-alkynyl, $C_3$–$C_8$-cycloalkyl or $C_3$–$C_8$-cycloalkenyl, and R¹ can also be chlorine or bromine when m is 0, —X— is —O—, —S—,

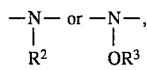

m is 0 or 1,

—Y is —OR⁴, —O—N=CR⁵R⁶, —NR⁷R⁸, —N(OR⁹)R¹⁰ or —SR¹¹, where the substituents R² to R¹¹ are, independently of one another, identical or different and each is unsubstituted or halogen-, $C_1$–$C_6$-alkoxy-, $C_1$–$C_6$-alkylthio- or $C_3$–$C_6$-cycloalkyl-substituted, $C_1$–$C_8$-alkyl, $C_2$–$C_8$-alkenyl, $C_2$–$C_8$-alkynyl, $C_3$–$C_8$-cycloalkyl or $C_3$–$C_8$-cycloalkenyl, and R², R³ and R⁵ to R¹¹ are also hydrogen with the restriction that R⁴ is not ethyl or t-butyl when m is 0, V and W are identical or different and are hydrogen or halogen, nitro, cyano, unsubstituted or substituted alkyl, unsubstituted or substituted cycloalkyl, unsubstituted or substituted aralkyl, unsubstituted or substituted aryloxyalkyl, unsubstituted or substituted arylthioalkyl, unsubstituted or substituted hetarylalkyl, unsubstituted or substituted hetaryloxyalkyl, unsubstituted or substituted hetarylthioalkyl, unsubstituted or substituted alkenyl, unsubstituted or substituted aralkenyl, unsubstituted or substituted aryloxyalkenyl, unsubstituted or substituted arylthioalkenyl, unsubstituted or substituted hetarylalkenyl, unsubstituted or substituted hetaryloxyalkenyl, unsubstituted or substituted hetarylthioalkenyl, unsubstituted or substituted alkynyl, unsubstituted or substituted arylalkynyl, unsubstituted or substituted hetarylalkynyl, unsubstituted or substituted aryl, unsubstituted or substituted hetaryl, unsubstituted or substituted arylazo, unsubstituted or substituted acylamino, —OR¹², —SR¹³, —SOR¹⁴, —SO₂R¹⁵, —COOR¹⁶, —CONR¹⁷R¹⁸, —COR¹⁹, —CR²⁰=NR²¹, —NH=CR²²R²³, —CR²⁴=N—OR²⁵, —CR²⁵R²⁶—O—N=CR²⁷R²⁸, —CH₂—OCOR³⁹ or —NR³⁷R³⁸, where R¹² to R²⁸ and R³⁸ and R³⁹ are identical or different and are hydrogen, unsubstituted or substituted alkyl, unsubstituted or substituted alkenyl, unsubstituted or substituted alkynyl, unsubstituted or substituted cycloalkyl, unsubstituted or substituted cycloalkylalkyl, unsubstituted or substituted aryl, unsubstituted or substituted hetaryl, unsubstituted or substituted aralkyl, unsubstituted or substituted hetarylalkyl, unsubstituted or substituted aryloxyalkyl, unsubstituted or substituted arylthioalkyl, unsubstituted or substituted hetaryloxyalkyl or unsubstituted or substituted hetarylthioalkyl, and R³⁷ is hydrogen or $C_1$–$C_4$-alkyl and R¹⁹ is not hydrogen and R¹² is not unsubstituted or substituted alkyl when m is 0, or two of the groups V and W in adjacent positions on the phenyl ring may together with the carbon atoms to which they are attached form an unsubstituted or substituted five- or six-membered aromatic or aliphatic ring which is fused onto the phenyl ring and may contain one to three hetero atoms (N, S, O), provided that said compound does not include 3-methylmercapto-3(1-naphthyl)acrylic acid ethyl ester.

6. A compound of the formula 1b as claimed in claim 5, where the group

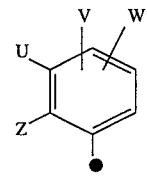

is one of the following groups:

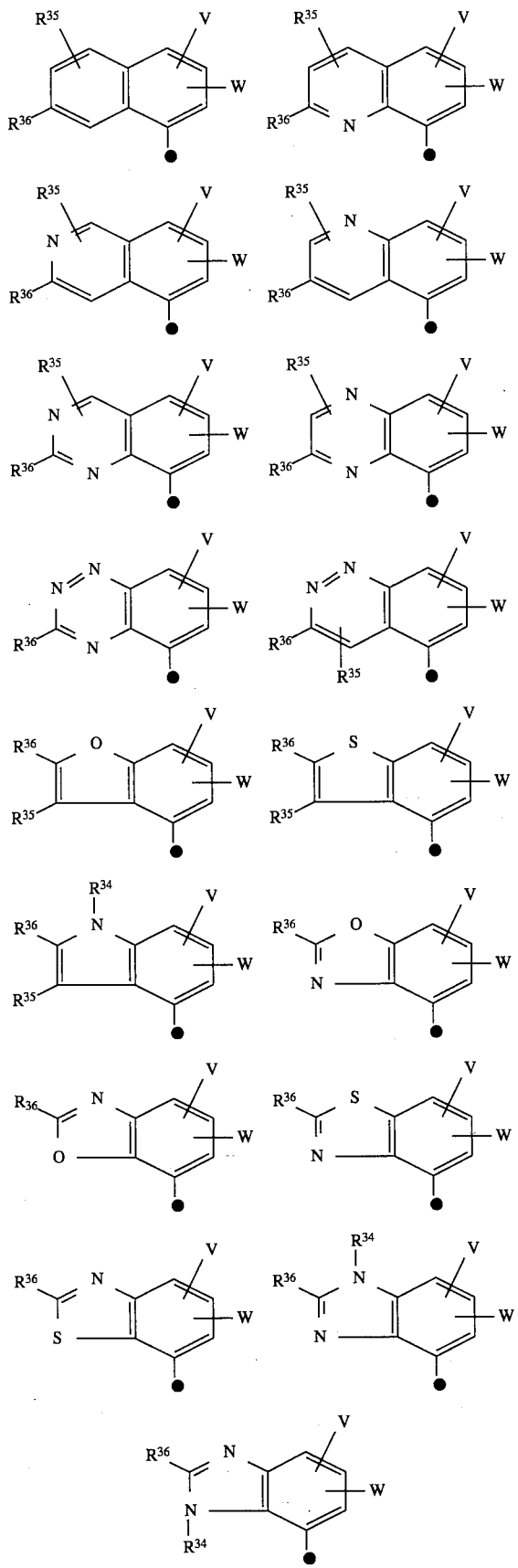

where $R^{36}$ has the meanings specified for $R^{29}$ in claim 3 or is halogen or is $OR^{12}$, $SR^{13}$ or $NR^{37}R^{38}$ where $R^{12}$, $R^{13}$, $R^{37}$ and $R^{38}$ have the meanings stated in claim 1, $R^{34}$ is hydrogen or $C_1$–$C_4$-alkyl, and $R^{35}$ is hydrogen, methyl, methoxy, trifluoromethyl, fluorine, chlorine, bromine, cyano or nitro, wherein • denotes the point of attachment.

7. A crop-treatment agent with fungicidal, insecticidal or acaricidal action containing an effective amount of a compound of the formula 1

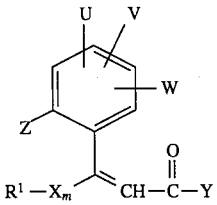

where $R^1$ is unsubstituted or halogen-, $C_1$–$C_6$-alkoxy-, $C_1$–$C_6$-alkylthio- or $C_3$–$C_6$-cycloalkyl-substituted $C_1$–$C_8$-alkyl, $C_2$–$C_8$-alkenyl, $C_2$–$C_8$-alkynyl, $C_3$–$C_8$-cycloalkyl or $C_3$–$C_8$-cycloalkenyl, —X— is —O—, —S—,

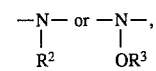

m is 1,

—Y is —$OR^4$, —O—N=$CR^5R^6$, —$NR^7R^8$, —N($OR^9$)$R^{10}$ or —$SR^{11}$, where the substituents $R^2$ to $R^{11}$ are, independently of one another, identical or different and each is unsubstituted or halogen-, $C_1$–$C_6$-alkoxy-, $C_1$–$C_6$-alkylthio- or $C_3$–$C_6$-cycloalkyl-substituted, $C_1$–$C_8$-alkyl, $C_2$–$C_8$-alkenyl, $C_2$–$C_8$-alkynyl, $C_3$–$C_8$-cycloalkyl or $C_3$–$C_8$-cycloalkenyl, and $R^2$, $R^3$ and $R^5$ to $R^{11}$ are also hydrogen with the restriction that $R^4$ is not ethyl or t-butyl Z is halogen, nitro, cyano, unsubstituted or substituted alkyl, unsubstituted or substituted cycloalkyl, unsubstituted or substituted aralkyl, unsubstituted or substituted aryloxyalkyl, unsubstituted or substituted arylthioalkyl, unsubstituted or substituted hetarylalkyl, unsubstituted or substituted hetaryloxyalkyl, unsubstituted or substituted hetarylthioalkyl, unsubstituted or substituted alkenyl, unsubstituted or substituted aralkenyl, unsubstituted or substituted aryloxyalkenyl, unsubstituted or substituted arylthioalkenyl, unsubstituted or substituted hetarylalkenyl, unsubstituted or substituted hetaryloxyalkenyl, unsubstituted or substituted hetarylthioalkenyl, unsubstituted or substituted alkynyl, unsubstituted or substituted arylalkynyl, unsubstituted or substituted hetarylalkynyl, unsubstituted or substituted aryl, unsubstituted or substituted hetaryl, unsubstituted or substituted arylazo, unsubstituted or substituted acylamino, —$OR^{12}$, —$SR^{13}$, —$SOR^{14}$, —$SO_2R^{15}$, —$COOR^{16}$, —$CONR^{17}R^{18}$, —$COR^{19}$, —$CR^{20}$=$NR^{21}$, —N=$CR^{22}R^{23}$, —$CR^{24}$=N—$OR^{25}$, —$CR^{25}R^{26}$—O—N=$CR^{27}R^{28}$, —$CH_2$—$OCOR^{39}$ or —$NR^{37}R^{38}$, where $R^{12}$ to $R^{28}$ and $R^{38}$ and $R^{39}$ are identical or different and are hydrogen, unsubstituted or substituted alkyl, unsubstituted or substituted alkenyl, unsubstituted or substituted alkynyl, unsubstituted or substituted cycloalkyl, unsubstituted or substituted cycloalkylalkyl, unsubstituted or substituted aryl, unsubstituted or substituted hetaryl, unsubstituted or substituted aralkyl, unsubstituted or substituted hetarylalkyl, unsubstituted or substituted aryloxyalkyl, unsubstituted or substituted arylthioalkyl, unsubstituted or substituted hetaryloxyalkyl or unsubstituted or substituted hetarylthioalkyl, and $R^{37}$ is hydrogen or $C_1$–$C_4$-alkyl, and where U, V and W are identical or different and are hydrogen or have one of the meanings specified for Z, or where two of the groups Z, U, V or W in adjacent positions on the phenyl ring may together with the carbon atoms to which they are attached form an unsubstituted or substituted five- or six-membered aromatic or aliphatic ring which is fused onto the phenyl ring and may contain one to three hetero atoms (N, S, O), provided that said compound does not include 3-methylmercapto-3-(1-naphythyl)acrylic acid ethyl ester and an alkyl ester of (p-terphenyl)-2'-carboxylic acid-3'-(2-carboxy-1-methoxy vinyl)-2'-methyl ester, and an inert carrier.

8. The β-substituted cinnamic acid derivative of claim 1, wherein $R^{12}$ of formula 1 is a substituted alkyl, alkenyl, alkynyl, unsubstituted or substituted cycloalkyl, cycloalkylalkyl, and unsubstituted or substituted aryl, hetaryl, aralkyl, hetarylalkyl, aryloxyalkyl, arylthioalkyl, hetaryloxyalkyl or hetarylthioalkyl.

9. The β-substituted cinnamic acid derivative of claim 1, wherein $R^{12}$ of formula 1 is substituted alkyl, alkenyl, alkynyl, cycloalkyl, cycloalkylalkyl, and unsubstituted or substituted aryl, hetaryl, aralkyl, hetarylalkyl, aryloxyalkyl, arylthioalkyl, hetaryloxyalkyl or hetarylthioalkyl.

10. The β-substituted cinnamic acid derivative of claim 9, wherein $R^{12}$ of formula 1 is unsubstituted or substituted aryl, hetaryl, aralkyl, hetarylalkyl, aryloxyalkyl, arylthioalkyl, hetaryloxyalkyl or hetarylthioalkyl.

11. A β-substituted cinnamic acid derivative as claimed in claim 1, wherein Z is 2—$CH_3$—4—[$CH_3$—O—N=C($CH_3$)]—$C_6H_3$—$OCH_2$—, U, V and W are H, $R^1X_m$ is methoxy and Y is methoxy.

12. A β-substituted cinnamic acid derivative of the formula 1,

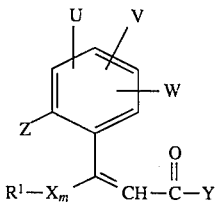

(1)

where $R^1$ is unsubstituted or halogen-, $C_1$–$C_6$-alkoxy-, $C_1$–$C_6$-alkylthio- or $C_3$–$C_6$-cycloalkyl-substituted $C_1$–$C_6$-alkyl, $C_2$–$C_8$-alkenyl, $C_2$–$C_8$-alkynyl, $C_3$–$C_8$-cycloalkyl or $C_3$–$C_8$-cycloalkenyl, —X— is —O—, —S—,

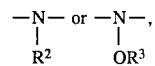

m is 1,

—Y is —$OR^4$, —O—N=$CR^5R^6$, —$NR^7R^8$, —N($OR^9$)$R^{10}$ or —$SR^{11}$, where the substituents $R^2$ to $R^{11}$ are, independently of one another, identical or different and each is unsubstituted or halogen-, $C_1$–$C_6$-alkoxy-, $C_1$–$C_6$-alkylthio- or $C_3$–$C_6$-cycloalkyl-substituted, $C_1$–$C_8$-alkyl, $C_2$–$C_8$-alkenyl, $C_2$–$C_8$-alkynyl, $C_3$–$C_8$-cycloalkyl or $C_3$–$C_8$-cycloalkenyl, Z is halogen, nitro, cyano, unsubstituted or substituted alkyl, unsubstituted or substituted cycloalkyl, unsubstituted or substituted aralkyl, unsubstituted or substituted aryloxyalkyl, unsubstituted or substituted arylthioalkyl, unsubstituted or substituted hetarylalkyl, unsubstituted or substituted hetaryloxyalkyl, unsubstituted or substituted hetarylthioalkyl, unsubstituted or substituted alkenyl, unsubstituted or substituted aralkenyl, unsubstituted or substituted aryloxyalkenyl, unsubstituted or substituted arylthioalkenyl, unsubstituted or substituted hetarylalkenyl, unsubstituted or substituted hetaryloxyalkenyl, unsubstituted or substituted hetarylthioalkenyl, unsubstituted or substituted alkynyl, unsubstituted or substituted arylalkynyl, unsubstituted or substituted hetarylalkynyl, unsubstituted or substituted aryl, unsubstituted or substituted hetaryl, unsubstituted or substituted arylazo, unsubstituted or substituted acylamino, —$OR^{12}$, —$SR^{13}$, —$SOR^{14}$, —$SO_2R^{15}$, —$COOR^{16}$, —$CONR^{17}R^{18}$, —$COR^{19}$, —$CR^{20}$=$NR^{21}$, —N=$CR^{22}R^{23}$, —$CR^{24}$=N—$OR^{25}$, —$CR^{25}R^{26}$—O—N=$CR^{27}R^{28}$, —$CH_2$—$OCOR^{39}$ or —$NR^{37}R^{38}$, provided that when U, V and W are simultaneously hydrogen, Z is not methoxy, where $R^{12}$ to $R^{28}$ and $R^{38}$ and $R^{39}$ are identical or different and are hydrogen, unsubstituted or substituted alkyl, unsubstituted or substituted alkenyl, unsubstituted or substituted alkynyl, unsubstituted or substituted cycloalkyl, unsubstituted or substituted cycloalkylalkyl, unsubstituted or substituted aryl, unsubstituted or substituted hetaryl, unsubstituted or substituted aralkyl, unsubstituted or substituted hetarylalkyl, unsubstituted or substituted aryloxyalkyl, unsubstituted or substituted arylthioalkyl, unsubstituted or substituted hetaryloxyalkyl or unsubstituted or substituted hetarylthioalkyl, and $R^{37}$ is hydrogen or $C_1$–$C_4$-alkyl, and where U, V and W are identical or different and are hydrogen or have one of the meanings specified for Z, or where two of the groups Z, U, V or W in adjacent positions on the phenyl ring may together with the carbon atoms to which they are attached form an unsubstituted or substituted five- or six-membered aromatic or aliphatic ring which is fused onto the phenyl ring and may contain one to three hetero atoms (N, S, O), provided that said derivative of formula 1 does not include an alkyl ester of (p-terphenyl)-2'-carboxylic acid-3'-(2-carboxy-1-methoxy vinyl)-2'-methyl ester.

* * * * *